United States Patent

Maccoss et al.

Patent Number: 6,013,652
Date of Patent: Jan. 11, 2000

[54] SPIRO-SUBSTITUTED AZACYCLES AS NEUROKININ ANTAGONISTS

[75] Inventors: Malcolm Maccoss, Freehold; Sander G. Mills, Woodbridge; Shrenik K. Shah, Metuchen; Yuan-Ching P. Chiang, Scotch Plains; Patrick T. Dunn, Woodbridge; Hiroo Koyama, Westfield, all of N.J.

[73] Assignee: Merck & Co., Inc., Rahway, N.J.

[21] Appl. No.: 08/985,338

[22] Filed: Dec. 4, 1997

Related U.S. Application Data

[63] Continuation of application No. 08/553,454, filed as application No. PCT/US94/05545, May 17, 1994, which is a continuation-in-part of application No. 08/072,904, Jun. 7, 1993, abandoned.

[51] Int. Cl.$^7$ .......................... A61K 31/44; C07D 401/02
[52] U.S. Cl. ....................... 514/278; 514/226.5; 514/258; 514/373; 514/409; 544/6; 544/230; 546/17; 546/18; 548/207; 548/409; 548/410
[58] Field of Search ................................ 514/278; 546/17

[56] References Cited

U.S. PATENT DOCUMENTS

| | | | |
|---|---|---|---|
| 3,301,857 | 1/1967 | Berger et al. | 260/288 |
| 4,233,307 | 11/1980 | Ono et al. | 424/267 |
| 4,420,485 | 12/1983 | Davis et al. | 424/267 |
| 5,091,387 | 2/1992 | Evans et al. | 514/278 |
| 5,434,158 | 7/1995 | Shah | 514/278 |
| 5,536,716 | 7/1996 | Chen et al. | 514/215 |
| 5,756,507 | 5/1998 | Goulet et al. | 514/255 |

FOREIGN PATENT DOCUMENTS

| | | |
|---|---|---|
| 0 360 390 | 3/1990 | European Pat. Off. . |
| 0 428 434 | 5/1991 | European Pat. Off. . |
| 0 431 943 | 6/1991 | European Pat. Off. . |
| 0 450 761 | 10/1991 | European Pat. Off. . |
| 0 474 561 | 3/1992 | European Pat. Off. . |
| 0 518 805 | 12/1992 | European Pat. Off. . |

OTHER PUBLICATIONS

Biochem and Biophys Res. Comm vol. 184, No. 3, pp. 1418–1424 (May 15, 1992).
Life Sciences, vol. 50, No. 15, pp. PL–101 PL–106 (1992).
J. Pharmacol (1993) 108, 844–851, Y. Hirayama, et al.
J. Auton Pharmacol (1993) 13, 23–93, C. Alberto Maggi, et al.
Misztal, et al, Chem. Ab., vol. 110, No. 21, 193172d (1989).
Ong, et al, Journ. of Heterocyclic Chem., vol. 18, pp. 815–820 (1981).
Hoechst, Chem. Ab., vol. 90, No. 17, 137699n (1979).
J. T. Bigger, Jr., et al., Goodman and Gilman's, The Pharmacological Basis of Therapeutics Eight Edition, "Antiarrhythmic Drugs" pp. 840–873, 1990.
CAS Online printout for WO 93/15051, Aug. 1993.
CAS Online printout for JP 03096942, Apr. 1991.
CAS Online printout for JP 53132578, Nov. 1978.
CAS Online printout for BE 867517, Sep. 1978.
CAS Online printout for JP 53068784, Jun. 1978.

*Primary Examiner*—Mukund J. Shah
*Assistant Examiner*—Brenda Coleman
*Attorney, Agent, or Firm*—Richard C. Billups; David L. Rose

[57] ABSTRACT

Disclosed are spiro-substituted azacycles of formula I

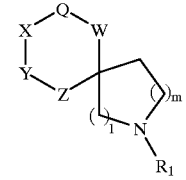

are tachykinin receptor antagonists useful in the treatment of inflammatory diseases, pain or migraine, and asthma. In particular compounds of formula I are shown to be neurokinin antagonists.

2 Claims, No Drawings

SPIRO-SUBSTITUTED AZACYCLES AS NEUROKININ ANTAGONISTS

CROSS REFERENCE TO RELATED APPLICATIONS

This application is a continuation of U.S. application Ser. No. 08/553,454, filed on Nov. 27, 1995, now abandoned, which was the U.S. national phase of PCT/US94/05545 filed on May 17, 1994, which was a continuation in part of U.S. application Ser. No. 08/072,904, filed on Jun. 7, 1993, and abandoned, priority of which is claimed hereunder.

BACKGROUND OF THE INVENTION

The invention disclosed herein is directed to certain spiro-substituted azacycles useful as tachykinin receptor antagonists. In particular, the compounds disclosed herein are neurokinin receptor antagonists.

The tachykinins, substance P (SP), neurokinin A (NKA) and neurokinin B (NKB), are structurally similar members of a family of neuropeptides. Each of these is an agonist of the receptor types, neurokinin-1 receptor (NK-1), neuorokinin-2 receptor (NK-2) and neuorokinin-3 receptor (NK-3), which are so defined according to their relative abilities to bind tachykinins with high affinity and to be activated by the natural agonists SP, NKA and NKB respectively.

The tachykinins are distinguished by a conserved carboxyl-terminal sequence Phe-X-Gly-Leu-Met-$NH_2$. More specifically, substance P is a pharmacologically-active neuropeptide that is produced in mammals and possesses a characteristic amino acid sequence:
Arg-Pro-Lys-Pro-Gln-Gln-Phe -Phe-Gly-Leu-Met-$NH_2$.
Neurokinin A possesses the following amino acid sequence:
His-Lys-Thr-Asp-Ser-Phe-Val-Gly-Leu-Met-$NH_2$.
Neurokinin B possesses the following amino acid sequence:
Asp-Met-His-Asp -Phe-Phe-Val-Gly-Leu-Met-$NH_2$.
(Chang et al., Nature New Biol. 232, 86 (1971); D. F. Veber et al., U.S. Pat. No. 4,680,283).

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol. Rev., 1983, 35, 85–141). The NK1 and NK2 receptor subtypes are implicated in synaptic transmission (Laneuville et al., Life Sci., 42: 1295–1305 (1988)).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science, 199, 1359 (1978); P. Oehme et al., Science, 208, 305 (1980)) and plays a role in sensory transmission and pain perception (T. M. Jessell, Advan. Biochem. Psychopharmacol. 28, 189 (1981)). In particular, substance P has been shown to be involved in the transmission of pain in migraine (see B. E. B. Sandberg et al., Journal of Medicinal Chemistry, 25, 1009 (1982)), and in arthritis (Levine et al. Science, (1984) 226, 547–549).

In the airways, it has been indicated that NK1 receptors are associated with microvascular leakage and mucus secretion, while NK2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al., Life Sci., 49, 1941–1953 (1991); Advenier, et al., Biochem. Biophys. Res. Comm., 184(3), 1418–1424 (1992)).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (Barnes P. J., Lancet, pp 242–44 (1986); Rogers D. R., Aursudkij B., Barnes P. J., Euro. J. Pharmacol, 174, 283–86 (1989)).

Inhalation of bradykinin causes bronchoconstriction in asthmatic patients but not in normal subjects. (Fuller R. W., Dixon C. M. S., Cuss F. M. C., Barnes P. J., Am Rev Respir Dis, 135, 176–80 (1987)). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes bronchoconstriction in dogs. (Kaufman M. P., Coleridge H. M., Coleridge J. C. G., Baker D. G., J. Appl. Physio., 48, 511–17 (1980)). In guinea-pig airways, bradykinin causes a bronchoconstrictor response by way of cholinergic and sensory-nerve-mediated mechanisms. (Ichinoe M., Belvisi M. G., Barnes P. J., J. Pharmacol. Exp. Ther., 253, 594–99 (1990). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchocontriction in asthmatic patients. (Ichinoe, M. et al., Lancet, vol. 340, pp 1248–1251 (1992)).

The tachykinins have also been implicated in gastrointestinal (GI) disorders and diseases of the GI tract, such as inflammatory bowel disease, ulcerative colitis and Crohn's disease, etc. (see Mantyh et al., Neuroscience, 25 (3), 817–37 (1988) and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in The Lancet, Nov. 11, 1989 and Gronblad et al., "Neuropeptides in Synovium of Patients with Rheumatoid Arthritis and Osteoarthritis" in J. Rheumatol. (1988) 15(12) 1807–10). Therefore, substance P is believed to be involved in the inflammatory response in diseases such as rheumatoid arthritis and osteoarthritis (O'Byrne et al., in Arthritis and Rheumatism (1990) 33, 1023–8). Other disease areas where tachykinin antagonists are believed to be useful are allergic conditions (Hamelet et al., Can. J. Pharmacol. Physiol. (1988) 66, 1361–7), immunoregulation (Lotz et al., Science (1988) 241, 1218–21, Kimball et al., J. Immunol. (1988) 141 (10) 3564–9 and A. Perianin, et al., Biochem. Biophys. Res. Commun. 161, 520 (1989)) vasodilation, bronchospasm, reflex or neuronal control of the viscera (Mantyh et al., PNAS (1988) 85, 3235–9) and, possibly by arresting or slowing β-amyloid-mediated neurodegenerative changes (Yankner et al., Science, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis (J. Luber-Narod et al., poster presented at C.I.N.P. XVIIIth Congress, Jun. 28th–Jul. 2nd, 1992). Antagonists selective for the substance P and/or the neurokinin A receptor may be useful in the treatment of asthmatic disease (Frossard et al., Life Sci., 49, 1941–1953 (1991); Advenier, et al., Biochem. Biophys. Res. Comm., 184(3), 1418–1424 (1992)).

SUMMARY OF THE INVENTION

This invention is directed to compounds of formula I.

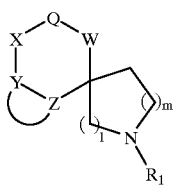

I

The invention is also concerned with pharmaceutical formulations with these novel compounds as active ingredients and the use of the novel compounds and their formulations in the treatment of certain disorders.

The compounds of this invention are tachykinin receptor antagonists and are useful in the treatment of inflammatory diseases, pain or migraine and asthma.

DETAILED DESCRIPTION OF THE INVENTION

This invention is directed to compounds of formula I.

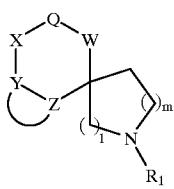

I or a pharmaceutically acceptable salt thereof,
wherein the nitrogen expressly shown above is optionally quaternized with $C_{1-4}$alkyl or phenyl$C_{1-4}$alkyl or is optionally present as the N-oxide (N+O−), and wherein:

1 and m are each independently 0, 1, 2, 3, 4, or 5, with the proviso that 1+m is equal to 1, 2, 3, 4, or 5;

$R_1$ is selected from a group consisting of:
(1) hydrogen,
(2) linear or branched $C_{1-8}$ alkyl, linear or branched $C_{2-8}$ alkenyl, or linear or branched $C_{2-8}$ alkynyl, wherein the $C_{1-8}$ alkyl, $C_{2-8}$ alkenyl or $C_{2-8}$ alkynyl is optionally mono, di, tri or tetra substituted, the substitutents independently selected from:
(a) hydroxy,
(b) oxo,
(c) cyano,
(d) halogen which is defined to include Br, Cl, I, and F,
(e) trifluoromethyl,
(f) phenyl or mono, di or trisubstituted phenyl, the substitutents independently selected from
(1) phenyl,
(2) hydroxy,
(3) $C_{1-3}$alkyl,
(4) cyano,
(5) halogen,
(6) trifluoromethyl,
(7) —$NR_6COR_7$, wherein $R_6$ and $R_7$ are independently selected from:
(a) hydrogen,
(b) $C_{1-6}$ alkyl, or mono or disubstituted $C_{1-6}$ alkyl, the substitutents independently selected from
(1) phenyl, unsubstituted or substituted with hydroxy, $C_{1-3}$alkyl, cyano, halogen, trifluoromethyl or $C_{1-4}$alkoxy,
(2) hydroxy,
(3) oxo,
(4) cyano,
(5) halogen,
(6) trifluoromethyl,
(c) phenyl, pyridinyl or thiophene or mono, di or trisubstituted phenyl, pyridinyl or thiophene, the substitutents independently selected from
(1) hydroxy,
(2) $C_{1-4}$alkyl,
(3) cyano,
(4) halogen,
(5) trifluoromethyl,
(d) $C_{1-3}$alkyloxy, or
$R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from
(a) hydroxy,
(b) oxo,
(c) cyano,
(d) halogen,
(e) trifluoromethyl,
(8) —$NR_6CO_2R_7$,
(9) —$NR_6CONHR_7$,
(10) —$NR_6S(O)_jR_7$, wherein j is 1 or 2,
(11) —$CONR_6R_7$,
(12) —$COR_6$,
(13) —$CO_2R_6$,
(14) —$OR_6$,
(15) —$S(O)_kR_6$ wherein k is 0, 1 or 2,
(16) heteroaryl, wherein heteroaryl is selected from the group consisting of:
(1) benzimidazolyl,
(2) benzofuranyl,
(3) benzoxazolyl,
(4) furanyl,
(5) imidazolyl,
(6) indolyl,
(7) isoxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl, and

(21) triazolyl,
wherein the heteroaryl is unsubstituted or mono, di or trisubstituted, the substituents independently selected from,
(a) hydroxy,
(b) oxo,
(c) cyano,
(d) halogen,
(e) trifluoromethyl,
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$,
(p) —$S(O)_kR_6$,
(q) heteroaryl, wherein heteroaryl is selected from the group consisting of:
 (1) benzimidazolyl,
 (2) benzofuranyl,
 (3) benzoxazolyl,
 (4) furanyl,
 (5) imidazolyl,
 (6) indolyl,
 (7) isoxazolyl,
 (8) isothiazolyl,
 (9) oxadiazolyl,
 (10) oxazolyl,
 (11) pyrazinyl,
 (12) pyrazolyl,
 (13) pyridyl,
 (14) pyrimidyl,
 (15) pyrrolyl,
 (16) quinolyl,
 (17) tetrazolyl,
 (18) thiadiazolyl,
 (19) thiazolyl,
 (20) thienyl,
 (21) triazolyl,
wherein the heteroaryl is unsubstituted or mono di or trisubstituted, the substituents independently selected from
 (1) phenyl,
 (2) hydroxy,
 (3) oxo,
 (4) cyano,
 (5) halogen,
 (6) trifluoromethyl,
wherein the nitrogen of definition $R_1$ 2(g) as defined above is optionally quaternized with $C_{1-4}$alkyl or phenyl$C_{1-4}$alkyl or is optionally present as the N-oxide (N+O−);
W is selected from the group consisting of
(1) a covalent bond
(2) $C_{1-3}$ alkyl, unsubstituted or substituted with
 (a) oxo,
 (b) hydroxy
 (c) $OR_6$,
 (d) halogen,
 (e) trifluoromethyl,
 (f) phenyl or mono, di or trisubstituted phenyl, the substitutents independently selected from
(1) hydroxy,
(2) cyano,
(3) halogen,
(4) trifluoromethyl,
(3) $S(O)_k$,
(4) ($C_{1-3}$ alkyl)—$S(O)_k$,
(5) $S(O)_k$—($C_{1-2}$ alkyl),
(6) $S(O)_k$—NH,
(7) $S(O)_j$—NH($C_{1-2}$ alkyl),
(8) $S(O)_j$—$NR_6$,
(9) $S(O)_j$—$NR_6$—($C_{1-2}$ alkyl),
(10) CONH,
(11) CONH—($C_{1-2}$ alkyl),
(12) $CONR_6$,
(13) $CONR_6$—($C_{1-2}$ alkyl),
(14) $CO_2$,
(15) $CO_2$—($C_{1-2}$ alkyl);
Q=$NR_2$, O, S, S(O), or $SO_2$, with the proviso that when W is a covalent bond and X is $C_{1-3}$alkyl, then Q must be $NR_2$;
$R_2$ is selected from a group consisting of:
(1) hydrogen,
(2) $C_{1-8}$ linear or branched alkyl, unsubstituted, monosubstituted or multiply substituted with
 (a) —$OR_6$,
 (b) =O,
 (c) —$NHCOR_6$,
 (d) —$NR_6R_7$,
 (e) —CN,
 (f) —halogen,
 (g) —$CF_3$,
 (h) -phenyl, unsubstituted or substituted, wherein the substitutents are selected from the group consisting of
  (1) hydroxy,
  (2) cyano,
  (3) halogen,
  (4) trifluoromethyl,
(3) $S(O)R_8$, wherein $R_8$ is $C_{1-6}$ linear or branched alkyl, unsubstituted, mono di or trisubstituted with
 (a) hydroxy,
 (b) oxo,
 (c) cyano,
 (d) —$OR_6$,
 (e) —$NR_6R_7$,
 (f) —$NR_6COR_7$,
 (g) -halogen,
 (h) —$CF_3$,
 (i) -phenyl or mono, di or trisubstituted phenyl, the substituents independently selected from
  (1) hydroxy,
  (2) oxo,
  (3) cyano,
  (4) —$NHR_6$,
  (5) —$NR_6R_7$,
  (6) —$NR_6COR_7$,
  (7) -halogen,
  (8) —$CF_3$, and
  (9) $C_{1-3}$ alkyl,
(4) $SO_2R_8$,
(5) $COR_8$,
(6) $CO_2R_8$,
(7) $CONR7R_8$,
X is selected from the group consisting of
(1) a covalent bond
(2) $C_{1-3}$ alkyl, unsubstituted or substituted with
 (a) oxo,
 (b) $OR_6$, (c) halogen,
(d) trifluoromethyl,
(e) phenyl or mono, di or trisubstituted phenyl, the substitutents independently selected from
  (1) OR$_6$,
  (2) halogen, and
  (3) trifluoromethyl,
(3) S(O)$_k$,
(4) (C$_{1-3}$ alkyl)S(O)$_k$,
(5) S(O)$_k$(C$_{1-2}$ alkyl),
(6) NHS(O)j,
(7) NH(C$_{1-2}$ alkyl)S(O)j,
(8) S(O)jNR$_6$,
(9) S(O)j-NR$_6$—(C$_{1-2}$ alkyl),
(10) NHCO,
(11) NHCO—(C$_{1-2}$ alkyl),
(12) NR$_6$CO,
(13) NR$_6$—(C$_{1-2}$ alkyl)CO,
(14) O(CO), and
(15) (C$_{1-2}$ alkyl)O(CO),
Y-Z considered together are 2 adjoining atoms of the ring

said ring being an phenyl, naphthyl or heteroaryl group, with the heteroaryls selected from the group consisting of:
(1) benzimidazolyl,
(2) benzofuranyl,
(3) benzoxazolyl,
(4) furanyl,
(5) imidazolyl,
(6) indolyl,
(7) isoxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl,
(21) triazolyl,
and wherein the aryl or heteroaryl group is unsubstituted, mono, di or tri substituted, the substitutents selected from:
  (a) hydrogen,
  (b) C$_{1-6}$ alkyl, branched or unbranched, unsubstituted or mono or disubstituted, the substituents being selected from hydrogen and hydroxy,
  (c) oxo
  (d) OR$_6$, wherein R$_6$ is as defined immediately above,
  (e) halogen,
  (f) trifluoromethyl,
  (g) nitro,
  (h) cyano,
  (i) NHR$_6$,
  (j) NR$_6$R$_7$,
  (k) NHCOR$_6$,
  (l) NR$_6$COR$_7$,
  (m) NHCO$_2$R$_6$,
  (n) NR$_6$CO$_2$R$_7$,
  (o) NHS(O)$_j$R$_6$,
  (p) NR$_6$S(O)$_j$R$_7$,
  (q) CONR$_6$R$_7$,
  (r) COR$_6$,
  (s) CO$_2$R$_6$,
  (t) S(O)$_j$R$_6$,
  (u) heteroaryl, wherein heteroaryl is selected from the group consisting of:
    (a) benzimidazolyl,
    (b) benzofuranyl,
    (c) benzoxazolyl,
    (d) furanyl,
    (e) imidazolyl,
    (f) indolyl,
    (g) isoxazolyl,
    (h) isothiazolyl,
    (i) oxadiazolyl,
    (j) oxazolyl,
    (k) pyrazinyl,
    (l) pyrazolyl,
    (m) pyridyl,
    (n) pyrimidyl,
    (o) pyrrolyl,
    (p) quinolyl,
    (q) tetrazolyl,
    (r) thiadiazolyl,
    (s) thiazolyl,
    (t) thienyl,
    (u) triazolyl,
    and wherein the heteroaryl is unsubstituted mono or di substituted, the substituents selected from
      (1) hydrogen,
      (2) C$_{1-6}$ alkyl, branched or unbranched, unsubstituted or mono or disubstituted, the substituents being selected from hydrogen and hydroxy,
      (3) oxo,
      (4) OR$_6$,
      (5) trifluoromethyl,
      (6) nitro,
      (7) cyano,
      (8) NHR$_6$,
      (9) NR$_6$R$_7$,
      (10) NHCOR$_6$,
      (11) NR$_6$COR$_7$,
      (12) NHCO$_2$R$_6$,
      (13) NR$_6$CO$_2$R$_7$,
      (14) NHS(O)$_j$R$_6$,
      (15) NR$_6$S(O)$_j$R$_7$,
      (16) CONR$_6$R$_7$,
      (17) COR$_6$,
      (18) CO$_2$R$_6$,
      (19) S(O)$_j$R$_6$, and
      (20) phenyl.

One subclass of this invention consists of structures tabulated below linked to R$_1$ (as detailed immediately above) via the broken bond, and optionally substituted at the positions indicated by numbers 1–8 with
  (a) hydroxy,
  (b) oxo,
  (c) cyano,
  (d) —NR$_6$R$_7$,
  (e) —NHCOR$_6$R$_7$,
  (f) -halogen, (g) —CF$_3$,
(h) -phenyl or mono, di or trisubstituted phenyl, the substituents independently selected from (a) through (g) and C$_{1-3}$ alkyl;
the tabulated structures being
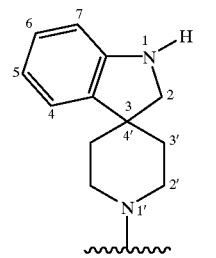 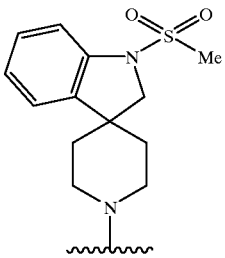
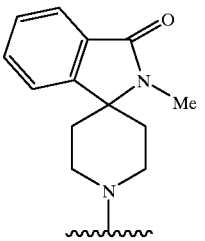 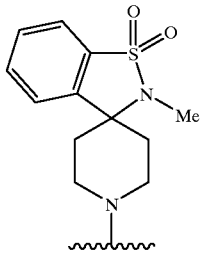
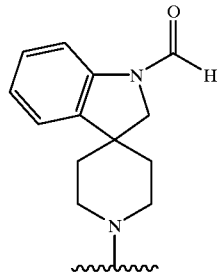 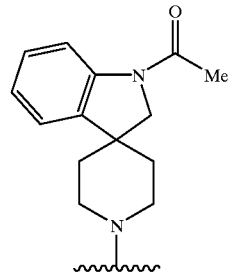
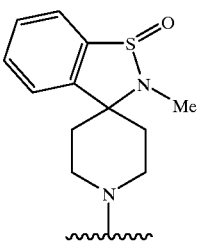 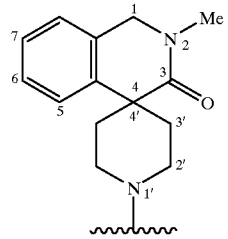
-continued
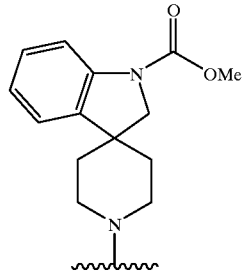 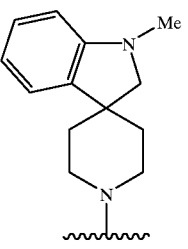
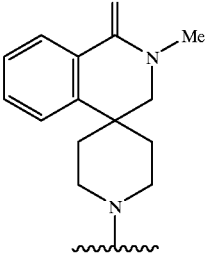 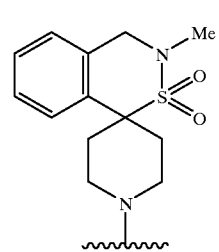
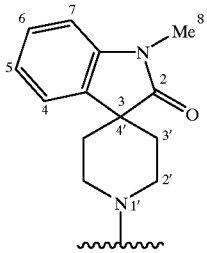 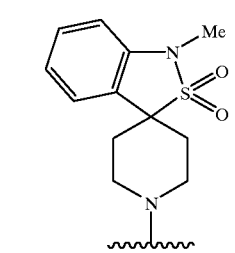
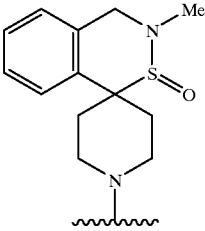 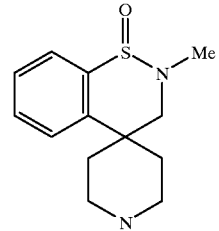
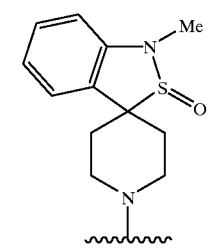 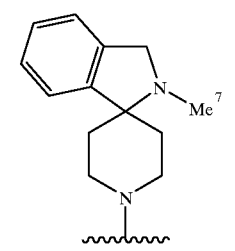
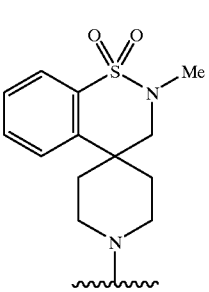 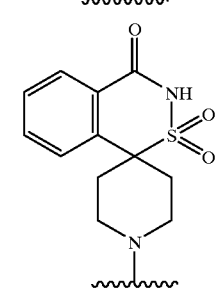
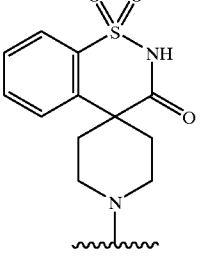 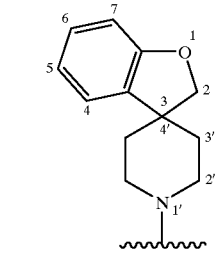

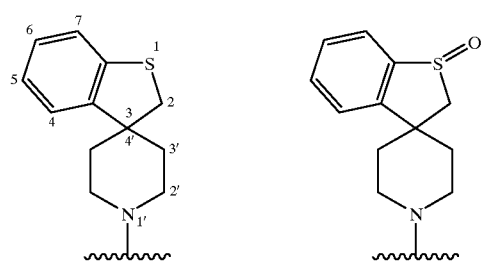
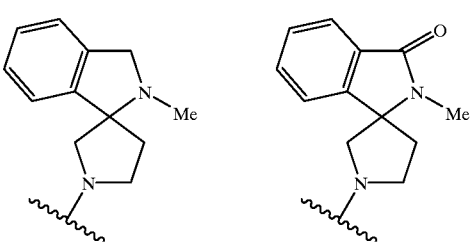
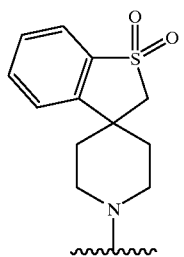
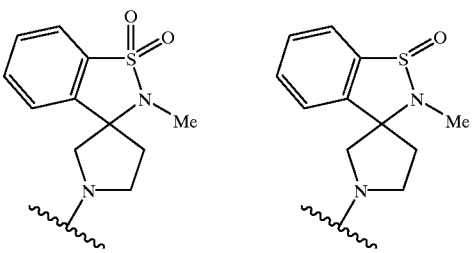
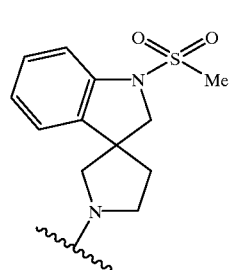
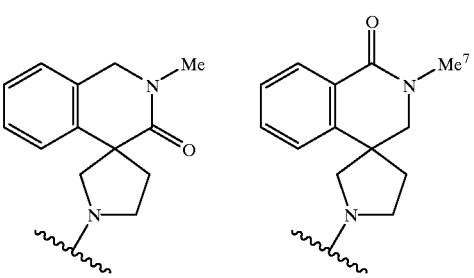
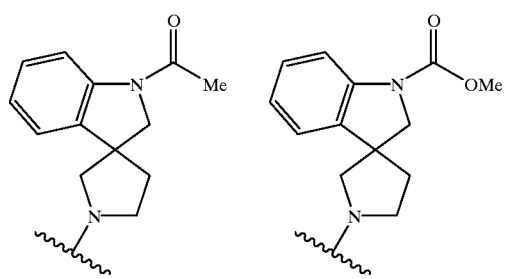
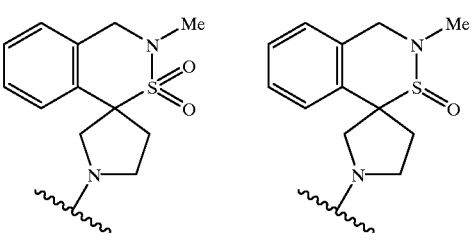
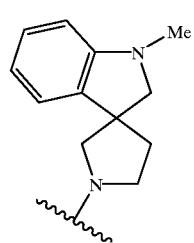
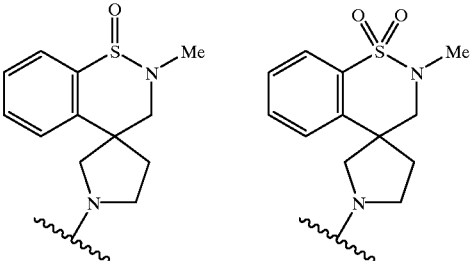
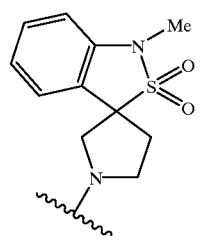
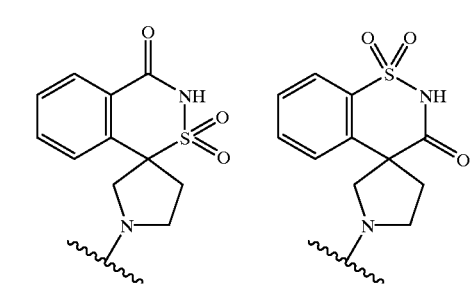

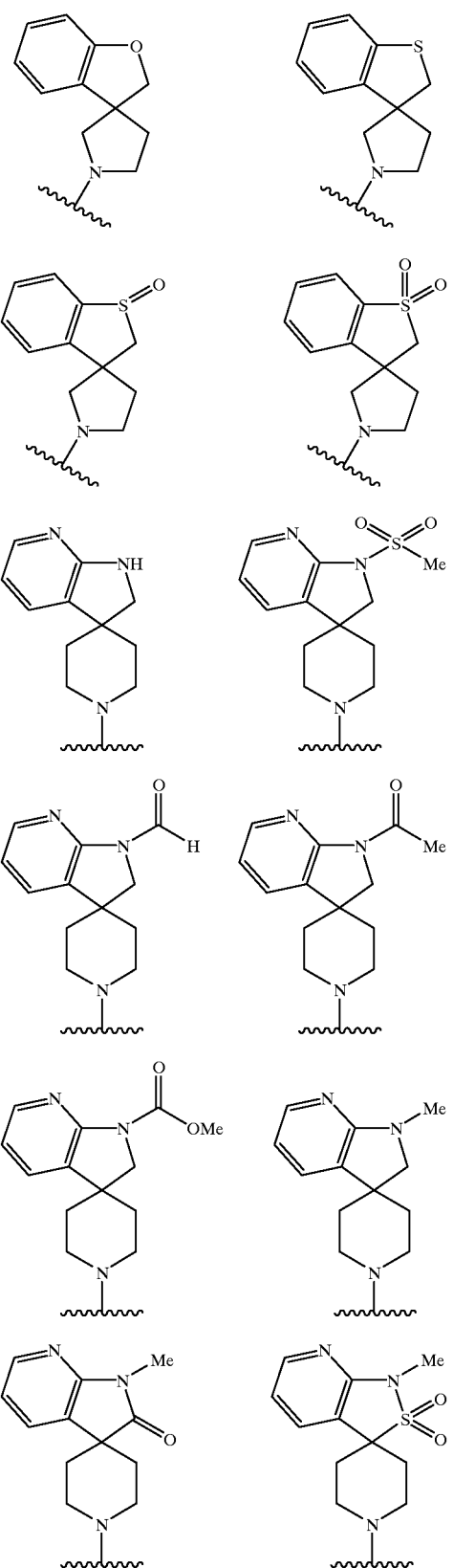
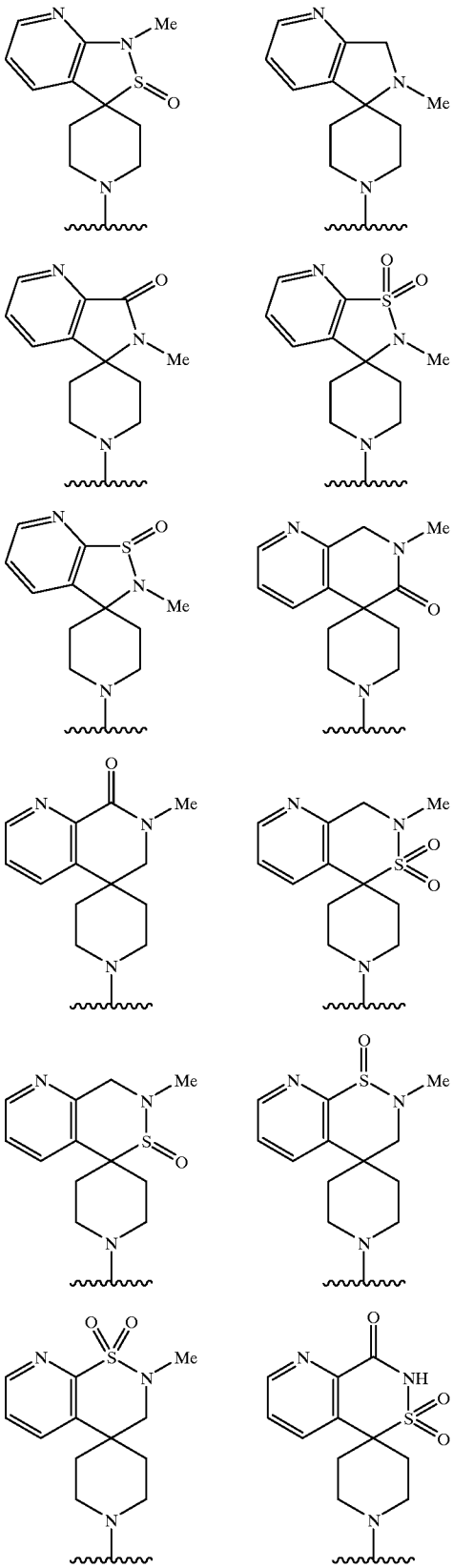

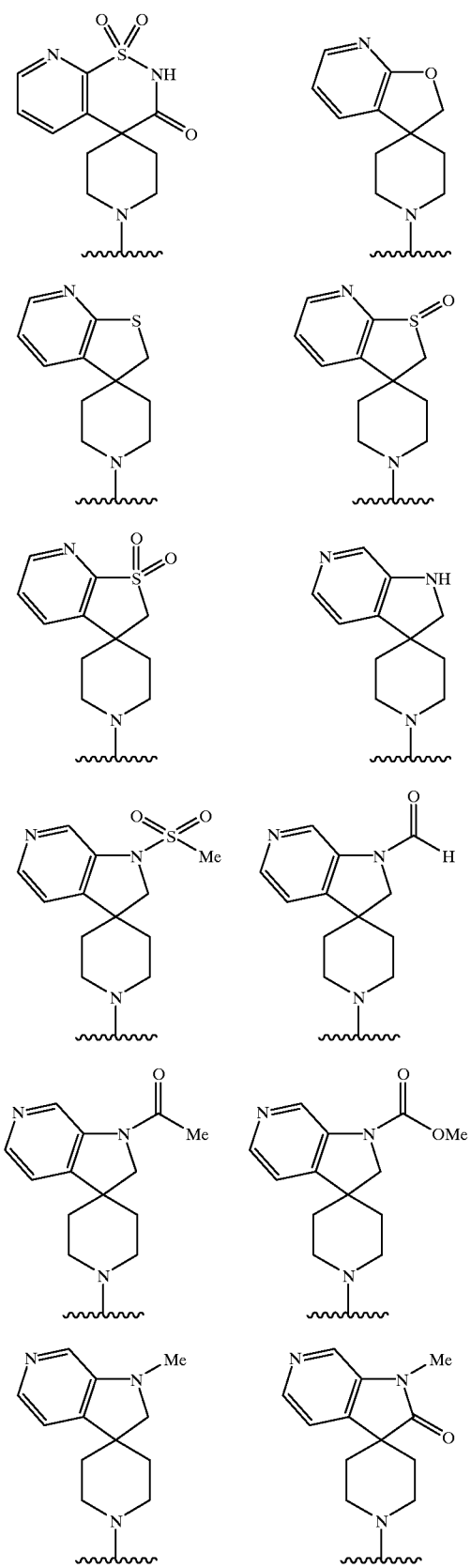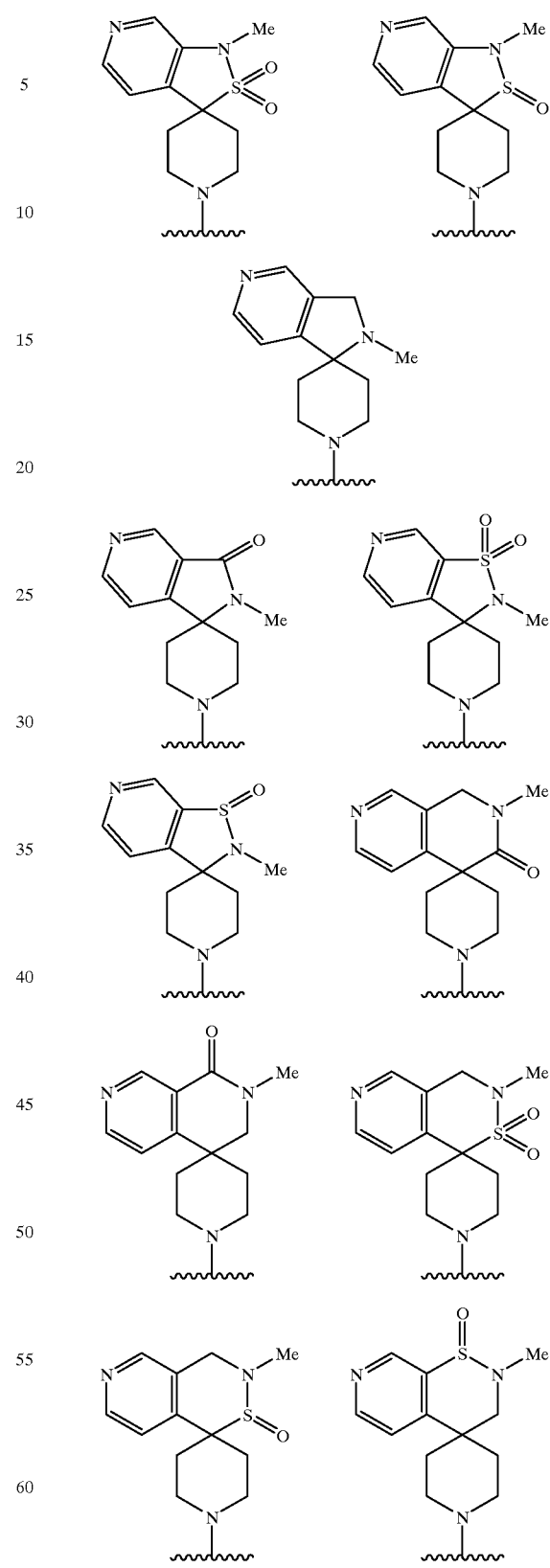

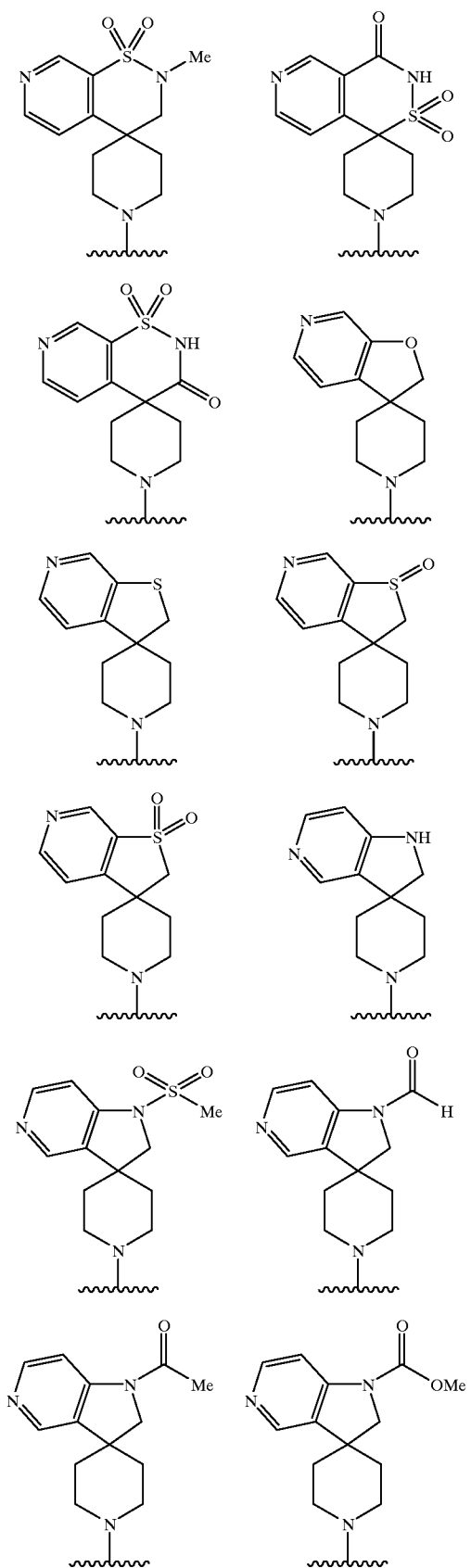
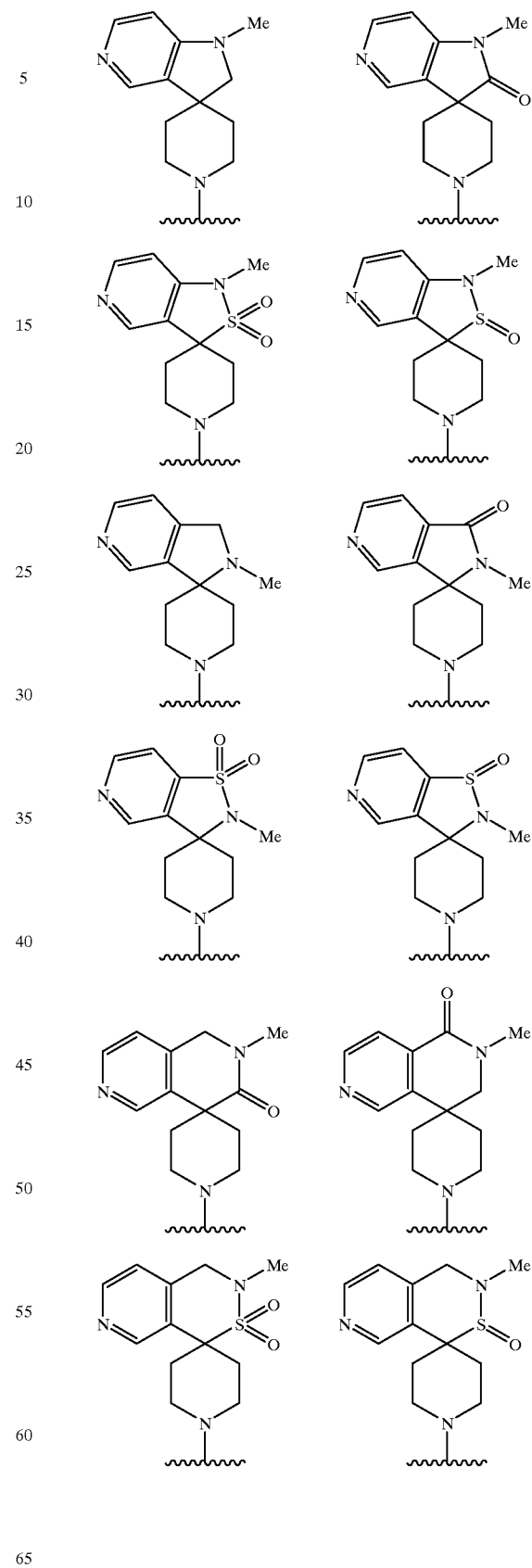

-continued
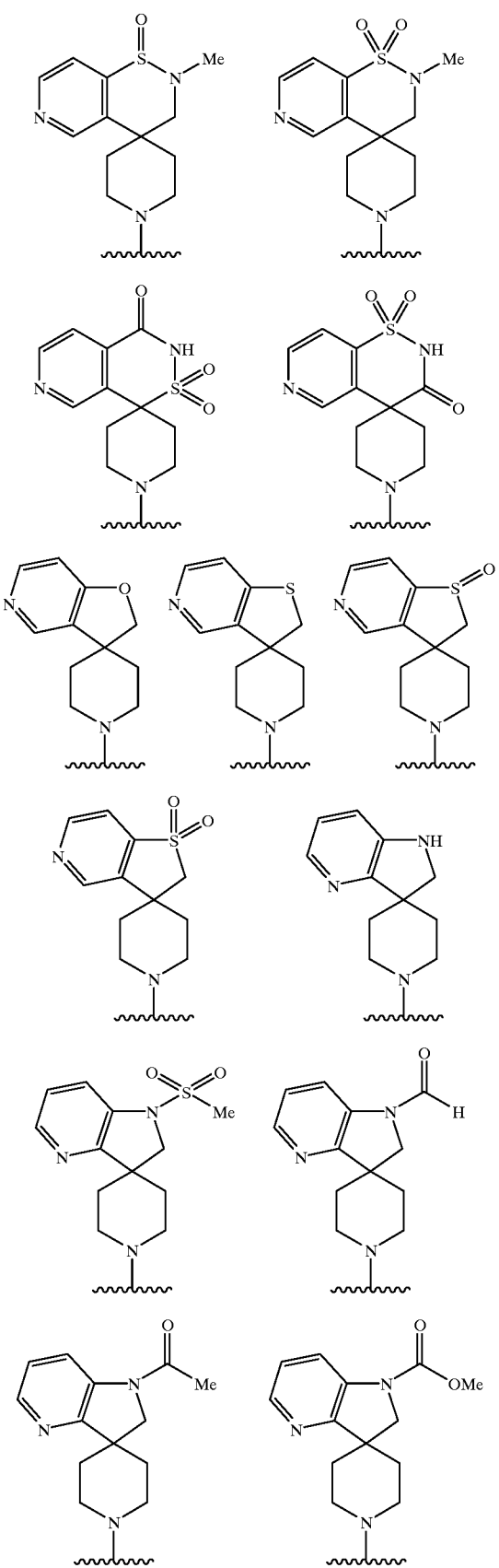
-continued
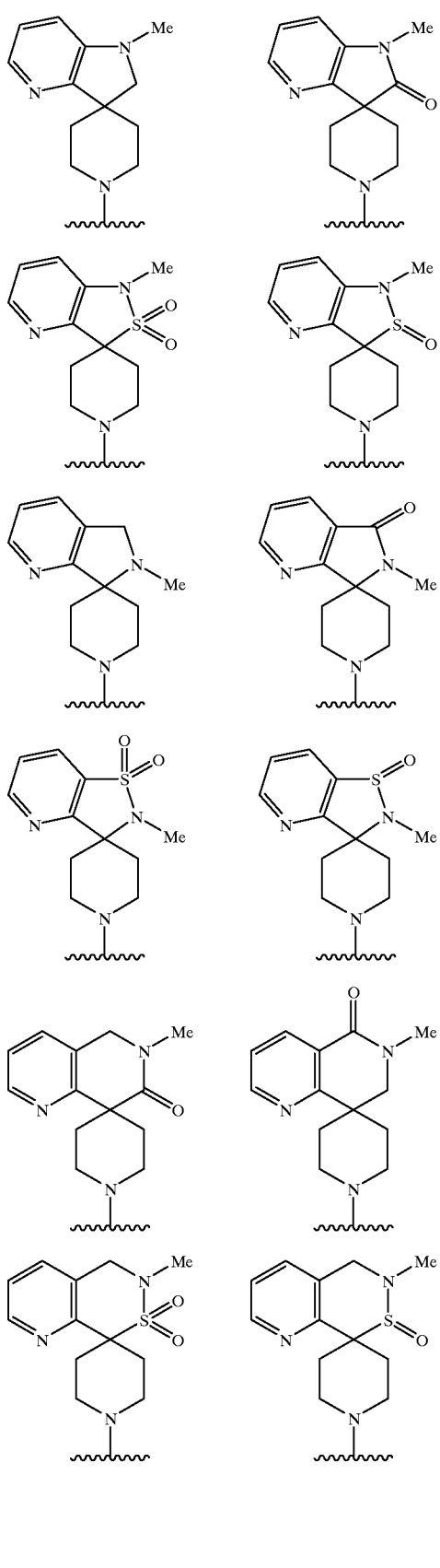

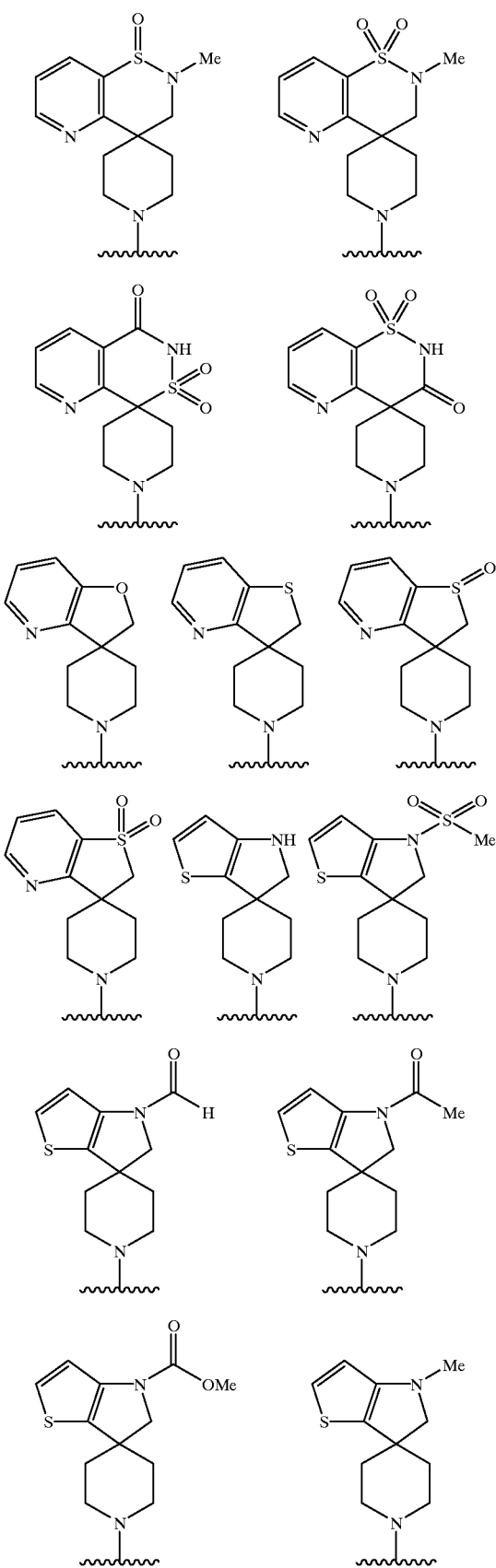
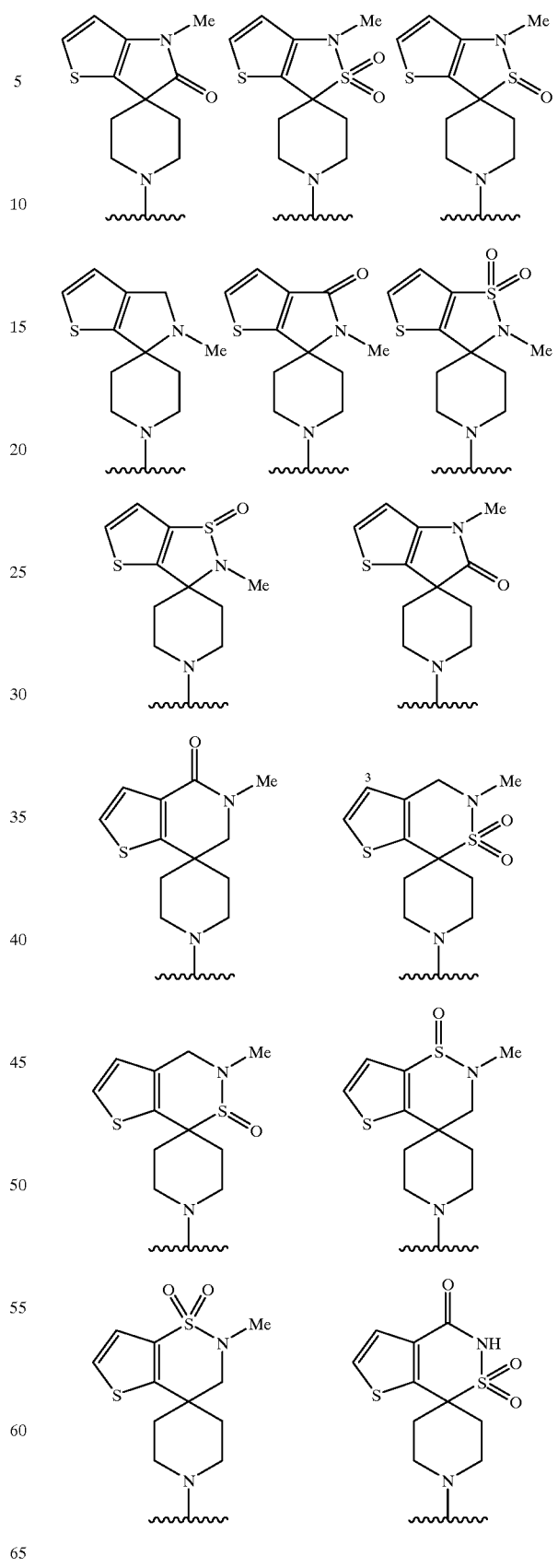

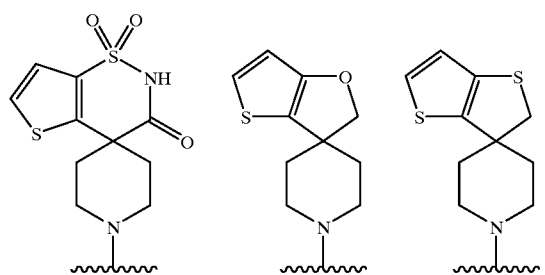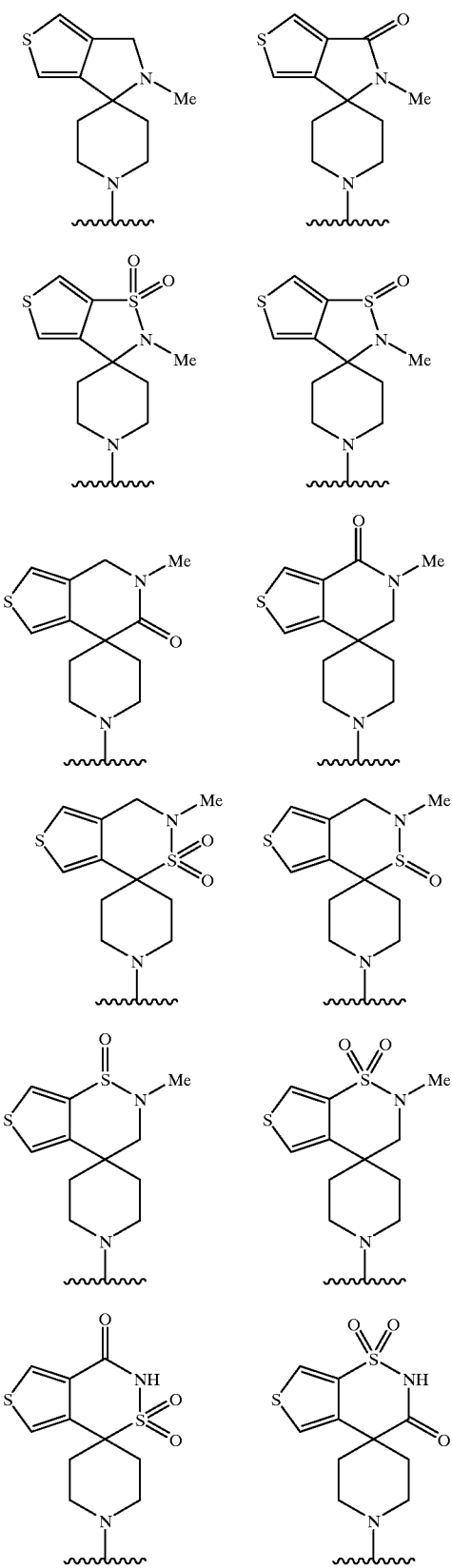

-continued
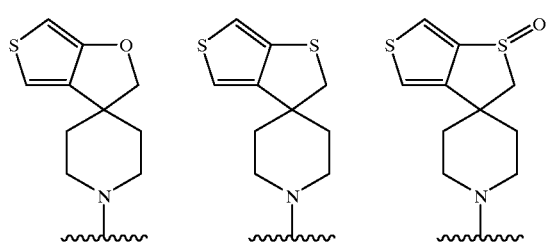
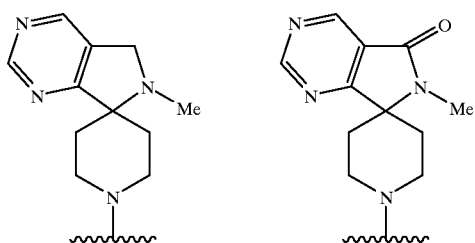
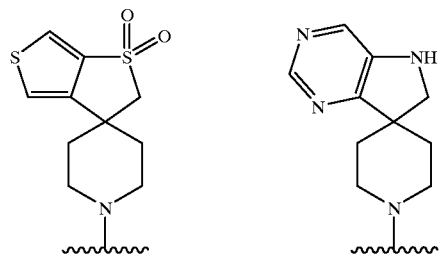
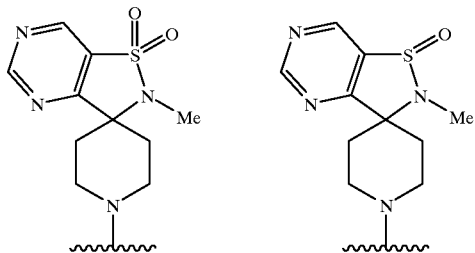
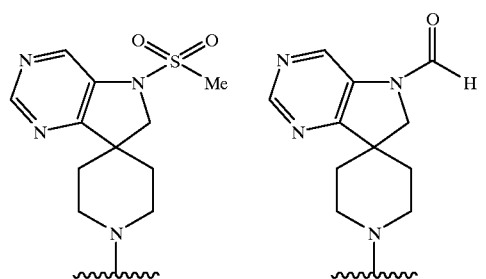
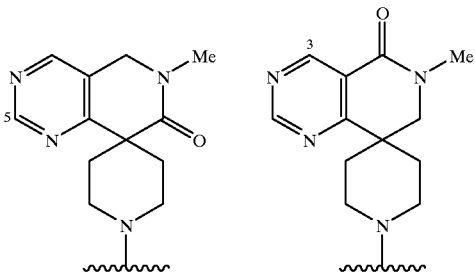
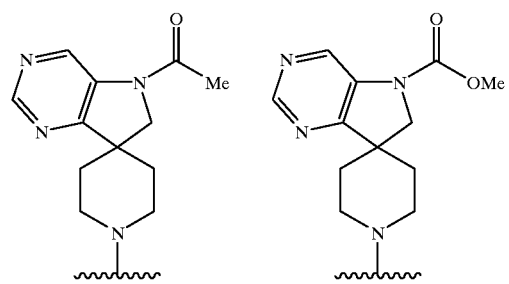
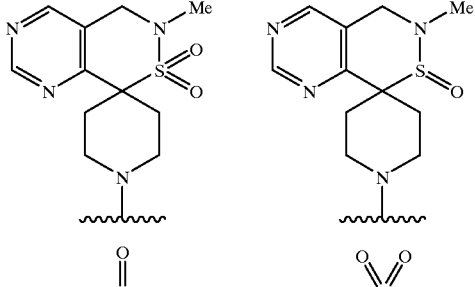
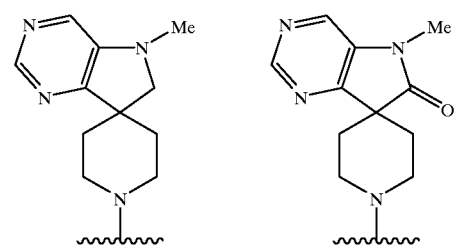
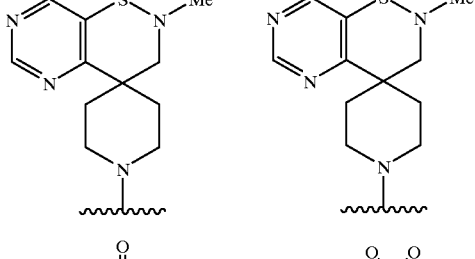
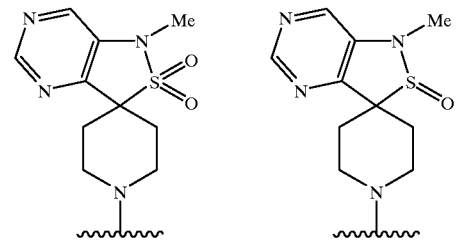
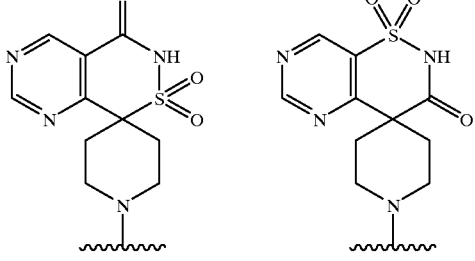

-continued

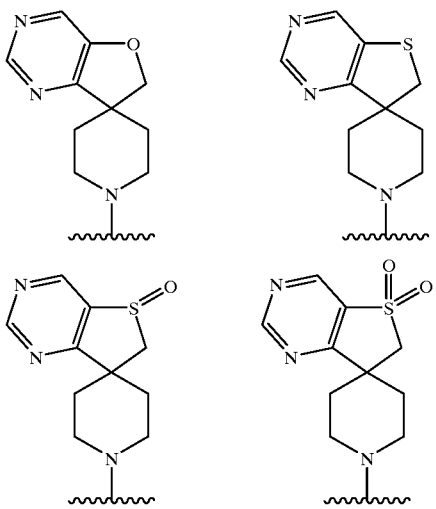

As is clear from the examples and schemes, the designation:

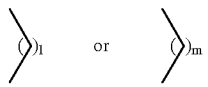

in formula I is interchangeable with $(CH_2)_l$ or $(CH_2)_m$ respectively. As appreciated by those of skill in the art, halo as used herein are intended to include chloro, fluoro, bromo and iodo.

Exemplifying the invention are the compounds of the examples including the group consisting of (a) 1'-(3-(S)-(3,4-dichlorophenyl)-4-(t-butoxycarbonyl (methylamino))butyl)-1-methanesulfonyl-spiro(indoline-3,4'-piperidine);

(b) 1'-(3-((S)-(3,4-dichlorophenyl))-4-(N-(3,5-dimethylbenzoyl)(methylamino))butyl)-1-methanesulfonyl-spiro(indoline-3,4'-piperidine);

(c) 1'-(3-((S)-(3,4-dichlorophenyl))-4-(N-(benzoyl)(methylamino))butyl)-1-methanesulfonyl-spiro(indoline-3,4'-piperidine);

(d) 1'-(3-((S)-(3,4-dichlorophenyl))-4-(N-(3,5-bistrifluoromethylbenzoyl)(methylamino))butyl)-1-methanesulfonyl-spiro(indoline-3,4'-piperidine);

(e) 1'-(3-((S)-(3,4-dichlorophenyl))-4-(N-(3-methylbenzoyl)(methylamino))butyl)-1-methanesulfonyl-spiro(indoline-3,4'-piperidine);

(f) 1'-(3-((S)-(3,4-dichlorophenyl))-4-(N-(3-chlorobenzoyl)(methylamino))butyl)-1-methanesulfonyl-spiro(indoline-3,4'-piperidine);

(g) 1'-(3-((S)-(3,4-dichlorophenyl))-4-(N-(3-trifluoromethylbenzoyl)(methylamino))butyl)-1-methanesulfonyl-spiro(indoline-3,4'-piperidine);

(h) 1'-(3-((S)-(3,4-dichlorophenyl))-4-(N-(3,5-dichlorobenzoyl)(methylamino))butyl)-1-methanesulfonyl-spiro(indoline-3,4'-piperidine);

(i) 1'-(3-((S)-(3,4-dichlorophenyl))-4-(N-(3-trifluoromethyl-phenylacetyl)(methylamino))butyl)-1-methanesulfonyl-spiro(indoline-3,4'-piperidine);

(j) 1'-(3-((S)-(3,4-dichlorophenyl)-4-(N-(3-isopropyloxy-phenylacetyl)(methylamino))butyl)-1-methanesulfonyl-spiro(indoline-3,4'-piperidine);

(k) 1'-(3-((S)-(3,4-dichlorophenyl))-4-(N-(benzenesulfonyl)(methylamino))butyl)-1-methanesulfonyl-spiro(indoline-3,4'-piperidine);

(l) 1'-(3-((S)-(3,4-dichlorophenyl))-4-(N-(3,5-dimethylbenzoyl)(methylamino))butyl)-1-benzyoxycarbonyl-spiro(indoline-3,4'-piperidine);

(m) 1'-(3-((S)-(3,4-dichlorophenyl))-4-(N-(3,5-dimethylbenzoyl)(methylamino))butyl)-spiro(indoline-3,4'-piperidine);

(n) 1'-(3-((S)-(3,4-dichlorophenyl))-4-(N-(3,5-dimethylbenzoyl)(methylamino))butyl)-1-propionyl-spiro(indoline-3,4'-piperidine);

(o) 1'(3-((S)-(3,4-dichlorophenyl))-4-(N-(3,5-dimethylbenzoyl)(methylamino))butyl)-1-formyl-spiro(indoline-3,4'-piperidine);

(p) 1'-(3-((S)-(3,4-dichlorophenyl))-4-(N-(3,5-dimethylbenzoyl)(methylamino))butyl)-1-t-butylcarbonyl-spiro(indoline-3,4'-piperidine);

(q) 1'-(3-((S)-(3,4-dichlorophenyl))-4-(N-(3,5-dimethylbenzoyl)(methylamino))butyl)-1-methylaminocarbonyl-spiro(indoline-3,4'-piperidine);

(r) 1'(3-((S)-(3,4-dichlorophenyl))-4-(N-(3,5-dimethylbenzoyl)(methylamino))butyl)-1-ethoxycarbonyl-spiro(indoline-3,4'-piperidine);

(s) 1'(3-((S)-(3,4-dichlorophenyl))-4-(N-(3,5-dimethylbenzoyl)(methylamino))butyl)-1-ethanesulfonyl-spiro(indoline-3,4'-piperidine);

(t) 1'(3-((S)-(3,4-dichlorophenyl))-4-(N-(3,5-dimethylbenzoyl)(methylamino))butyl)-1-1-propanesulfonyl-spiro(indoline-3,4'-piperidine);

(u) 1'(3-((S)-(3,4-dichlorophenyl))-4-(N-(3,5-dimethylbenzoyl)(methylamino))butyl)-1'-methyl-1-methanesulfonyl-spiro-indoline-3,4'-piperidinium iodide;

(v) 1'-(3-(S)-(3,4-dichlorophenyl)-4-(N-(R or S)-(3-methylbenzoyl)(methylamino))pentyl)-1-methanesulfonyl-spiro(indoline-3,4'-piperidine);

(w) 1'-(3-(S)-(3,4-dichlorophenyl)-4-(N-(R or S)-(3,5-bis(trifluoromethyl)benzoyl)(methylamino))pentyl)-1-methanesulfonyl-spiro(indoline-3,4'-piperidine);

(x) 1'-(3-(S)-(3,4-dichlorophenyl)-4-(N-(R or S)-(3,5-dimethylbenzoyl)(methylamino))pentyl)-1-methanesulfonyl-spiro(indoline-3,4'-piperidine);

(y) 1'-(3-(S)-(3,4-dichlorophenyl)-4-(N-(R or S)-(3,5-dichlorobenzoyl)(methylamino))pentyl)-1-methanesulfonyl-spiro(indoline-3,4'-piperidine);

(aa) 1'-(3-((S)-(3,4-dichlorophenyl))-4-(N-(3,5-difluorobenzoyl)(methylamino))butyl)-1-methanesulfonyl-spiro(indoline-3,4'-piperidine);

(ab) 1'-(3-((S)-(3,4-dichlorophenyl))-4-(N-(3-fluoro-5-(trifluoromethyl)benzoyl)(methylamino))butyl)-1-methanesulfonyl-spiro(indoline-3,4'-piperidine);

(ac) 1'-(3-((S)-(3,4-dichlorophenyl))-4-(N-(1-naphthoyl)(methylamino))butyl)-1-methanesulfonyl-spiro(indoline-3,4'-piperidine);

(ad) 1'-(2-((S)-(3,4-dichlorophenyl))-1-(N-(2-chlorophenylsulfonyl)-(methylamino))-4-butyl)-1-methylsulfonyl-spiro(indoline-3,4'-piperidine);

(ae) 1'-(2-((S)-(3,4-dichlorophenyl))-1-(N-(3-chlorophenylsulfonyl)-(methylamino))-4-butyl)-1-methylsulfonyl-spiro(indoline-3,4'-piperidine);

(af) 1'-(2-((S)-(3,4-dichlorophenyl))-1-(N-(4-chlorophenylsulfonyl)-(methylamino))-4-butyl)-1-methylsulfonyl-spiro(indoline-3,4'-piperidine);

(ag) 1'-(2-((S)-(3,4-dichlorophenyl))-1-(N-(3,5-dichlorophenylsulfonyl)-(methylamino))-4-butyl)-1-methylsulfonyl-spiro(indoline-3,4'-piperidine);

(ah) 1'-(3-((S)-(3,4-dichlorophenyl))-4-(N-(3-fluoro-5-(trifluoromethyl)benzoyl)(methylamino))butyl)-1-acetyl-spiro(indoline-3,4'-piperidine);

(ai) 1'-(3-((S)-(3,4-dichlorophenyl))-4-(N-(3,5-dimethylbenzoyl)(methylamino))butyl)-1-acetyl-spiro(indoline-3,4'-piperidine);

(aj) 1'-(3-((S)-(3,4-dichlorophenyl))-4-(N-(3-bromo-5-methylbenzoyl)(methylamino))butyl)-1-methanesulfonyl-spiro(indoline-3,4'-piperidine);

(ak) 1'-(3-((S)-(3,4-dichlorophenyl))-4-(N-(3,5-dimethylbenzoyl)(methylamino))butyl)-1-(2-aminoacetyl)-spiro(indoline-3,4'-piperidine);

(al) 1'-(3-((S)-(3,4-dichlorophenyl))-4-(N-(3,5-dimethylbenzoyl)(methylamino))butyl)-1-methyl-spiro(indol-2-one-3,4'-piperidine);

(am) 1'-(3-((S)-(3,4-dichlorophenyl))-4-(N-(3,5-dichlorobenzoyl)(methylamino))butyl)-1-methyl-spiro(isoindol-1-one-3,4'-piperidine);

(an) 1'-(3-((S)-(3,4-dichlorophenyl))-4-(N-(3,5-dimethylbenzoyl)(methylamino))butyl)-spiro(2-oxo-tetrahydroquinoline-4,4'-piperidine); and (ao) 1'-(3-((S)-(3,4-dichlorophenyl))-4-(N-(3,5-dichlorobenzoyl)(methylamino))butyl)-1-methyl-spiro(2-oxo-tetrahydroquinoline-4,4'-piperidine).

In an alternative embodiment the above compounds may be co-administered with a β2-agonist such as Bambuterol, U.S. Pat. No. 4,419,364 issued to Draco on Dec. 6, 1983; Bitolterol mesylate, U.S. Pat. No. 4,138,581 issued to Sterling Feb. 6, 1979; Carbuterol, U.S. Pat. No. 3,763,232 issued to SmithKline Oct. 2, 1973; Clenbuterol, U.S. Pat. No. 3,536,712 issued to Boehringer Ingelheim Oct. 27, 1970; Dopexamine, U.S. Pat. No. 4,645,768 issued to Fisons Feb. 24, 1987; Formoterol, U.S. Pat. No. 3,994,974 issued to Yamanouchi Nov. 30, 1976; Mabuterol, U.S. Pat. No. 4,119,710 issued to Boehringer Ingelheim Oct. 10, 1978; Pirbuterol hydrochloride U.S. Pat. No. 3,700,681 issued to Pfizer Oct. 24, 1972; Procaterol hydrochloride U.S. Pat. No. 4,026,897 issued to Otsuka May 31, 1977; Ritodrine hydrochloride U.S. Pat. No. 3,410,944 issued to North American Philips Nov. 12, 1968; Brosaterol, U.S. Pat. No. 4,276,299 issued to Zambon Jun. 30, 1981 and U.S. Pat. No. 4,520,200 issued to Zambon May 28, 1985; Cimaterol, U.S. Pat. No. 4,407,819 issued to American Cyanamid Oct. 4, 1983; Docarpamine, U.S. Pat. No. 4,228,183 issued to Tanabe Oct. 14, 1980; Salmeterol, U.S. Pat. No. 4,992,474 issued to Glaxo Feb. 21, 1991 and U.S. Pat. No. 5,091,422 issued to Glaxo Feb. 25, 1992.

The compounds of formula I are particularly useful in the treatment of diseases or conditions that are advantageously treated by concomitant antagonism of both NK1 and NK2 receptors or NK1, NK2 and NK3 receptors. These diseases include neuropathy, such as diabetic or peripheral neuropathy and chemotherapy-induced neuropathy; asthma; osteoarthritis; rheumatoid arthritis; and migraine.

In a second alternative embodiment the compounds of formula I may be co-administered with another NK1 or NK2 antagonist such as those described in Appln No. DO-139125, filed Jun. 8, 1978, Pub. Dec. 12, 1979; Appln No. EP-82568, filed Dec. 22, 1981, Pub. Jun. 29, 1983; Appln No. EP-490379, filed Dec. 13, 1990, Pub. Jun. 17, 1992; Appln No. EP-353732, filed Aug. 5, 1988, Pub. Feb. 7, 1990; Appln No. EP-161007, filed Jan. 13, 1984, Pub. Nov. 13, 1985; Appln No. EP-385-43, filed Feb. 28, 1989, Pub. Sep. 5, 1990; Appln No. WO8301251, filed Oct. 9, 1981, Pub. Apr. 14, 1983; Appln No. BE-894602, filed Oct. 9, 1981, Pub. Jan. 31, 1983; Appln No. DE3205991, filed Feb. 19, 1982, Pub. Sep. 1, 1983; Appln No. EP-327009, filed Feb. 2, 1988, Pub. Aug. 9, 1989; Appln No. EP-336230, filed Apr. 5, 1988, Pub. Oct. 11, 1989; Appln No. 394989, filed Apr. 28, 1989, Pub. Oct. 31, 1990; Appln No. AU9068010, filed Dec. 22, 1989, Pub. Jun. 27, 1991; Appln No. EP-482539, filed Oct. 24, 1990, Pub. Apr. 29, 1992; Appln No. EP-443132, filed Dec. 10, 1990, Pub. Aug. 28, 1991; Appln No. EP-498069, filed Dec. 21, 1990, Pub. Aug. 12, 1992; Appln No. WO9222569, filed Jun. 19, 1991, Pub. Dec. 23, 1992; Appln No. JO4297492, filed Oct. 24, 1991, Pub. Oct. 21, 1992; U.S. Pat. No. 4,997,853, filed Dec. 2, 1988, Pub. Mar. 5, 1991; Appln No. EP-272929, filed Dec. 24, 1986, Pub. Jun. 29, 1988; Appln No. EP-360390, filed Jul. 25, 1988, Pub. Mar. 28, 1990; U.S. Pat. No. 3,862,114, filed Nov. 22, 1971, Pub. Jan. 21, 1975; Appln No. EP-219258, filed Sep. 30, 1985, Pub. Apr. 22, 1987, U.S. Pat. No. 4,742,156, filed Sep. 30, 1985, Pub. May 3, 1988; Appln No. EP-401177, filed May 29, 1989, Pub. Dec. 5, 1990; Appln No. WO9202546, filed Aug. 3, 1990, Pub. Feb. 20, 1992; Appln No. EP-176436, filed Sep. 26, 1984, Pub. Apr. 2, 1986; U.S. Pat. No. 4,680,283, filed Sep. 26, 1984, Pub. Jul. 14, 1987; Appln No. WO9220661, filed May 22, 1991, Pub. Nov. 26, 1992; Appln No. EP-520555, filed Jun. 24, 1991, Pub. Dec. 30, 1992; Appln No. EP-347802, filed Jun. 20, 1988, Pub. Dec. 27, 1989; Appln No. EP-412542, filed Aug. 10, 1989, Pub. Feb. 13, 1991; Appln No. WO9005729, filed Nov. 23, 1988, Pub. May 31, 1990; Appln No. WO9005525, filed Nov. 23, 1988, Pub. May 31, 1990; Appln No. EP-436334, filed Jan. 4, 1990, Pub. Jul. 10, 1991; Appln No. WO9118878, filed May 31, 1990, Pub. Dec. 12, 1991; Appln No. WO9118899, filed Jun. 1, 1990, Pub. Dec. 12, 1991; Appln No. WO9201688, filed Jul. 23, 1990, Pub. Feb. 6, 1992; Appln No. WO9206079, filed Sep. 28, 1990, Pub. Apr. 16, 1992; Appln No. WO9212152, filed Jan. 3, 1991, Pub. Jul. 23, 1992; Appln No. WO9212151, filed Jan. 10, 1991, Pub. Jul. 23, 1992; WO9215585, filed Mar. 1, 1991, Pub. Apr. 29, 1992; Appln No. WO022-676, filed May 22, 1991, Pub. Nov. 26, 1992; Appln No. WO9221677, filed May 31, 1991, Pub. Dec. 10, 1992; Appln No. WO9300331, filed Jun. 20, 1991, Pub. Jun. 7, 1993; Appln No. WO9300330, filed Jun. 21, 1991, Pub. Jan. 7, 1993; Appln No. WO9109844, filed Jul. 11, 1991, Pub. Jul. 11, 1991; Appln No. EP-429366, filed Nov. 23, 1989, Pub. May 29, 1991; Appln No. EP-430771, filed Nov. 23, 1989, Pub. Jun. 5, 1991; Appln No. EP-514274, filed May 17, 1991, Pub. Nov. 19, 1992; Appln No. EP-514276, filed May 17, 1991, Pub. Nov. 19, 1992; Appln No. EP-514275, filed May 17, 1991, Pub. Nov. 19, 1992; Appln No. EP-514273, filed May 17, 1991, Pub. Nov. 19, 1992; Appln No. EP-428434, filed Nov. 6, 1989, Pub. May 22, 1991; Appln No. EP-474561, filed May 9, 1990, Pub. Mar. 11, 1992; Appln No. EP-512901, filed May 3, 1991, Pub. Nov. 11, 1992; Appln No. EP-512902, filed May 3, 1991, Pub. Nov. 11, 1992; Appln No. EP-515240, filed May 3, 1991, Pub. Nov. 25, 1992; U.S. Pat. No. 4,472,305, filed May 17, 1983, Pub. Sep. 18, 1984; U.S. Pat. No. 4,839,465, filed Jan. 20, 1987, Pub. Jun. 13, 1989; Appln No. EP-101929, filed Jul. 28, 1982, Pub. Mar 7, 1984; Appln No. WO9102745, filed Aug. 16, 1989, Pub. Mar. 7, 1991; U.S. Pat. No. 3,912,711, filed Jul. 3, 1972, Pub. Oct. 14, 1975; U.S. Pat. No. 4,059, 693, filed Jun. 11, 1976, Pub. Nov. 22, 1977; U.S. Pat. No. 4,481,139, filed Apr. 13, 1983, Pub. Nov. 6, 1984; U.S. Pat. No. 7,358,073, filed Oct. 24, 1988, Pub. Dec. 19, 1989; U.S. Pat. No. 7,261,627, filed Oct. 24, 1988, Pub. Mar. 7, 1989, which are hereby incorporated by reference.

The compounds of formula I are useful in the prevention and treatment of a wide variety of clinical conditions (as detailed in this specification) which are characterized by overstimulation of the tachykinin receptors, in particular NK1, NK2 and NK3.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK1, NK2 and NK3.

The compounds of the present invention are particularly useful in the treatment of pain or nociception and/or inflammation and disorders associated therewith such as, for example: neuropathy, such as diabetic or peripheral neuropathy and chemotherapy-induced neuropathy; asthma; osteoarthritis; rheumatoid arthritis; and migraine.

For the treatment of any of these diseases compounds of Formula I may be administered orally, topically, parenterally, ICV, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.001 to 25 mg/kg per day, about 0.005 to 10 mg/kg per day, or about 0.005 to 5 mg/kg per day. Within this range the dosage may be 0.005 to 0.05, 0.05 to 0.5 or 0.5 to 5.0 mg/kg per day. The compounds may be administered on a regimen of 1 to 4 times per day, preferably once or twice per day.

Tachykinin Antagonism Assay

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 $\mu$g of the plasmid DNA into 10 million COS cells was achieved by electroporation in 800 $\mu$l of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay. Similar methods were used to express the NK2 receptor.

B. Stable Expression in CHO

To establish a stable cell line expressing the cloned human NK1R, the cDNA was subcloned into the vector pRcCMV (INVITROGEN). Transfection of 20 $\mu$g of the plasmid DNA into CHO cells was achieved by electroporation in 800 $\mu$l of transfection buffer suplemented with 0.625 mg/ml Herring sperm DNA at 300 V and 950 uF using the IBI GENEZAPPER (IBI). The transfected cells were incubated in CHO media (10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)) in 5% $CO_2$ at 37° C. until colonies were visible. Each colony was separated and propagated. The cell clone with the highest number of human NK1R was selected for subsequent applications such as drug screening.

Similar methods were used to express the human NK2 receptor.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.02 mg/ml BSA, 0.01 mM phosphoramidon) such that 200 $\mu$l of the cell suspension would give rise to about 10,000 cpm of specific $^{125}$I-SP binding (approximately 50,000 to 200,000 cells). In the binding assay, 500 ul of cells were added to a tube containing 20 $\mu$l of 1.5 to 0.25 nM of $^{125}$-SP and 5 $\mu$l of unlabeled substance P or any other test compound in DMSO. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. A similar assay was used for NK2 except $^{125}$I-NKA was used as the ligand.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter. Similar methods were used to assess antagonism at the NK2 receptor, except NKA was used as the stimulating agonist.

The compounds of of Formula I as Exemplified in the EXAMPLES below have been found to displace radioactive ligand for the NK-1 receptor at a concentration range of 0.01 nM to 1.0 μM, for the NK-2 receptor, 0.01 nM to 5 μM, and for the NK-3 receptor, 1.0 nM to 10 μM.

Several methods for preparing the compounds of this invention are illustrated in the following Schemes and Examples.

The compounds of the present invention are prepared by alkylating azacycle 1, in which $R_1$=H, under appropriate conditions (Scheme 1). The required azacycle starting materials are prepared using methods described in the literature; such as described in Ong, H. H. et al, Journal of Medicinal Chemistry, 1983,26, 981–986, and Nargund, R. et al, U.S. Ser. No. 08/147,226 (Nov. 3, 1993), EP 93309867.5 hereby encorporated by reference. None of the compounds in these references are claimed to be neurokinin antagonists.

Thus, azacycle 1 ($R_1$=H) is combined with the appropriate aldehyde and the intermediate imine is reduced to the tertiary amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Hale, J. J.; Finke, P. E.; MacCoss, M. *Bioorganic & Medicinal Chemistry Letters* 1993, 3, 319–322.

In an alternative embodiment of the present invention, azacycle 1 ($R_1$=H) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 3rd ed., John Wiley & Sons, New York, pp. 382–384 (1985), or alkyl sulfonate ester using methods described in March J. "Advanced Organic Chemistry", 3rd ed., John Wiley & Sons, New York, p. 444 (1985).

In an alternative embodiment of the present invention, 1 ($R_1$=H) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I ($R_1$=H). The product amide can in and of itself be a neurokinin antagonist or can be reduced with a strong reducing agent, such as diborane or lithium aluminum hydride, to give the tertiary amine.

Optionally, compound 1 formed in the alkylation step may be further modified in subsequent reactions. In one illustration of such an approach, the aldehyde fragment contained a t-butoxycarbonylamino group (Example 2). After reductive amination, the t-butoxycarbonyl protecting group is removed by treatment with a strong acid such as trifluoroacetic acid or formic acid and the resulting amine is acylated to furnish the desired compounds (Example 3). Alternatively, the protecting group may also be present in the azacycle portion as illustrated with a benzyloxycarbonyl group in Example 6. Thus an azacycle containing a benzyloxycarbonylindoline (prepared in Example 4) is alkylated with an aldehyde in the presence of a reducing agent. Next, the protecting group is removed to liberate a free amine (Example 7) and the amine is further reacted to provide additional analogs (Example 8).

SCHEME 1

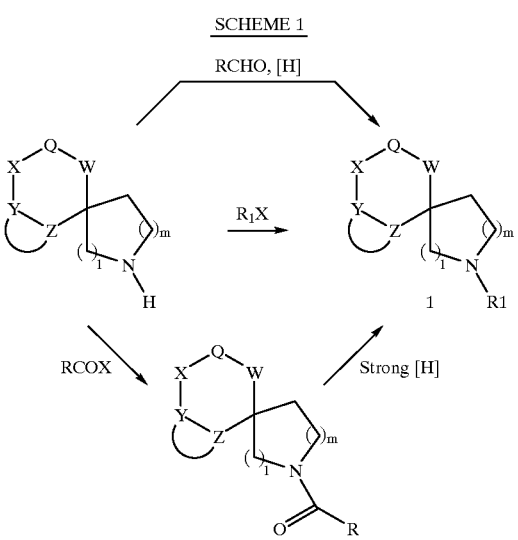

In an alternative embodiment of the present invention, the allyl acid 2 (described in Hale et al; see above) can be converted into the N-methyl methoxy amide 3, which is then treated with an alkyl or aryl metal reagent, for example methyllithium or butyllithium, to provide the ketone 4 (Scheme 2). The ketone can be converted into an imine which can then be reduced to secondary amine 5 chemically, (e.g using sodium cyanoborohydride or sodium borohydride), or catalytically (e.g. using hydrogen and palladium on carbon or Raney nickel catalyst). Acylation under standard conditions, for example with an acid chloride, provides amide 6. The allyl group in 6 can be oxidatively cleaved to aldehyde 7 with osmium tetroxide followed by sodium periodate or with ozone at low temperature. Reductive amination of aldehyde 7 with azacycle 1 can then be carried out under the conditions described above.

Substituted spiro(indoline-3,4'-piperidine) derivatives can be prepared as shown in Scheme 3 starting from the appropriately substituted phenylhydrazines. Following the Fischer indole reaction and reduction of the intermediate imine with a mild reducing agent such as sodium borohydride, the indoline nitrogen can be reacted with an electrophile such as an acyl chloride or a sulfonyl chloride. The protecting group on the piperidine nitrogen, for example a benzyloxycarbonyl group, can be removed by treatment with hydrogen in the presence of palladium on carbon or by exposure to trimethylsilyl iodide, to give the deprotected substituted spiro (indoline-3,4'-piperidine).

SCHEME 2
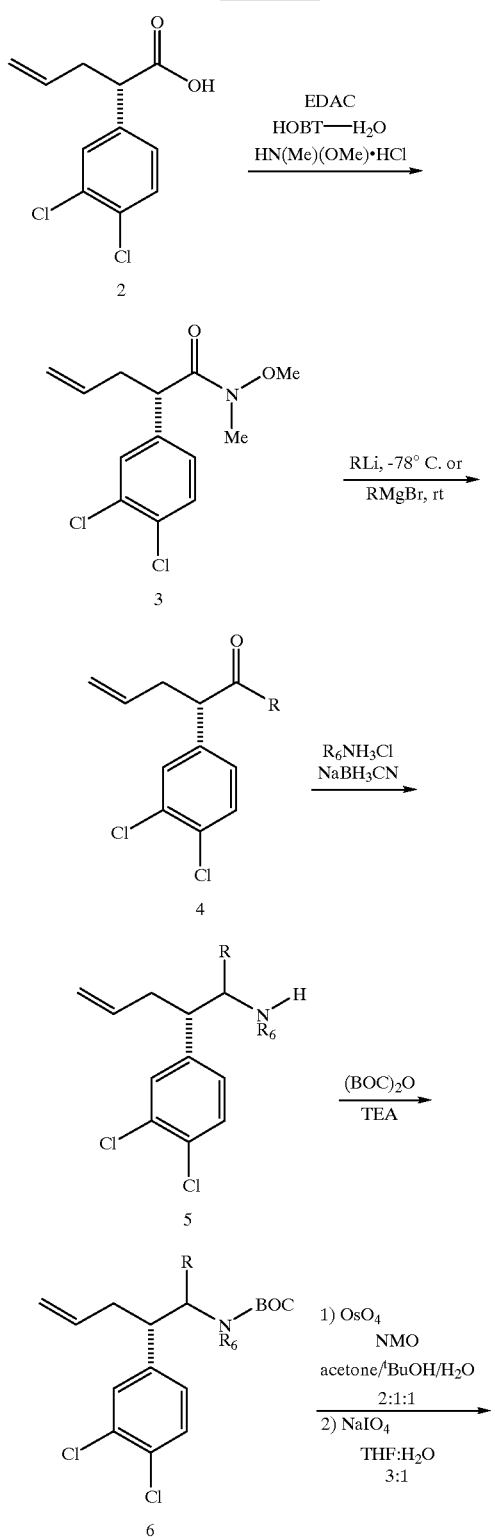
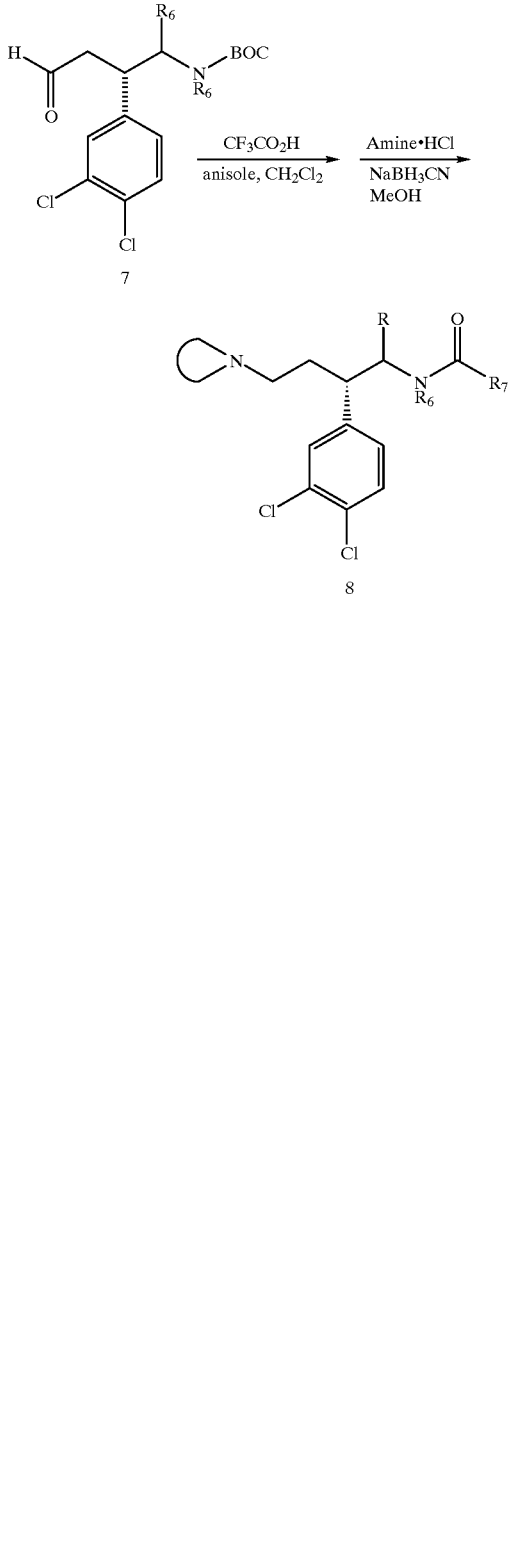

SCHEME 3

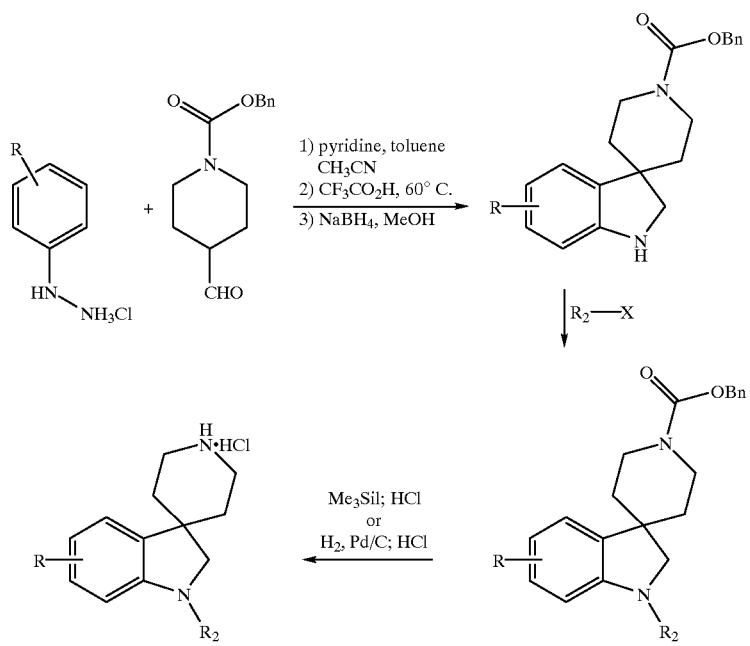

Preparation of spiro (2,3-dihydrobenzothiophene-3,4'-piperidine) derivatives is shown in Scheme 4. Reaction of N-Boc protected 4-piperidone with the lithium salt of methyl phenyl sulfoxide followed by base-mediated elimination-rearrangement and basic cleavage provides the indicated allylic alcohol. The alcohol can be converted to the rearranged allylic chloride with thionyl chloride in toluene in the presence of 2,6-lutidine as a proton scavenger. Displacement of the chloride with functionalized 2-bromothiophenol provides the allylic sulfide, which can be cyclized under radical conditions to give the illustrated spiro(2,3-dihydrobenzothiophene-3,4'-piperidine). Cleavage of the t-butoxycarbonyl group under standard conditions, such as trifluoroacetic acid, then provides the desired spirocycle.

SCHEME 4

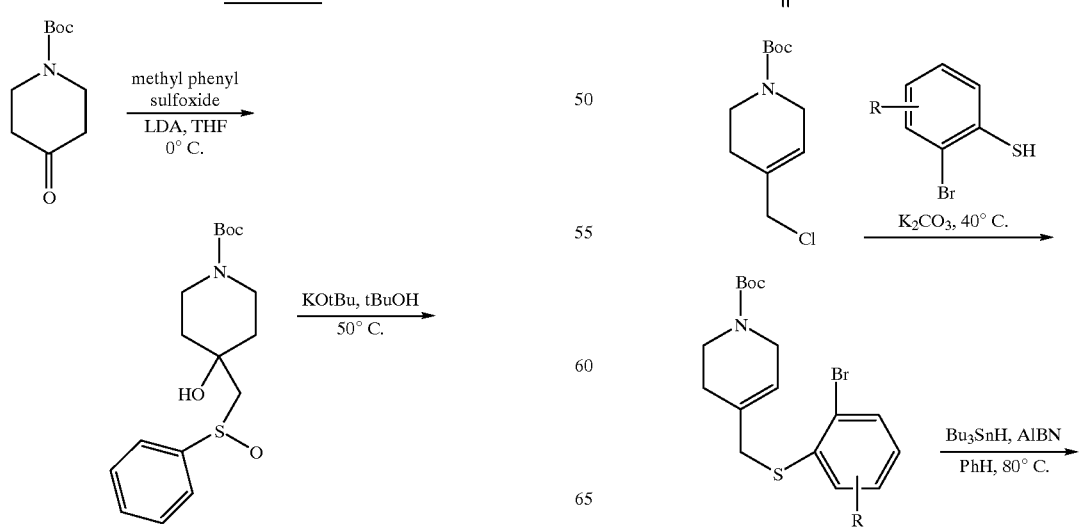

-continued

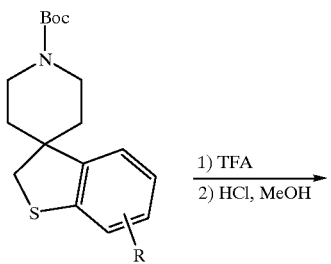

1) TFA
2) HCl, MeOH

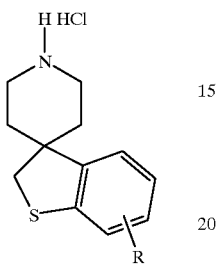

Spiro(2,3-dihydrobenzofuran-3,4'-piperidine) derivatives can be prepared as illustrated in Scheme 5. Treatment of an appropriately substituted ester of 2-fluorophenylacetate with mechlorethamine hydrochloride under basic conditions provides the piperidine product, which on treatment with a strong reducing agent such as lithium aluminum hydride produces the corresponding 4-(hydroxymethyl) compound. Cyclization with base provides the benzofuran derivative, and cleavage of the N-methyl group can then be carried out using 1-chloroethyl chloroformate or other suitable N-demethylating agents.

SCHEME 5

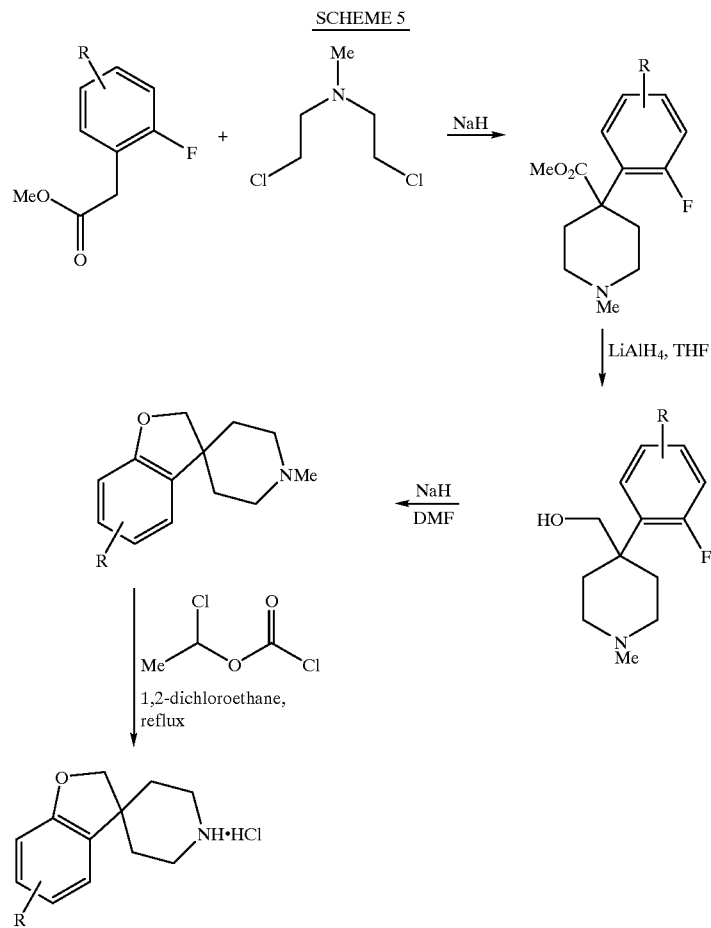

Compounds with alternate arrangements of the amide bond can be prepared as shown in Scheme 6. The illustrated acid can be homologated under Arndt-Eistert conditions to give the chain-extended acid, which can be derivatized under standard acylating conditions with, for example, an aniline derivative, to give the corresponding amide. Oxidative cleavage of the olefin with osmium tetroxide or ozone then provides the aldehyde intermediate suitable for coupling as described earlier.

7. A second Arndt-Eistert chain extension provides the illustrated heptenoic acid derivative, which after conversion into its N-methoxy-N-methyl amide, can be reacted with an aryl organometallic reagent, such as an aryl magnesium bromide, to provide the ketone. Routine oxidative cleavage then gives the desired aldehyde, which can be coupled with a spiro-piperidine derivative as described above.

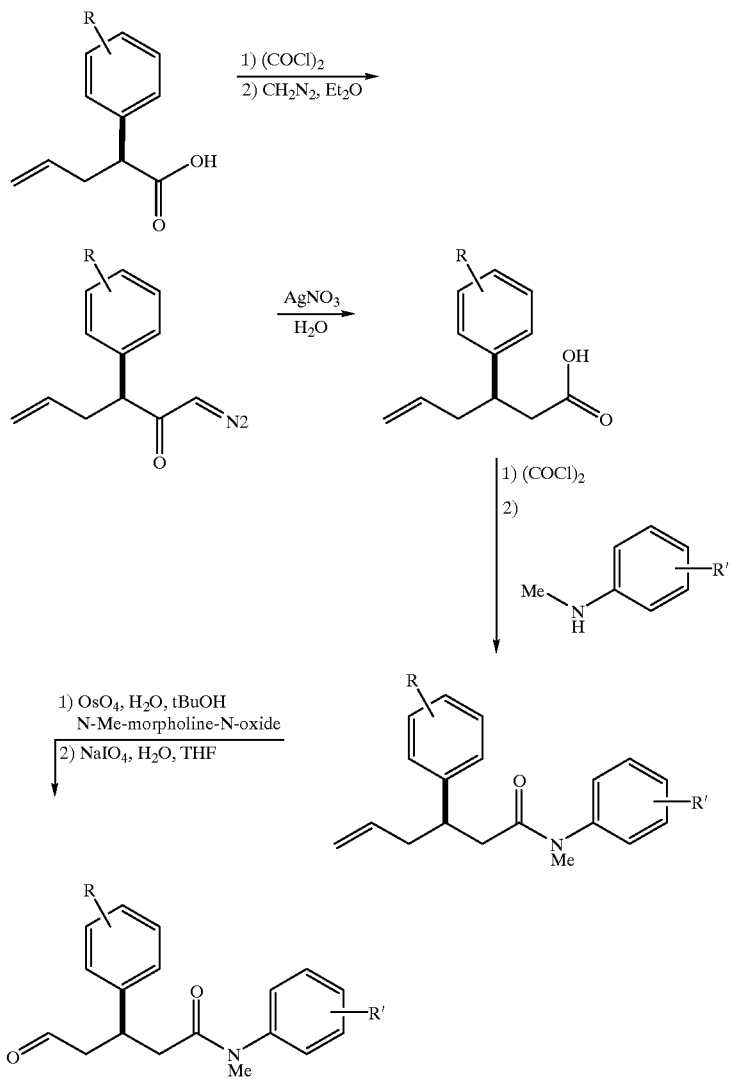

In addition, ketone derivatives can be prepared by an extension of the chemistry given above, as shown in Scheme

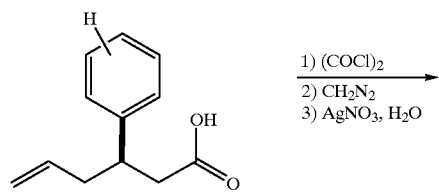

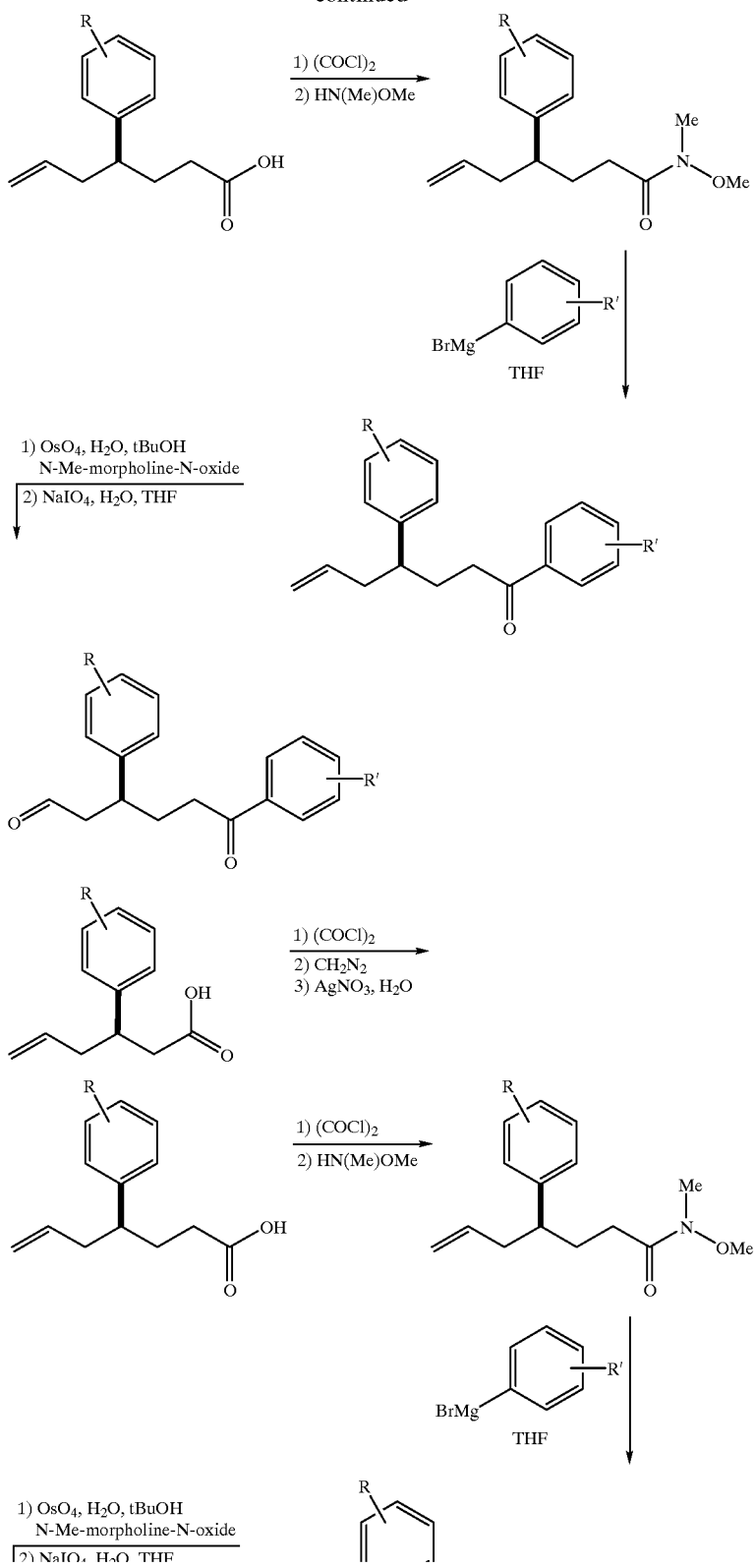

Alcohol containing antagonists can be prepared according to procedures given in Scheme 8. Formation of the N-methyl-N-methoxy amide of the indicated acid followed by oxidative cleavage of the olefin provides the intermediate aldehyde. Coupling with a spiro(indoline-3,4'-piperidine) derivative followed by addition of an organometallic reagent to the amide provides the illustrated ketone. Treatment with a hydride reducing agent, such as sodium borohydride, then yields the desired alcohol derivatives.

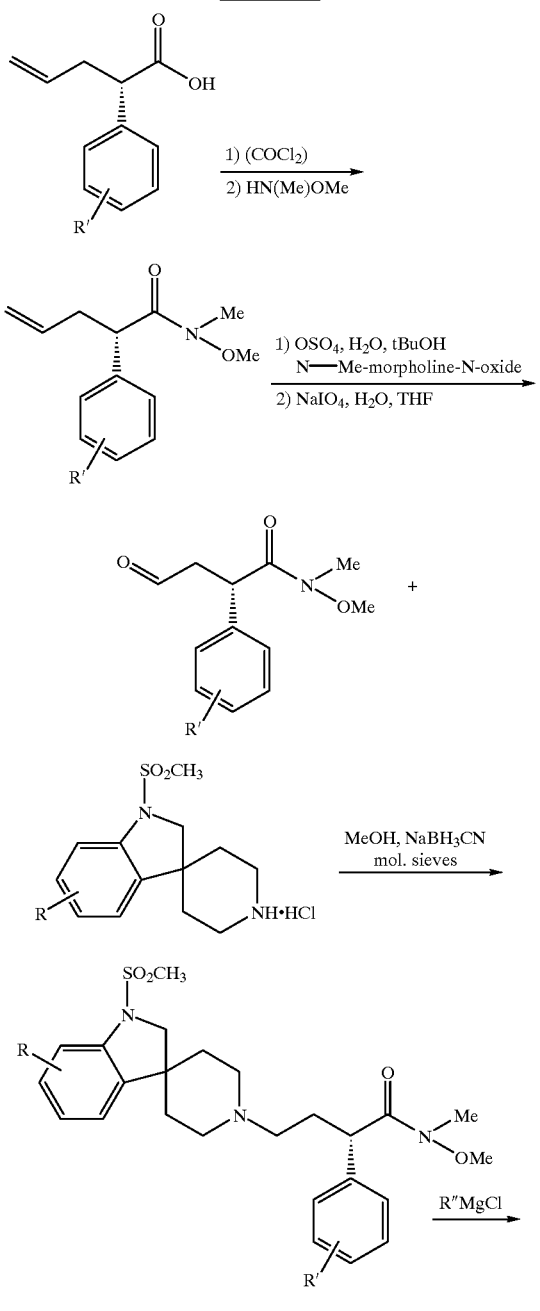

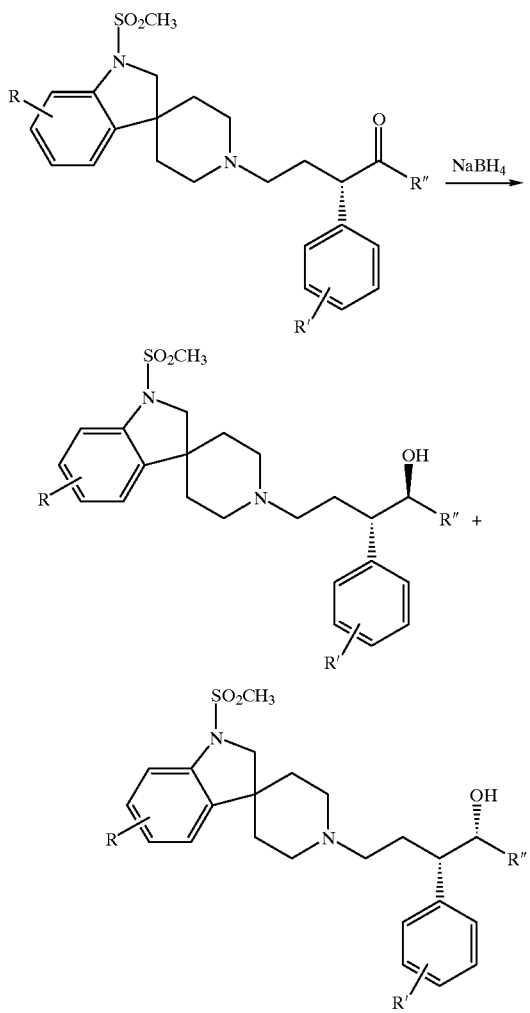

Formation of heterocycle substituted antagonists can be carried out according to the procedure given in Scheme 9 for substituted imidazoles. Reduction of the allyl acid with a strong reducing agent such as lithium aluminum hydride followed by in situ formation of the trifluoromethanesulfonate of the formed alcohol allows for displacement of the triflate with a nucleophile such as 2-phenylimidazole. Oxidative cleavage under standard conditions provides the indicated aldehyde which can then be coupled under the conditions described above to the appropriate spiro derivative.

SCHEME 9

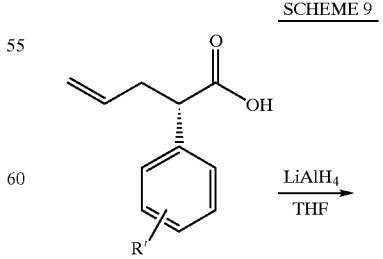

-continued

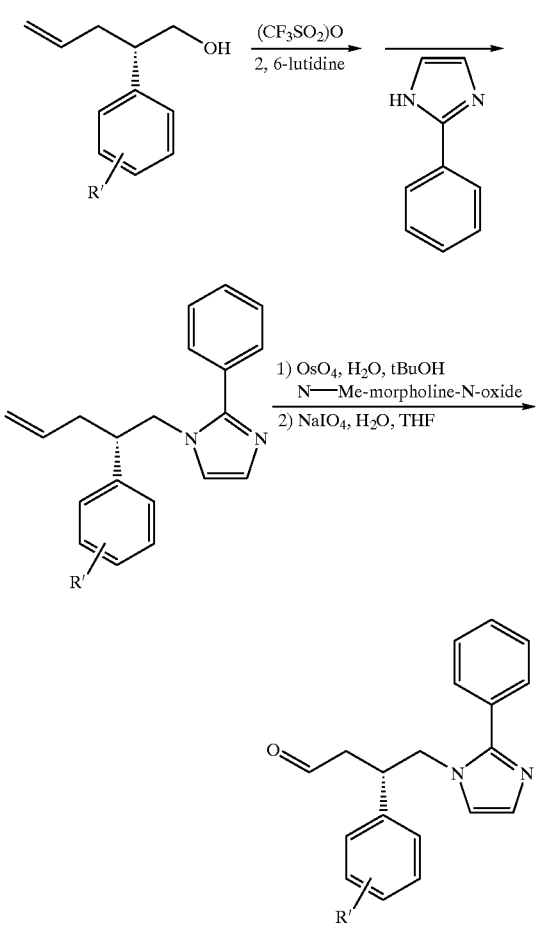

from the indicated spiro(2-oxoindane-3,4'-piperidine) (described in Claremon, D. A. et al, European Patent 0 431 943 943 A2, Evans, B. E. et al, U.S. Pat. No. 5,091,387, Davis, L. et al, U.S. Pat. No. 4,420,485, all of which are incorporated by reference, and Parham et al, *Journal of Organic Chemistry*, 41, 2628 (1976)), deprotection of the piperidine nitrogen is carried out by treatment with acid, for example trifluoroacetic acid, followed by protection as the trifluoroacetamide, and the product is exposed to hydrazoic acid in the presence of sulfuric acid. Heating of this mixture effects a Schmidt rearrangement, to provide both the tetrahydroquinoline and the tetrahydroisoquinoline derivatives. These spiro compounds can then be separated and coupled to functionalized aldehydes by the methodology given above.

SCHEME 10

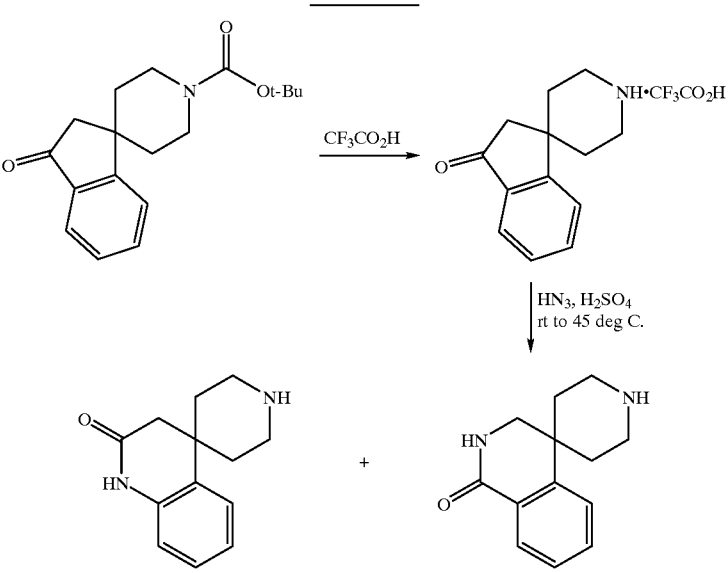

Spiro(2-oxo-1,2,3,4-tetrahydroquinoline-4,4'-piperidine) and spiro(1-oxo-1,2,3,4-tetrahydroisoquinoline-4,4'-piperidine) can be prepared as shown in Scheme 10. Starting Neurokinin antagonists with ether substituents can also be prepared by the route shown in Scheme 11. Thus, the allyl acid discussed earlier can be reduced to the corresponding alcohol with, for example, lithium aluminum hydride. This alcohol can be alkylated by a Williamson ether synthesis, by deprotonation with a strong base such as sodium hydride or sodium hexamethyldisilazide followed by reaction with a benzyl halide such as benzyl bromide. The product can be processed through the oxidative cleavage steps described earlier to provide the aldehyde, which can then be coupled with a spirocycle kunder reductive amination conditions or else by reduction to the corresponding alcohol and conversion to the bromide. The bromide can then be used to alkylate a spirocycle under the conditions detailed above.

SCHEME 11

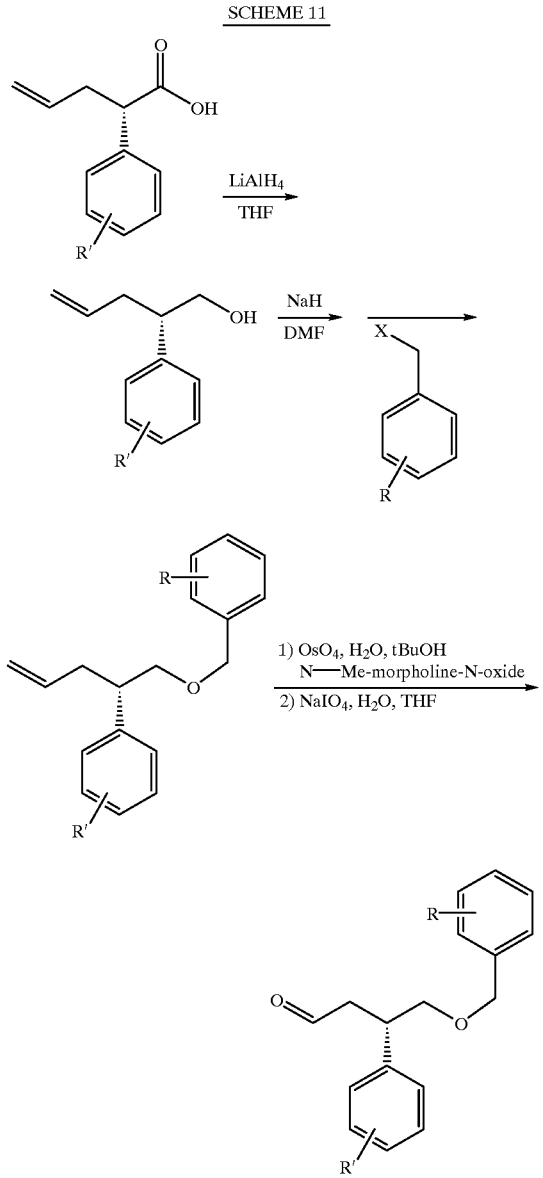

Accordingly in another aspect the invention encompasses a process of making compounds of formula I

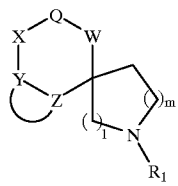

as defined above, comprising the steps of:
(a) reacting a compound of formula A

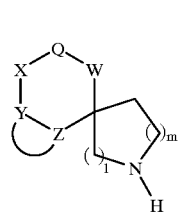

in a suitable solvent such as acetonitrile or dimethylacetamide with a compound of formula $R_1$—$X_1$ wherein $X_1$ is a leaving group such as bromo, chloro, tosyl or mesyl optionally in the presence of a suitable base such as trialkylamine; or (b) reacting a compound of formula A in a second suitable solvent such as methanol or ethanol with a compound of the formula R—CH(O), wherein R—$CH_2$ is $R_1$ as defined above, in the presence of a reducing agent such as sodium cyanoborohydride or hydrogen and a palladium on carbon catalyst; or (c) reacting a compound of formula A in a halocarbon solvent such as methylene chloride with a compound of the formula R—C(O)$X_2$ wherein $X_2$ is a suitable leaving group such as bromo or chloro in the presence of a suitable base such as trialkylamine, to yield a compound of formula I.

EXAMPLE 1

3-(S)-(3,4-Dichlorophenyl)-4-(N-(t-butoxycarbonyl) methylamino)butanal

A solution of 10 g (41 mmol) of 3-(S)-(3,4-dichlorophenyl)-4-methylamino-1-pentene in 100 mL of $CH_2Cl_2$ was cooled in an ice bath and treated with 5.8 mL (41 mmol) of triethylamine ($Et_3N$) and 9 g (41 mmol) of di-t-butyl dicarbonate. The cold bath was removed after 5 min and the stirring was continued for 1 h. The reaction mixture was diluted with $CH_2Cl_2$ and washed with water, 1.2 N HCl, saturated $NaHCO_3$ and brine. The solution was dried over $Na_2SO_4$ and concentrated to give 14.58 g of residual oil. $^1H$ NMR ($CDCl_3$, ppm ranges are given because of amide rotamers and line broadening) δ 1.36 (s, 9H), 2.33 (m, 2H), 2.60 & 2.70 (2s, 3H), 2.8–3.6 (m, 3H), 4.94 (m, 2H), 5.59 (m, 1H), 6.9–7.4 (m, 3H).

The residue was dissolved in 80 mL of acetone, 40 mL of t-butanol and 40 mL of water. To this solution 1 mL of osmium tetroxide (4% solution in water) and 5.15 g (44 mmol) of 4-methylmorpholine N-oxide were added. After stirring for 26 h, the reaction was quenched with approximately 5 g of $Na_2SO_3$ and concentrated to 25% of the original volume. The residue was partitioned between water and 1:1 ether ($Et_2O$), ethyl acetate (EtOAc), the layers were separated and the aqueous layer was extracted with $Et_2O$:EtOAc. Each organic layer was washed with water, brine and dried by filtering through $Na_2SO_4$. The filtrate was concentrated to afford the crude diol.

A solution of the diol in 120 mL of tetrahydrofuran (THF) and 40 mL of water was treated with 9.42 g (44 mmol) of sodium periodate. After stirring for 2 h, the reaction was diluted with $Et_2O$:EtOAc and washed with water and brine. The organic layer was dried ($Na_2SO_4$) and the filtrate was concentrated. The residue was purified by prepLC using 30% EtOAc/hexane to furnish 11.74 g (83% yield for three steps) of the title compound as a thick oil.

$^1$H NMR ($CDCl_3$, ppm ranges are given because of amide rotomers and line broadening) δ 1.38 (s, 9H), 2.69 & 2.75 (2s, 3H), 2.6–3.65 (m, 5H), 6.95–7.4 (m, 3H), 9.67 (s, 1H).

EXAMPLE 2

1'-(3-(S)-(3,4-Dichlorophenyl)-4-(N-(t-butoxycarbonyl)(methylamino))butyl)-1-methanesulfonyl-spiro(indoline-3,4'-piperidine)

To a solution of 0.76 g (2.2 mmol) of 3-(S)-(3,4-dichlorophenyl)-4-(N-(t-butoxycarbonyl)methylamino) butanal (from Example 1) in 4 mL of methanol were added 0.608 g (2 mmol) of 1-methane-sulfonyl-spiro(indoline-3,4'-piperidine) hydrochloride and 0.6 g of powdered 4 Å molecular sieves. After 15 min a solution of 0.554 g (8.8 mmol) of $NaCNBH_3$ in 8 mL of THF was dropwise added. Some gas evolution was observed. After 2 h, when the reaction was complete by TLC, the mixture was filtered through a pad of celite, the reaction flask and the pad were rinsed with methanol. The filtrate was concentrated to approximately 5 ml and the residue was partitioned between saturated $NaHCO_3$ and $Et_2O$:EtOAc. The organic layer was washed with water, brine and dried over $Na_2SO_4$. The filtrate was concentrated and the residue was chromatographed on a flash column using a gradient of 49:49:2 to 74:24:2 EtOAc:hexane: triethylamine to furnish 0.94 g (72%) of the title compound as a foam.

$^1$H NMR ($CDCl_3$, ppm ranges are given because of amide rotomers and line broadening) δ 1.37 (s, 9H), 1.6–3.6 (m, 15H), 2.61 & 2.72 (2s, 3H), 2.86 (s, 3H), 3.74 (s, 2H), 6.95–7.4 (m, 7H).

EXAMPLE 3

1'-(3-((S)-(3,4-Dichlorophenyl))-4-(N-(3,5-dimethylbenzoyl)(methylamino))butyl)-1-methanesulfonyl-spiro(indoline-3,4'-piperidine)

Step A: 1'-(3-((S)-(3,4-dichlorophenyl))-4-(methylamino)butyl)-1-methanesulfonyl-spiro(indoline-3,4'-piperidine)

Cold trifluoroacetic acid (TFA, 4 mL) and 0.2 mL of anisole were added to 0.94 g (1.57 mmol) of 1'-(3-(S)-(3, 4-dichlorophenyl)-4-(N-(t-butoxycarbonyl)(methylamino)) butyl)-1-methanesulfonyl-spiro(indoline-3,4'-piperidine) and the mixture was stirred in an ice bath until all the foam dissolved. After stirring the resulting solution at room temperature for 30 min, it was concentrated in vacuo. The residue was partitioned between 0.5 N NaOH and $CH_2Cl_2$ and the layers were separated. The organic layer was washed with brine, dried over $Na_2SO_4$ and concentrated to give 0.7 g of foam which was used in the next step without purification.

$^1$H NMR ($CDCl_3$, ppm ranges are given because of amide rotomers and line broadening) δ 1.7–2.7 (m, 10H), 2.64 (s, 3H), 2.88 (s, 3H), 2.9–3.4 (m, 5H), 3.70 (s, 2H), 6.8–7.4 (m, 7H).

Step B: 1'-(3-((S)-(3,4-Dichlorophenyl))-4-(N-(3,5-dimethylbenzoyl)(methylamino))butyl)-1-methanesulfonyl-spiro(indoline-3,4'-piperidine)

A solution of 0.12 g (0.52 mmol) of 3,5-dimethylbenzoic acid in 2 mL of $CH_2Cl_2$ containing 1 drop of DMF was treated with 85 ul of oxalyl chloride. (Caution-gas evolution!) After 20 min the solution was concentrated in vacuo and the residue was mixed with 0.2 g (0.4 mmol) of 1'-(3-((S)-(3,4-dichlorophenyl))-4-(methylamino)butyl)-1-methane-sulfonyl-spiro(indoline-3,4'-piperidine) obtained from Step A, and 0.14 mL (1 mmol) of $Et_3N$ in 2 mL of $CH_2Cl_2$. After 1 h the reaction mixture was diluted with $CH_2Cl_2$ and washed with saturated $NaHCO_3$, water, and brine. The $CH_2Cl_2$ solution was dried over $Na_2SO_4$, filtered and concentrated. Purification of the residue by prep TLC using 2% $Et_3N$/EtOAc afforded 0.238 g (93% yield) of the title compound as a foam.

$^1$H NMR ($CDCl_3$, ppm ranges are given because of amide rotomers and line broadening) δ 1.6–2.4 (m, 10H), 2.27 (s, 6H), 2.6–3.9 (m, 10H), 2.86 (s, 3H), 6.6–7.5 (m, 10H).

The following compounds were prepared by substituting the required acid chloride for 3,5-dimethylbenzoyl chloride in Step B. 1'-(3-((S)-(3,4-dichlorophenyl))-4-(N-(benzoyl) (methylamino))butyl)-1-methanesulfonyl-spiro(indoline-3, 4'-piperidine)

Mass Spectrum (FAB) 602 ($^{37}Cl+^{35}Cl$ isotope), 600 ($^{35}Cl+^{35}Cl$ isotope).

1'-(3-((S)-(3,4-Dichlorophenyl))-4-(N-(3,5-bistrifluoromethylbenzoyl)(methylamino))butyl)-1-methanesulfonyl-spiro(indoline-3,4'-piperidine)

Mass Spectrum (FAB) 738 ($^{37}Cl+^{35}Cl$ isotope), 736 ($^{35}Cl+^{35}Cl$ isotope).

1'-(3-((S)-(3,4-Dichlorophenyl))-4-(N-(3-methylbenzoyl) (methylamino))-butyl)-1-methanesulfonyl-spiro (indoline-3,4'-piperidine)

$^1$H NMR ($CDCl_3$, ppm ranges are given because of amide rotomers and line broadening) δ 1.6–2.4 (m, 10H), 2.32 (s, 3H), 2.6–3.9 (m, 10H), 2.86 (s, 3H), 6.75–7.5 (m, 11H).

Mass Spectrum (FAB) 616 ($^{37}Cl+^{35}Cl$ isotope), 614 ($^{35}Cl+^{35}Cl$ isotope).

1'-(3-((S)-(3,4-Dichlorophenyl))-4-(N-(3-chlorobenzoyl) (methylamino))-butyl)-1-methanesulfonyl-spiro (indoline-3,4'-piperidine)

$^1$H NMR ($CDCl_3$, ppm ranges are given because of amide rotomers and line broadening) δ 1.6–2.4 (m, 10H), 2.6–3.9 (m, 10H), 2.86 (s, 3H), 6.75–7.5 (m, 11H).

Mass Spectrum (FAB) 635 ($^{37}Cl+^{35}Cl$ isotope), 633 ($^{35}Cl+^{35}Cl$ isotope).

1'-(3-((S)-(3,4-Dichlorophenyl))-4-(N-(3-trifluoromethylbenzoyl)(methylamino))butyl)-1-methanesulfonyl-spiro(indoline-3,4'-piperidine)

Mass Spectrum (FAB) 669 ($^{37}Cl+^{35}Cl$ isotope), 667 ($^{35}Cl+^{35}Cl$ isotope).

1'-(3-((S)-(3,4-Dichlorophenyl))-4-(N-(3,5-dichlorobenzoyl)(methylamino))-butyl)-1-methanesulfonyl-spiro(indoline-3,4'-piperidine)

$^1$H NMR ($CDCl_3$, ppm ranges are given because of amide rotomers and line broadening) δ 1.6–2.4 (m, 10H), 2.6–3.9 (m, 10H), 2.86 (s, 3H), 6.75–7.5 (m, 10H).

Mass Spectrum (FAB) 671 ($^{37}Cl+^{35}Cl$ isotope), 669 ($^{35}Cl+^{35}Cl$ isotope).

1'-(3-((S)-(3,4-Dichlorophenyl))-4-(N-(3-trifluoromethylphenylacetyl)(methylamino))butyl)-1-methanesulfonyl-spiro(indoline-3,4'-piperidine)

Mass Spectrum (FAB) 684 ($^{37}$Cl+$^{35}$Cl isotope), 682 ($^{35}$Cl+$^{35}$Cl isotope).

1'-(3-((S)-(3,4-Dichlorophenyl))-4-(N-(3-isopropyloxyphenylacetyl)(methylamino))butyl)-1-methanesulfonyl-spiro(indoline-3,4'-piperidine)

1'-(3-((S)-(3,4-Dichlorophenyl))-4-(N-(benzenesulfonyl)(methylamino))-butyl)-1-methanesulfonyl-spiro(indoline-3,4'-piperidine)

$^1$H NMR (CDCl$_3$, ppm ranges are given because of amide rotomers and line broadening) δ 1.65 (m, 3H), 1.8–2.3 (m, 7H), 2.62 (s, 3H), 2.7–3.05 (m, 4H), 2.86 (s, 3H), 3.3 (m, 2H), 3.74 (s, 2H), 7.0–7.7 (m, 12H).

Mass Spectrum (FAB) 637 ($^{37}$Cl+$^{35}$Cl isotope), 635 ($^{35}$Cl+$^{35}$Cl isotope).

The following compounds were also prepared by using the appropriate acid chloride under the conditions given in Step B above:

1'-(3-((S)-(3,4-dichlorophenyl))-4-(N-(3,5-difluorobenzoyl)(methylamino))butyl)-1-methanesulfonyl-spiro(indoline-3,4'-piperidine)

Mass Spectrum (FAB) 638 ($^{37}$Cl+$^{35}$Cl isotope), 636 ($^{35}$Cl+$^{35}$Cl isotope).

1'-(3-((S)-(3,4-Dichlorophenyl))-4-(N-(3-fluoro-5-(trifluoromethyl)benzoyl)(methylamino))butyl)-1-methanesulfonyl-spiro(indoline-3,4'-piperidine)

Mass Spectrum (CI) 688 ($^{37}$Cl+$^{35}$Cl isotope), 686 ($^{35}$Cl+$^{35}$Cl isotope).

1'-(3-((S)-(3,4-Dichlorophenyl))-4-(N-(1-naphthoyl)(methylamino))butyl)-1-methanesulfonyl-spiro(indoline-3,4'-piperidine)

$^1$H NMR (CDCl$_3$, ppm ranges are given because of amide rotomers and line broadening) d Mass Spectrum (FAB) ($^{37}$Cl+$^{35}$Cl isotope), ($^{35}$Cl+$^{35}$Cl isotope).

1'-(3-((S)-(3,4-Dichlorophenyl))-4-(N-(2-chlorophenylsulfonyl)(methylamino))butyl)-1-methylsulfonyl-spiro(indoline-3,4'-piperidine)

Mass Spectrum: 200, 202, 228, 230, 279, 308, 310, 494, 496, 670, 672 (cluster).

1'-(3-((S)-(3,4-Dichlorophenyl))-1-(N-(3-chlorophenylsulfonyl)(methylamino))-4-butyl)-1-methylsulfonyl-spiro(indoline-3,4'-piperidine)

Mass Spectrum: 200, 202, 228, 230, 279, 308, 310, 494, 496, 670, 672 (cluster).

1'-(3-((S)-(3,4-Dichlorophenyl))-4-(N-(4-chlorophenylsulfonyl)(methylamino))butyl)-1-methylsulfonyl-spiro(indoline-3,4'-piperidine)

Mass Spectrum: 200, 228, 230, 279, 494, 496, 669 (cluster).

1'-(3-((S)-(3,4-Dichlorophenyl))-4-(N-(3,5-dichlorophenylsulfonyl)(methylamino))butyl)-1-methylsulfonyl-spiro(indoline-3,4'-piperidine)

Mass Spectrum: 228, 230, 279, 494, 496, 703, 705 (cluster).

EXAMPLE 4

1-Benzyloxycarbonyl-spiro(indoline-3,4'-piperidinium)hydrochloride

A solution of 99 g (489 mmol) of 1'-methylspiro(indoline-3,4'-piperidine) (prepared according to Ong, H. H. et al, J. Med. Chem., 1983, 26, 981–986) in 1 L of CH$_2$Cl$_2$ and 82 mL (539 mmol) of Et$_3$N was cooled to 0–5° C. with an ice bath and 77 mL (539 mmol) of benzyl chloroformate was added over 30 min keeping the reaction temperature below 10° C. After stirring for 2 h 19 mL (136 mmol) of Et$_3$N and 15 mL (105 mmol) of benzyl chloroformate were added since the reaction was incomplete and stirred for 2 h. At this time, additional 19 mL (136 mmol) of Et$_3$N and 15 mL (105 mmol) of benzyl chloroformate were added. After 1 h, when a TLC indicated a complete reaction, the solution was concentrated in vacuo and the residue was partitioned between ether and saturated NaHCO$_3$. The layers were separated, the organic layer was washed with saturated NaHCO$_3$ and brine, and dried over MgSO$_4$. The filtrate was concentrated and the residue was chromatographed on 2 kg of silica gel using 1–5% MeOH/CH$_2$Cl$_2$ to obtain 117 g (71%) of 1-benzyloxycarbonyl-1'-methylspiro(indoline-3,4'-piperidine) as a yellow oil.

The yellow oil was dissolved in 800 mL of 1,2-dichloroethane and cooled in ice bath as 50 mL (463 mmol) of 1-chloroethyl chloroformate keeping the temperature below 10° C. The resulting solution was heated to reflux. Gas evolution was noticed when the reaction temperature reached 70–75° C. After 1 h the solution was cooled, concentrated to ca. 250 mL in vacuo and 700 mL of methanol was added. The mixture was refluxed for 1.5 h and gas evolution was observed. The reaction was cooled to room temperature and concentrated in vacuo to a wet solid. The solid was slurried with cold methanol, the solid was filtered, washed with cold methanol and dried. The filtrates and the washing were combined and concentrated to a brown foam. The brown foam and the filtered solid were suspended in CH$_2$Cl$_2$, washed with 2.5 N NaOH and the CH$_2$Cl$_2$ solution was dried. The residue was chromatographed on 2 kg of silica gel using a gradient of 94:5:1 to 89:10:1 CH$_2$Cl$_2$, methanol, NH$_4$OH to isolate 91.3 g of free base as a brown oil. The oil was dissolved in 1 L of EtOAc by adding methanol (ca. 10 mL) and HCl gas was passed through the solution. After stirring the acidic solution for 10 min, it was concentrated to a foam. The foam was triturated with ether and the solid was filtered, washed with more ether and dried to furnish 91.5 g (73%) of title compound as a light yellow solid.

EXAMPLE 5

3-((S)-(3,4-Dichlorophenyl))-4-((3,5-dimethylbenzoyl)methylamino)butanal

The title compound was prepared using the procedures described in Example 1 by substituting 3,5-dimethylbenzoyl chloride for di-t-butyl dicarbonate.

$^1$H NMR (CDCl$_3$, ppm ranges are given because of amide rotomers and line broadening) δ 2.27 (s, 6H), 2.6–3.9 (m, 8H), 6.5–7.5 (m, 6H), 9.73 (s, 1H).

EXAMPLE 6

1'-(3-((S)-(3,4-Dichlorophenyl))-4-(N-(3,5-dimethylbenzoyl)(methylamino))butyl)-1-benzyoxycarbonyl-spiro(indoline-3,4'-piperidine)

The title compound was prepared from 3-((S)-(3,4-dichlorophenyl))-4-((3,5-dimethylbenzoyl)methylamino) butanal (Example 5) and 1-benzyloxycarbonyl-spiro(indoline-3,4'-piperidinium) hydrochloride (Example 4) following the procedure of Example 2.

$^1$H NMR (CDCl$_3$, ppm ranges are given because of amide rotomers and line broadening) δ 1.6–2.35 (m, 10H), 2.27 (s, 6H), 2.6–3.9 (m, 10H), 5.23 & 5.3 (2 s, 2H), 6.6–7.6 (m, 15H).

Mass Spectrum (FAB) 686 ($^{37}$Cl+$^{35}$Cl isotope), 684 ($^{35}$Cl+$^{35}$Cl isotope).

EXAMPLE 7

1'-(3-((S)-(3,4-Dichlorophenyl))-4-(N-(3,5-dimethylbenzoyl)(methylamino))butyl)-spiro(indoline-3,4'-piperidine)

To a solution of 1.23 g (1.8 mmol) of 1'-(3-((S)-(3,4-dichlorophenyl))-4-(3,5-dimethylbenzoyl(methylamino))

butyl)-1-benzyoxycarbonyl-spiro(indoline-3,4'-piperidine) (Example 6) in 10 mL of ethanol and 0.8 mL of acetic acid (HOAc) was added 0.15 g of 10% Pd/C. The resulting mixture was hydrogenated on a Parr apparatus for 20 h. The catalyst was filtered and washed with EtOH. The combined filtrate was concentrated in vacuo and the residue was dissolved in $CH_2Cl_2$. The $CH_2Cl_2$ solution was washed with dilute (ca 0.5 N) NaOH and brine, and dried by filtering through $Na_2SO_4$. The filtrate was concentrated to furnish 1.03 g (quantitative) of the title compound as a foam which was used in the next reaction without purification.

$^1$H NMR (CDCl$_3$, ppm ranges are given because of amide rotomers and line broadening) δ 1.6–2.45 (m, 10H), 2.27 (s, 6H), 2.6–3.9 (m, 10H), 6.5–7.5 (m, 10H).

Mass Spectrum (FAB) 552 ($^{37}$Cl+$^{35}$Cl isotope), 550 ($^{35}$Cl+$^{35}$Cl isotope).

EXAMPLE 8

1'-(3-((S)-(3,4-Dichlorophenyl))-4-(N-(3,5-dimethylbenzoyl)(methylamino))butyl)-1-acetyl-spiro(indoline-3,4'-piperidine)

Acetyl chloride (16 uL) was added to a solution of 0.1 g (0.18 mmol) of 1'-(3-((S)-(3,4-dichlorophenyl))-4-(N-(3,5-dimethylbenzoyl)(methylamino))butyl)-spiro(indoline-3,4'-piperidine) (Example 7) in 4 mL of $CH_2Cl_2$ containing 30 mL of pyridine. After stirring for 2 h, the reaction mixture was diluted with $CH_2Cl_2$ and washed with saturated NaHCO$_3$, water, brine and dried. The residue after concentration of the filtrate was purified by prep TLC using 5% Et$_3$N/EtOAc as an eluent to afford 90 mg (84%) of the title compound.

$^1$H NMR (CDCl$_3$, ppm ranges are given because of amide rotomers and line broadening) δ 1.55–2.5 (m, 10H), 2.22 (s, 3H), 2.27 (s, 6H), 2.6–3.9 (m, 10H), 6.6–7.5 (m, 9H), 8.17 (d, 1H, J=12 Hz).

Mass Spectrum (FAB) 594 ($^{37}$Cl+$^{35}$Cl isotope), 592 ($^{35}$Cl+$^{35}$Cl isotope).

The following analogs were prepared by substituting the appropriate acylation reagent for acetyl chloride in the above procedure.

1'-(3-((S)-(3,4-Dichlorophenyl))-4-(N-(3,5-dimethylbenzoyl)(methylamino))butyl)-1-propionyl-spiro(indoline-3,4'-piperidine)

Mass Spectrum (FAB) 608 ($^{37}$Cl+$^{35}$Cl isotope), 606 ($^{35}$Cl+$^{35}$Cl isotope).

1'-(3-((S)-(3,4-Dichlorophenyl))-4-(N-(3,5-dimethylbenzoyl)(methylamino))butyl)-1-formyl-spiro(indoline-3,4'-piperidine)

Mass Spectrum (FAB) 580 ($^{37}$Cl+$^{35}$Cl isotope), 578 ($^{35}$Cl+$^{35}$Cl isotope).

1'-(3-((S)-(3,4-Dichlorophenyl))-4-(N-(3,5-dimethylbenzoyl)(methylamino))butyl)-1-t-butylcarbonyl-spiro(indoline-3,4'-piperidine)

Mass Spectrum (FAB) 636 ($^{37}$Cl+$^{35}$Cl isotope), 634 ($^{35}$Cl+$^{35}$Cl isotope).

1'-(3-((S)-(3,4-Dichlorophenyl))-4-(N-(3,5-dimethylbenzoyl)(methylamino))butyl)-1-methylaminocarbonyl-spiro(indoline-3,4'-piperidine)

Mass Spectrum (FAB) 609 (M+H, $^{37}$Cl+$^{35}$Cl isotope), 607 (M+H, $^{35}$Cl+$^{35}$Cl isotope).

1'-(3-((S)-(3,4-Dichlorophenyl))-4-(N-(3,5-dimethylbenzoyl)(methylamino))butyl)-1-ethoxycarbonyl-spiro(indoline-3,4'-piperidine)

Mass Spectrum (FAB) 624 ($^{37}$Cl+$^{35}$Cl isotope), 622 ($^{35}$Cl+$^{35}$Cl isotope).

1'-(3-((S)-(3,4-Dichlorophenyl))-4-(N-(3,5-dimethylbenzoyl)(methylamino))butyl)-1-ethanesulfonyl-spiro(indoline-3,4'-piperidine)

Mass Spectrum (FAB) 643 ($^{37}$Cl+$^{35}$Cl isotope), 641 ($^{35}$Cl+$^{35}$Cl isotope).

1'-(3-((S)-(3,4-Dichlorophenyl))-4-(N-(3,5-dimethylbenzoyl)(methylamino))butyl)-1-1-propanesulfonyl-spiro(indoline-3,4'-piperidine)

Mass Spectrum (FAB) 657 ($^{37}$Cl+$^{35}$Cl isotope), 655 ($^{35}$Cl+$^{35}$Cl isotope).

The following compound can also be prepared under the conditions given above:

1'-(3-((S)-(3,4-Dichlorophenyl))-4-(N-(3-fluoro-5-(trifluoromethyl)benzoyl)(methylamino))butyl)-1-acetyl-spiro(indoline-3,4'-piperidine)

Mass Spectrum (FAB) (CI) 652 ($^{37}$Cl+$^{35}$Cl isotope), 650 ($^{35}$Cl+$^{35}$Cl isotope).

An alternative method (method B) is given below:

1'-(3-((S)-(3,4-Dichlorophenyl))-4-(N-(3,5-dimethylbenzoyl)(methylamino))butyl)-1-acetyl-spiro(indoline-3,4'-piperidine)

1-Acetyl-spiro(indoline-3,4'-piperidine)

Acetyl chloride (1.4 mL, 19.9 mmol) was added to a solution of 5.35 g (16.6 mmol) of 1'-benzyloxycarbonyl-spiro(indoline-3,4'-piperidine) in 33 mL of $CH_2Cl_2$ and 3.2 mL (23.2 mmol) of Et$_3$N keeping the temperature between 0–5° C. by cooling in ice bath. After 10 min the cold bath was removed and reaction was stirred for 30 min at which time a TLC indicated complete reaction. The solution was diluted with $CH_2Cl_2$ and washed with water, brine and dried over $Na_2SO_4$. The filtrate was concentrated to a thick oil and the oil was dissolved in 40 mL of EtOH. Acetic acid (3 mL) and 0.8 g of 10% Pd/C were added to the solution and the resulting mixture was hydrogenated on a Parr apparatus for 3 h. The catalyst was filtered and washed with EtOAc and the combined filtrate was concentrated. The residue was partitioned between $CH_2Cl_2$ and water and 2N NaOH was added to this mixture until the aqueous layer was basic. The layers were separated and the aqueous layer was extracted with $CH_2Cl_2$. The combined organic layer was washed with brine, dried over $Na_2SO_4$ and the filtrate was concentrated to give 2.93 g (77%) of the title compound sufficiently pure for use in the next reaction.

1'-(3-((S)-(3,4-Dichlorophenyl))-4-(N-(3,5-dimethylbenzoyl)(methylamino))butyl)-1-acetyl-spiro(indoline-3,4'-piperidine)

To a solution of 0.284 g (0.75 mmol) of 3-((S)-(3,4-dichlorophenyl))-4-(N-(3,5-dimethylbenzoyl)(methylamino))butanal (Example 5) in 2 mL of MeOH were added 0.166 g (0.72 mmol) of 1-acetyl-spiro(indoline-3,4'-piperidine), 0.5 g of powdered 4 Å molecular sieves and 10 drops (ca. 0.1 mL) of acetic acid. After stirring the mixture for 1.5 h a solution of 0.189 g (3 mmol) of NaCNBH$_3$ in 3 mL of THF was added. Some gas evolution was observed. After 30 min when the reaction was complete by TLC the mixture was filtered through a pad of celite, the reaction flask and the pad were rinsed with MeOH. The filtrate was concentrated to approximately 3 mL and the residue was diluted with EtOAc. The EtOAc solution was washed with water, brine and dried over $Na_2SO_4$. The filtrate was concentrated and the residue was chromatographed on a flash column using 50% EtOAc-hexane followed by 2% Et3N-EtOAc and finally 93:5:2 EtOAc: MeOH: Et$_3$N to isolate 0.317 g (74%) of the title compound as a white foam.

EXAMPLE 9

1'-(3-((S)-(3,4-Dichlorophenyl))-4-(3,5-dimethylbenzoyl(methylamino))butyl)-1'-methyl- 1-methanesulfonyl-spiro(indoline-3,4'-piperidinium) iodide A solution of 53 mg (0.084 mmol) of 1'-(3-((S)-(3,4-dichlorophenyl))-4-(3,5-dimethylbenzoyl(methylamino))

butyl)-1-methanesulfonyl-spiro(indoline-3,4'-piperidine) in 5 drops of MeOH was diluted with 1 mL of ether and 0.5 mL of methyl iodide was added. The reaction mixture was stirred overnight while a solid was formed. The yellowish solid was allowed to settle and the supernatent was removed. The solid was washed with ether and dried to furnish 51 mg (78%) of the title compound.

EXAMPLE 10

1'-(3-(S)-(3,4-Dichlorophenyl)-4-(N-(R or S)-(3-methylbenzoyl)(methylamino))pentyl)-1-methanesulfonyl-spiro(indoline-3,4'-piperidine)

Step 1: N-Methoxy-N-methyl-2-(S)-(3,4-dichlorophenyl)-4-pentenamide

A mixture of 306 mg (1.25 mmol) of (2S)-(3,4-dichlorophenyl)-4-pentenoic acid (prepared according to the procedure of Hale, J. J.; Finke, P. E.; MacCoss, M. *Bioorganic & Medicinal Chemistry Letters* 1993, 3, 319–322) and 202 mg (1.50 mmol) of 1-hydroxybenzotriazole hydrate in 10 mL of methylene chloride was cooled to 0° C. and treated with 287 mg (1.50 mmol) of 1-(3-dimethylaminopropyl)-3-ethylcarbodiimide. The cooling bath was removed and after 45 min. a solution of 365 mg (3.75 mmol) of N,O-dimethylhydroxylamine hydrochloride and 522 µl (3.75 mmol) of triethylamine in 10 mL of methylene chloride was added via cannula. The mixture was then stirred at 22° C. for 4 hours and then quenched with 10 mL of water and diluted with 8 mL of methylene chloride. The layers were separated and the aqueous layer was extracted with methylene chloride (2×10 mL). The combined organic layers were washed with 10 mL of brine, dried over anhydrous sodium sulfate, filtered, and concentrated in vacuo. Flash chromatography on 75 g of silica gel using 1:9 v/v ethyl acetate/hexane as the eluant afforded 319 mg (89%) of the title compound as a clear oil.

$^1$H NMR (400 MHz, CDCl$_3$) δ 2.40 (pentet, 1H), 2.75 (pentet, 1H), 3.13 (s, 3H), 3.52 (s, 3H), 3.99–4.01 (m, 1H), 4.96–5.05 (m, 2H), 5.63–5.70 (m, 1H), 7.15 (dd, 1H), 7.35 (d, 1H), 7.41 (d, 1H).

Mass Spectrum (FAB): m/z 290 (M+H, $^{37}$Cl+$^{35}$Cl isotope, 50%), 288 (M+H, $^{37}$Cl+$^{37}$Cl isotope, 100%).

Step 2: 3-(S)-(3,4-dichlorophenyl)-5-hexen-2-one

A solution of 319 mg (1.11 mmoL) of N-methoxy-N-methyl-2-(S)-(3,4-dichlorophenyl)-4-pentenamide (from Step 1 above) in 10 mL of dry tetrahydrofuran was cooled to −70° C. and treated with 1.0 mL (1.40 mmol) of methyllithium and stirred between −70° C. to −40° C. After 3 hours, the reaction was quenched with 5 mL of water, and diluted with 10 mL of ethyl acetate. The layers were separated and the organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 44 g of silica gel using 1:3 v/v ethyl acetate/hexane as the eluant afforded 250 mg (93%) of the title compound as a clear oil.

$^1$H NMR (400 MHz, CDCl$_3$) δ 2.07 (s, 3H), 2.36 (pentet, 1H), 2.72 (pentet, 1H), 3.64 (t, 1H), 4.95–5.01 (m, 2H), 5.55–5.65 (m, 1H), 7.03 (dd, 1H), 7.30 (d, 1H), 7.39 (d, 1H).

Mass Spectrum (FAB): m/z 245 (M+H, $^{37}$Cl+$^{35}$Cl isotope, 30%), 243 (M+H, $^{37}$Cl+$^{37}$Cl isotope, 50%), 155 (60%), 119 (100%).

Step 3: N-Methyl 3-(S)-(3,4-dichlorophenyl)-5-hexen-2-(RS)-amine

A mixture of 102 mg (0.42 mmol) of 3-(S)-(3,4-dichlorophenyl)-5-hexen-2-one (from Step 2 above), 170 mg (2.52 mmol) of methylamine hydrochloride, and 234 µl (1.68 mmol) of triethylamine in 4.0 mL of methanol was treated with 16 mg (0.25 mmol) of sodium cyanoborohydride and stirred at 22° C. for 20 hours. Saturated aqueous sodium bicarbonate solution (1.0 mL) was added and the resulting milky mixture was diluted with 5.0 mL of ethyl acetate and 5.0 mL of water. The layers were separated and the organic layer was washed with water (3×5 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 42 g of silica gel using 10:1 v/v ether/ hexane as the eluant afforded 64 mg of the higher R$_f$ isomer (Isomer A) and 22 mg of a lower R$_f$ isomer (Isomer B) both as yellow oils.

$^1$H NMR (400 MHz, CDCl$_3$); Isomer A: δ 1.04 (d, 3H), 2.29–2.35 (m, 4H), 2.50–2.68 (m, 3H), 4.86–4.95 (m, 2H), 5.48–5.56 (m, 1H), 7.01 (dd, 1H), 7.26 (d, 1H), 7.34 (d, 1H); Isomer B: δ 0.86 (d, 3H), 2.32–2.50 (m, 4H), 2.51–2.53 (m, 1H), 2.68–2.73 (m, 2H), 4.88–4.98 (m, 2H), 5.54–5.61 (m, 1H), 6.97 (dd, 1H), 7.22 (d, 1H), 7.33 (d, 1H).

Mass Spectrum (Isomer A) (FAB): m/z 260 (M+H, $^{37}$Cl+$^{35}$Cl isotope, 70%), 258 (M+H, $^{35}$Cl+$^{35}$Cl isotope, 100%).

Step 4: N-Methyl-N-t-butoxycarbonyl-3-(S)-(3,4-dichlorophenyl)-5-hexen-2-(RS)-amine A solution of 1.1 g (4.1 mmol) of N-methyl-(3-(S)-(3,4-dichlorophenyl)-5-hexen-2-(R or S)-amine (Isomer B from Step 3 above) in 10 mL of dry methylene chloride was cooled to 0° C. and treated with 690 µl (5.0 mmol) of triethylamine and 1.2 g (5.3 mmol) of di-tert-butyl dicarbonate. The cooling bath was removed and the reaction was stirred at 22° C. for 20 hours. The reaction was quenched with 10 mL of water and diluted with 25 mL of methylene chloride. The layers were separated and the aqueous layer was extracted with methylene chloride (2×10 mL). The combined organic layers were washed with 15 mL of brine, dried over anhydrous sodium sulfate, filtered, and concentrated in vacuo. Flash chromatography on 72 g of silica gel using 1:3 v/v ethyl acetate/ hexane as the eluant afforded 1.4 g (95%) of the title compound as a yellow oil.

$^1$H NMR (400 MHz, CDCl$_3$, ranges are given due to amide rotamers and line broadening) δ 1.24–5.70 (22H), 6.88–7.40 (3H), 1.50 (s, 3H, N-CH$_3$).

Mass Spectrum (FAB): m/z 358 (M+H, $^{37}$Cl+$^{35}$Cl isotope, 30%), 302 (100%).

Step 5: N-Methyl-N-t-butoxycarbonyl-3-(S)-(3,4-dichlorophenyl)-4-(RS)-amino-pentanal A solution of 1.4 g (3.9 mmol) of N-methyl-N-t-butoxycarbonyl-3-(S)-(3,4-dichlorophenyl)-5-hexen-2-(RS)-amine (from Step 4 above) in 20 mL of 2:1:1 v/v/v acetone/t-butanol/water was treated with 30 mg (0.12 mmol) of osmium tetroxide. After 5 min., 691 mg (5.90 mmol) of N-methylmorpholine N-oxide was added and the resulting mixture was stirred at 22° C. for 4 hours. The reaction was quenched with 491 mg of sodium bisulfite and concentrated in vacuo to 25% of the original volume. The residue was partitioned between 20 mL of methylene chloride and 10 mL of water and the layers were separated. The aqueous layer was extracted with methylene chloride (2×10 mL). The combined organic layers were dried over anhydrous sodium sulfate, filtered, and concentrated in vacuo.

A solution of the crude diol in 24 mL of 3:1 v/v tetrahydrofuran/water was treated with 1.1 g (5.1 mmol) of sodium periodate and stirred at 22° C. for 20 hours. The reaction mixture was partitioned between 20 mL of ethyl ether and 10 mL of water and the layers were separated. The organic layer was washed with water (2×15 mL), dried over anhydrous sodium sulfate, filtered, and concentrated in vacuo. Flash chromatography on 68 g of silica gel using 4:1 v/v ethyl ether/hexane as the eluant afforded 372 mg of the higher $R_f$ isomer (Isomer A) and 879 mg of a lower $R_f$ isomer (Isomer B) both as yellow oils.

$^1$H NMR (400 MHz, CDCl$_3$) Isomer B: δ 1.19–1.34 (m, 13H), 2.45 (s, 3H, N-CH$_3$), 2.68–2.81 (m, 2H), 3.28–3.34 (m, 1H), 4.20–4.50 (m, 1H), 6.98–7.32 (m, 3H), 9.60 (s, 1H, -CHO).

Mass Spectrum (Isomer B) (FAB): m/z 360 (M+H, $^{37}$Cl+$^{35}$Cl isotope, 20%), 242 (100%).

Step 6: 1'-(3-(S)-(3,4-Dichlorophenyl)-4-(N-(R or S)-(t-butoxycarbonyl)(methylamino))pentyl)-1-methanesulfonyl-spiro(indoline-3,4'-piperidine)

A mixture of 217 mg (0.60 mmol) of N-methyl-N-t-butoxycarbonyl-3-(S)-(3,4-dichlorophenyl)-4-(RS)-amino-pentanal (from Step 5 above) and 262 mg (0.86 mmol) of 1-methanesulfonyl-spiro(indoline-3,4'-piperidine) hydrochloride in 13 mL of methanol was treated with 115 mg (1.83 mmol) of sodium cyanoborohydride and stirred at 22° C. for 20 hours. Saturated sodium bicarbonate solution (1.0 ml) was added and the resulting milky mixture was concentrated to 50% of its original volume. The residue was partitioned between 25 mL of ethyl acetate and 15 mL of water and the layers were separated. The organic layer was washed with water (3×10 mL). The aqueous layers were extracted with 20 mL of ethyl acetate. The combined organic layers were washed with 15 mL of brine, dried over anhydrous sodium sulfate, filtered, and concentrated in vacuo. Flash chromatography on 42 g of silica gel using 5:95 v/v methanol/methylene chloride as the eluant afforded 329 mg (89%) of the title compound as a white foam.

$^1$H NMR (400 MHz, CDCl$_3$, ranges are given due to amide rotamers and line broadening) δ 1.20–2.90 (31H), 3.74 (s, 3H, N—SO$_2$CH$_3$), 7.05–7.41 (m, 8H).

Mass Spectrum (FAB): m/z 612 (M+H, $^{37}$Cl+$^{35}$Cl isotope, 70%), 610 (M+H, $^{37}$Cl+$^{37}$Cl isotope, 100%).

Step 7: 1'-(3-(S)-(3,4-Dichlorophenyl)-4-(N-(R or S)-(methylamino))pentyl)-1-methanesulfonyl-spiro(indoline-3,4'-piperidine)

To a solution of 329 mg (0.54 mmol) of 1'-(3-(S)-(3,4-dichlorophenyl)-4-N((R or S)-(t-butoxycarbonyl) (methylamino))pentyl)-1-methanesulfonyl-spiro(indoline-3,4'-piperidine) (from Step 6 above) in 8.0 mL of dry methylene chloride at 0° C. was added 117 μl (1.1 mmol) of anisole and 2.0 mL of trifluoroacetic acid. The cooling bath was removed and the reaction was stirred at 22° C. for 20 minutes. The reaction was concentrated in vacuo. The residue was partitioned between 10 mL of methylene chloride and 5.0 mL of water. The organic layer was washed with 2N NaOH (3×5 mL), dried over anhydrous sodium sulfate, filtered, and concentrated in vacuo. Flash chromatography on 42 g of silica gel using 5:95:0.5 v/v/v methanol/methylene chloride/ammonium hydroxide as the eluant afforded 221 mg (80%) of the title compound as a clear oil.

$^1$H NMR (400 MHz, CDCl$_3$) δ 1.05 (d, 3H, J=6.2 Hz), 1.62–2.85 (m, 17H), 2.30 (s, 3H, N—CH$_3$), (7.03–7.37 (m, 7H).

Mass Spectrum (FAB): m/z 512 (M+H, $^{37}$Cl+$^{35}$Cl isotope, 70%), 510 (M+H, $^{37}$Cl+$^{37}$Cl isotope, 100%).

Step 8: 1'-(3-(S)-(3,4-Dichlorophenyl)-4-(N-(R or S)-(3-methylbenzoyl)(methylamino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Step 7 above) using a procedure identical to Example 3, Step (b), substituting m-toluoyl chloride for 3,5-dimethylbenzoyl chloride.

$^1$H NMR (400 MHz, CDCl$_3$, ranges are given due to amide rotamers and line broadening) δ 1.42 (δ, 3H, J=6.7 Hz), 1.60–2.30 (16H), 2.54 (s, 3H, Ph—CH$_3$), 2.87 (s, 3H, N—CH$_3$), 3.74 (s, 3H, N—SO$_2$CH$_3$), 7.05–7.79 (m, 11H).

Mass Spectrum (FAB): m/z 630 (M+H, $^{37}$Cl+$^{35}$Cl isotope, 70%), 628 (M+H, $^{37}$Cl+$^{37}$Cl isotope, 100%).

EXAMPLE 11

1'-(3-(S)-(3,4-Dichlorophenyl)-4-(N-(R or S)-(3,5-bis(trifluoromethyl)benzoyl)(methylamino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Example 1, Step 7 above) using a procedure identical to Example 3 Step (b), substituting 3,5-bis(trifluoromethyl)benzoyl chloride for 3,5-dimethylbenzoyl chloride.

$^1$H NMR (400 MHz, CDCl$_3$, ranges are given due to amide rotamers and line broadening) δ 1.38–3.00 (22H), 3.74 (s, 3H, N—SO$_2$CH$_3$), 6.40–7.41 (m, 10H).

Mass Spectrum (FAB): m/z 752 (M+H, $^{37}$Cl+$^{35}$Cl isotope, 40%), 750 (M+H, $^{37}$Cl+$^{37}$Cl isotope, 60%), 241 (100%).

EXAMPLE 12

1'-(3-(S)-(3,4-Dichlorophenyl)-4-(R or S)-(3,5-dimethylbenzoyl(methylamino))pentyl)-1-methanesulfonyl-spiro(indoline-3,4'-piperidine)

The title compound was prepared from 1'-(3-(S)-(3,4-dichlorophenyl)-4-(R or S)-(methylamino)pentyl)-1-methanesulfonyl-spiro(indoline-3,4'-piperidine) (from Example 1, Step 7 above) using a procedure identical to Example 3, Step (b).

$^1$H NMR (400 MHz, CDCl$_3$, ranges are given due to amide rotamers and line broadening) δ 1.37–2.86 (28H), 3.74 (s, 3H, N—SO$_2$CH$_3$), 6.24–7.41 (m, 10H).

Mass Spectrum (FAB): m/z 642 (M+H, $^{37}$Cl+$^{35}$Cl isotope, 70%), 644 (M+H, $^{37}$Cl+$^{37}$Cl isotope, 100%).

EXAMPLE 13

(1'-(3-(S)-(3,4-Dichlorophenyl)-4-(R or S)-(3,5-dichlorobenzoyl(methylamino))pentyl)-1-methanesulfonyl-spiro(indoline-3,4'-piperidine)

The title compound was prepared from 1'-(3-(S)-(3,4-dichlorophenyl)-4-(R or S )-(methylamino)pentyl)-1-methane sulfonyl-spiro(indoline-3,4'-piperidine) (from Example 1, Step 7 above) using a procedure identical to Example 3, Step (b), substituting 3,5-dichlorobenzoyl chloride for 3,5-dimethylbenzoyl chloride.

$^1$H NMR (400 MHz, CDCl$_3$, ranges are given due to amide rotamers and line broadening) δ 1.38–2.93 (22H), 3.73 (s, 3H, N—SO$_2$CH$_3$), 6.53–7.42 (m, 10H).

Mass Spectrum (FAB): m/z 684 (M+H, $^{37}$Cl+$^{35}$Cl isotope, 70%), 686 (M+H, $^{37}$Cl+$^{37}$Cl isotope, 100%).

EXAMPLE 14

1'-(3-((S)-(3,4-dichlorophenyl))-4-(N-(3-bromo-5-methylbenzoyl)(methylamino))butyl)-1-methanesulfonyl-spiro(indoline-3,4'-piperidine)

Step A: 3-Bromo-5-methylbenzoic acid

To a solution of 0.38 g (1.44 mmol) of 3-bromo-5-methylbenzyl bromide (prepared by NBS bromination of 3,5-dimethylbromobenzene) in 22 mL of MeCN and 50 mL of water was added 7.8 mL (28.8 mmol) of aqueous sodium hypochlorite (13% active Cl). The mixture was allowed to stand in an ultrasonic cleaning bath for 14 h. The reaction was acidified with HCl to pH 3 and extracted with $CH_2Cl_2$. The organic layer was washed with water, brine and dried with $Na_2SO_4$. The filtrate was concentrated and the residue which was a mixture of the desired acid and the aldehyde was dissolved in 3 mL of acetone. The solution was treated with 6 N Jones reagent until the orange color persisted. After stirring for 20 min the excess reagent was destroyed by adding few drops of i-PrOH. The solution was diluted with water and extracted with $CH_2Cl_2$. The $CH_2Cl_2$ layer was washed with brine, dried and the filtrate was concentrated. The residue was purified by prep TLC using 0.5:30:69.5 of HOAc:EtOAc:hexane to isolate 0.14 g (45%) of 3-bromo-5-methylbenzoic acid.

Step B: 1'-(3-((S)-(3,4-dichlorophenyl))-4-(N-(3-bromo-5-methylbenzoyl)(methylamino))butyl)-1-methanesulfonyl-spiro(indoline-3,4'-piperidine)

3-Bromo-5-methylbenzoic acid was used in the acylation reaction according to the procedure of Example 3, Step B to obtain the title compound.

Mass Spectrum (CI) 696 ($^{37}Cl+^{35}Cl$ isotope), 694 ($^{35}Cl+^{35}Cl$ isotope).

EXAMPLE 15

1'-(3-((S)-(3,4-Dichlorophenyl))-4-(N-(3,5-dimethylbenzoyl)(methylamino))butyl)-1-(2-aminoacetyl)-spiro(indoline-3,4'-piperidine)

A solution of 65 mg (0.31 mmol) of carbobenzyloxygly-cine in 3 mL of $CH_2Cl_2$ was treated with 82 mg (0.41 mmol) of 1-ethyl-3-(3-dimethylaminopropyl)carbodiimide and 56 mg (0.41 mmol) of 1-hydroxybenzotriazole and 42 mg (0.41 mmol) of N-methylmorpholine. After 10 min 123 mg (0.21 mmol) of 1'-(3-((S)-(3,4-dichlorophenyl))-4-(N-(3,5-dimethylbenzoyl)(methylamino))butyl)-spiro(indoline-3,4'-piperidine) (Example 7) was added and the reaction was stirred for 2 h. The mixture was diluted with $CH_2Cl_2$ and washed with water, brine, dried and concentrated to give 0.184 g of residue. The residue in 10 drops of HOAc was dissolved in 3 mL of EtOH and the solution was hydrogenated on a Parr apparatus for 16 h.

The catalyst was filtered and washed with EtOAc. The filtrate was washed with 10% $Na_2CO_3$, brine and concentrated. The residue was purified by prep TLC using 30% MeOH-EtOAc to give 80 mg (59%) of the title compound.

Mass Spectrum (CI) 651 ($^{37}Cl+^{35}Cl$ isotope), 649 ($^{35}Cl+^{35}Cl$ isotope).

EXAMPLE 16

1'-(3-((S)-(3,4-Dichlorophenyl))-4-(N-(3,5-dimethylbenzoyl)(methylamino))butyl)-1-methyl-spiro(indol-2-one-3,4'-piperidine)

Step A: 1,1'-Dimethyl-spiro(indol-2-one-3,4'-piperidine)

A solution of 0.1 g (0.68 mmol) of N-methyl-2-oxo-indole in 2 mL of THF was added to a well stirred suspension of 0.14 g (3.4 mmol) of NaH in 2 mL of THF with cooling in ice bath. After the gas evolution had stopped the cold bath was removed and the mixture was heated in a 50° C. bath for another 15 min. The reaction was allowed to cool to room temperature and 0.68 mL of DMSO was added and more gas evolution was observed. After stirring for 10 min, the reaction mixture was cooled in ice bath and 0.144 g of mechlorethamine hydrochloride was added. The mixture was warmed to room temperature and stirred overnight. Next morning, the reaction was quenched with water and extracted with EtOAc. The EtOAc extract was washed with brine, dried with $Na_2SO_4$ and filtered. The filtrate was concentrated and the residue was purified by prep TLC using 89:10:1 EtOAc:MeOH:$Et_3N$ to furnish 25 mg (15%) of the title compound.

Step B: 1-Methyl-spiro(indol-2-one-3,4'-piperidine)

A solution of 25 mg (0.11 mmol) of 1,1'-dimethyl-spiro (indol-2-one-3,4'-piperidine) (from Step A above) in 1 mL of dry dichloroethane was treated with 0.023 mL (0.22 mmol) of 1-chloroethyl chloroformate (ACECl) under a dry $N_2$ atmosphere. After 30 min at room temperature, the solution was kept in a 50° C. bath for 30 min. The reaction mixture was cooled to room temperature, 2 mL of MeOH was added and reheated to 60° C. After 30 min the solution was cooled and concentrated in vacuo. The residue was partitioned between water and EtOAc and the aqueous phase was adjusted to pH 9 by adding 1N NaOH. The layers were separated and the combined EtOAc solution was washed with brine and dried. The filtrate upon concentration gave 34 mg of a residue which was a mixture of the desired compound and the starting material, but was sufficiently pure to be used in the next reaction.

Step C: 1'-(3-((S)-(3,4-Dichlorophenyl))-4-(N-(3,5-dimethylbenzoyl)(methylamino))butyl)-1-methyl-spiro (indol-2-one-3,4'-piperidine)

A reaction of 49 mg (0.13 mmol) of 3-((S)-(3,4-dichlorophenyl))-4-(N-(3,5-dimethylbenzoyl)methylamino) butanal (Example 5) with 34 mg of impure 1-methyl-spiro (indol-2-one-3,4'-piperidine) (from Step B) according to the procedure of Example 8, method B furnished 32 mg of the title compound after purification by prep TLC.

Mass Spectrum (CI) 580 ($^{37}Cl+^{35}Cl$ isotope), 578 ($^{35}Cl+^{35}Cl$ isotope).

EXAMPLE 17

1'-(3-((S)-(3,4-Dichlorophenyl))-4-(N-(3,5-dichlorobenzoyl)(methylamino))butyl)-1-methyl-spiro(isoindol-1-one-3,4'-piperidine)

Mass Spectrum (CI) 622 ($^{37}Cl+^{35}Cl$ isotope), 620 ($^{35}Cl+^{35}Cl$ isotope).

EXAMPLE 18

1'-(3-((S)-(3,4-Dichlorophenyl))-4-(N-(3,5-dimethylbenzoyl)(methylamino))butyl)-spiro(2-oxo-tetrahydroquinoline-4,4'-piperidine)

Step A: 1'-Trifluoroacetyl-spiro(1-indanone-3,4'-piperidine)

Cold trifluoroacetic acid (15 mL) and 0.6 mL of anisole were added to 2 g (6.6 mmol) of 1'-t-butoxycarbonyl-spiro (1-indanone- 3,4'-piperidine) and the resulting solution was stirred in ice bath for 1 h. The reaction mixture was concentrated in vacuo and the residue was partitioned between $CH_2Cl_2$ and 0.5 N NaOH. The organic layer was washed with brine, dried with $Na_2SO_4$ and concentrated. The residual orange oil was dissolved in 10 mL of $CH_2Cl_2$ and 1.92 mL (13.7 mmol) of $Et_3N$, 1 mL (7.1 mmol) of trifluoroacetic anhydride and 3 crystals of DMAP were added. After stirring for 4 h, the reaction mixture was diluted with $CH_2Cl_2$ and washed with water, brine and dried. The solution was filtered and the filtrate was concentrated to yield 2.0 g (quantitative) of the desired product as a solid.

$^1$H NMR (CDCl$_3$) δ 1.65 (d, 2H, J=14 Hz), 2.05 (m, 2H), 2.67 (ABq, 2H), 2.89 (m, 1H), 3.28 (m, 1H), 4.11(d, 1H, J=14 Hz), 4.67 (dt, 1H, J=14 and 2 Hz), 7.5–7.8 (m, 4H).

Step B: 1'-Trifluoroactyl-spiro-(2-oxo-1,2,3,4-tetrahydroquinoline-4,4'-piperidine) and 1'-trifluoroactyl-spiro-(1-oxo-1,2,3,4-tetrahydroisoquinoline-4.4'-piperidine)

To a mixture of 1.09 g (16.8 mmol) of Sodium azide in 1.2 mL of water and 6.6 mL of $CHCl_3$ was added 0.46 mL of concentrated $H_2SO_4$ (36 N) keeping the temperature between 0–5° C. (Caution!) After 10 min the cold bath was removed and the reaction was stirred for 3 h, at which time the $CHCl_3$ layer was separated from the aqueous layer. The $CHCl_3$ layer containing $HN_3$ was dried and the filtrate was added to a solution of 2 g (6.7 mmol) of 1'-trifluoroacetyl-spiro(1-indanone-3,4'-piperidine) (from Step A) in 7 mL of $CHCl_3$. Concentrated $H_2SO_4$ (1.8 mL) was added to this solution and the reaction was allowed to age for 30 min. The mixture was heated in a 45° C. bath for 45 min and then stirred at room temperature for 16 h. Next morning, the reaction mixture was poured into ice and the layers were separated. The aqueous layer was neutralized with aq. NaOH and extracted with EtOAc. The combined organic phases were washed with brine, dried and concentrated. The residue was chromatographed using 50–80% EtOAc-$CH_2Cl_2$ to isolate 0.34 g (16%) of 1'-trifluoroactyl-spiro(2-oxo-1,2,3,4-tetrahydroquinoline-4,4'-piperidine) and 0.13 g of 1'-trifluoroactyl-spiro(1-oxo-1,23,4-tetrahydroisoquinoline-4,4'-piperidine). In addition, 0.72 g (36%) of the starting indanone was recovered.

$^1$H NMR ($CDCl_3$) Isomer A: δ 1.82 (m, 2H), 1.96 (m, 2H), 2.75 (ABq, 2H, J=14 Hz), 3.16 (t, 1H), 3.46 (t, 1H), 3.9 (d, 1H), 4.42 (d, 1H), 6.8–7.3 (m, 4H), 8.49 (br s, 1H); Isomer B: δ 1.9–2.1 (m, 4H), 3.09 (t, 1H), 3.42 (m, 1H), 3.61 (ABq, 2H), 3.94 (d, 1H), 4.45 (d, 1H), 6.72 (br s, 1H), 7.3–7.6 (m, 3H), 8.11 (d, 1H).

Step C: Spiro-(2-oxo-1,2,3,4-tetrahydroquinoline-4,4'-piperidine)

To a solution of 0.3 g (0.97 mmol) of 1'-trifluoroacetyl-spiro-(2-oxo-1,2,3,4-tetrahydroquinoline-4,4'-piperidine) (from Step B) in 4 mL of MeOH was added 0.16 g (2.9 mmol) of KOH in 1 mL of water. After stirring the reaction for 16H the solution was concentrated and the residue was partitioned between EtOAc and water. The EtOAc layer was washed with brine, dried with $Na_2SO_4$ and concentrated to give 0.16 g (76%) of the title compound as a white solid.

$^1$H NMR ($CDCl_3$) δ 1.6–2.0 (m, 4H), 2.72 (s, 2H), 2.95 (m, 4H), 6.7–7.4 (m, 4H), 8.4 (br s, 1H).

Step D: 1'-(3-((S)-(3,4-Dichlorophenyl))-4-(N-(3,5-dimethylbenzoyl)(methylamino))butyl)-spiro(2-oxo-tetrahydro-quinoline-4,4'-piperidine)

The title compound was obtained by reductive amination of 3-((S)-(3,4-dichlorophenyl))-4-((3,5-dimethylbenzoyl) methylamino)butanal (Example 5) by spiro-(2-oxo-1,2,3,4-tetrahydroquinoline-4,4'-piperidine) obtained in Step C according to the procedure of Example 8, method B.

Mass Spectrum (CI) 580 ($^{37}Cl+^{35}Cl$ isotope), 578($^{35}Cl+^{35}Cl$ isotope).

EXAMPLE 19

1'-(3-((S)-(3,4-Dichlorophenyl))-4-(N-(3,5-dichlorobenzoyl)(methylamino))butyl)-1-methyl-spiro(2-oxo-tetrahydroquinoline-4,4'-piperidine)

Step A: 1-Methyl-spiro-(2-oxo-1,2,3,4-tetrahydroquinoline-4,4'-piperidine)

To a solution of 0.15 g (0.48 mmol) of 1'-trifluoroacetyl-spiro-(2-oxo-1,2,3,4-tetrahydroquinoline-4,4'-piperidine) (from Example 18, Step B) in 1.7 mL of DMF was added 19 mg (0.77 mmol) of 95% NaH at 0° C. After 15 min 0.063 mL (1 mmol) of methyl iodide was added and the reaction was allowed to warm to room temperature. After stirring for 16H the reaction was not complete, so an additional 0.015 mL of methyl iodide was added and the solution was heated in a 45° C. bath. After 2H the reaction was cooled to room temperature and partitioned between EtOAc and water. The EtOAc layer was washed with brine, dried and the filtrate was concentrated. The residue was purified by prep TLC using 33% EtOAc-hexane to provide 1-methyl-1'-trifluoroacetyl-spiro-(2-oxo- 1,2,3,4-tetrahydroquinoline-4, 4'-piperidine). Hydrolysis of this trifluoroacetamide as described in Example 55, Step C furnished 71 mg (64%) of the title compound.

$^1$H NMR ($CDCl_3$) δ 1.61 (d, 2H), 1.92 (m, 2H), 2.74 (s, 2H), 2.98 (m, 4H), 3.36 (s, 3H), 7.0–7.4 (m, 4H).

Step B: 1'-(3-((S)-(3,4-dichlorophenyl))-4-(N-(3,5-dichlorobenzoyl)(methylamino))butyl)-1-methyl-spiro(2-oxo-tetrahydroquinoline-4,4'-piperidine The title compound was prepared by reaction of the amine from Step A and 3-((S)-(3,4-dichlorophenyl))-4-((3,5-dichlorobenzoyl)methylamino)butanal as described in Example 18, Step D.

Mass Spectrum (CI) 636 ($^{37}Cl+^{35}Cl$ isotope), 634 ($^{35}Cl+^{35}Cl$ isotope).

EXAMPLE 20

4-Bromo-2-(S)-(4-fluorophenyl)-1-(N-(3,5-bistrifluoromethylbenzoyl)methylamino)butane Step A: 3-(S)-(4-Fluorophenyl)-4-(N-(3,5-bistrifluoromethylbenzoyl)methylamino)butanol A solution of 1.67 g (3.84 mmol) of 3-((S)-(4-fluorophenyl)-4-(N-(3,5-(bistrifluoromethyl)benzoyl) (methylamino))butanal (prepared from 4-fluorophenylacetic acid as described by J. Hale et. al., *Bioorganic & Medicinal Chemistry Letters* 1993, 3, 319–322) in 16 mL of absolute ethanol at 0° C. was treated with 172 mg (4.55 mmol) of sodium borohydride. After stirring for 1 h at room temperature, the reaction was quenched with saturated $NH_4Cl$ and extracted twice with ethyl acetate. The combined organic layers were washed with brine, dried ($MgSO_4$) and evaporated to give 1.59 of residual oil. Purification on a silica gel flash column (30:70 then 50:50 ethyl acetate:hexanes) provided 1.21 g (72%) of the title compound as a viscous oil.

Mass Spectrum ($CI/NH_3$) M+H=438.

Step B: 4-Bromo-2-(S)-(4-fluorophenyl)-1-(N-(3,5-bistrifluoromethylbenzoyl)methylamino)butane To a solution of 1.19 g (2.72 mmol) of 3-(S)-(4-fluorophenyl)-4-(N-(3,5-bistrifluoromethylbenzoyl) methylamino)butanol in 20 mL of acetonitrile was added 1.49 g (3.53 mmol) of triphenylphosphine dibromide. After 1.5 h the reaction was partitioned between ethyl acetate and water. The organic layer was washed with brine, dried ($MgSO_4$) and concentrated to give 2.33 g of crude white solid. Purification on a silica gel flash column (30:70 ethyl acetate:hexanes) gave 944 mg (69%) of the desired bromide as a viscous oil.

Mass Spectrum (CI/NH3) M+H=500, 502 ($^{79,81}Br$ isotope).

EXAMPLE 21

1'-(3-(S)-(4-Fluorophenyl)-4-(N-(3,5-bistrifluoromethylbenzoyl)(methylamino))butyl)-1-acetyl-spiro(indoline-3,4'-piperidine)

To 40 mg (0.08 mmol) of the bromide prepared in Example 20, Step B and 0.21 ul (0.12 mmol) of N,N-diisopropylethylamine in 0.5 mL of acetonitrile was added 37 mg (0.16 mmol) of 1-acetyl-spiro(indoline-3,4'-piperidine). The resultant mixture was heated in a tightly capped vial at 50° C. for four days. The solvent was evaporated and the residue was purified on a 1000 micron silica gel prep plate (93:5:2 ethyl acetate:methanol:triethylamine) to furnish 46.6 mg (90%) of the title compound as a white foam.

Mass Spectrum (CI/NH3) M+H=650.

The compounds in Examples 22–26 were prepared as in Example 21 from the requisite bromide, prepared from the corresponding phenylacetic acid as described in Example 20, and the required 1-substituted-spiro(indoline-3,4'-piperidine).

EXAMPLE 22

1l'-(3-(S)-(3-Chlorophenyl)-4-(N-(3,5-bistrifluoromethylbenzoyl)(methylamino))butyl)-1-acetyl-spiro (indoline-3,4'-piperidine)

Mass Spectrum (CI/NH3) M+H=666, 668 ($^{35,37}$Cl-isotope).

EXAMPLE 23

1'-(3-(S)-(4-Chlorophenyl)-4-(N-(3,5-bistrifluoromethylbenzoyl)(methylamino))butyl)-1-acetyl-spiro(indoline-3,4'-piperidine)

Mass Spectrum (CI/NH3) M+H=666, 668 ($^{35,37}$Cl-isotope).

EXAMPLE 24

1'-(3-(S)-(3,4-Difluorophenyl)-4-(N-(3,5-bistrifluoromethylbenzoyl)(methylamino))butyl)-1-acetyl-spiro(indoline-3,4'-piperidine)

Mass Spectrum (CI/NH3) M+H=668.

EXAMPLE 25

1'-(3-(S)-(3,4-Methylenedioxyphenyl)-4-(N-(3,5-bistrifluoromethylbenzoyl)-(methylamino))butyl)-1-methanesulfonyl-spiro(indoline-3,4'-piperidine)

Mass Spectrum (CI/NH3) M+H=712.

EXAMPLE 26

1'-(3-(RS)-(3,5-Dichlorophenyl)-4-(N-(3,5-bistrifluoromethylbenzoyl)(methylamino))butyl)-1-methanesulfonyl-spiro(indoline-3,4'-piperidine)

Mass Spectrum (CI/NH3) M+H=736, 738 ($^{35,37}$Cl-isotope).

EXAMPLE 27

1'-(3-(S)-(4-Chlorophenyl)-4-(N-(3,5-bistrifluoromethylbenzoyl)(methylamino))butyl)-spiro(2,3-dihydrobenzothiophene-3,4'-piperidine)

The title compound was prepared as in Example 21 from 4-bromo-2-(S)-(4-chlorophenyl)-1-(N-(3,5-bistrifluoromethylbenzoyl)methylamino)butane and spiro(2,3-dihydrobenzothiophene-3,4'-piperidine) hydrochloride except that 3 eq. of diisopropylethylamine were used.

Mass Spectrum (CI/NH3) M+H=641,643 ($^{35,37}$Cl-isotope).

EXAMPLE 28

1'-(3-(RS)-(4-Pyridyl)-4-(N-(3,5-bistrifluoromethylbenzoyl)(methylamino))butyl)-1-acetyl-spiro(indoline-3,4'-piperidine)

The title compound was prepared from 3-(S)-(4-pyridyl)-4-(N-(3,5-bistrifluoromethylbenzoyl)methylamino)butanal (prepared from 4-pyridylacetic acid as described by J. Hale et. al., *Bioorganic & Medicinal Chemistry Letters* 1993, 3, 319–322) by reductive amination as described in Example 2.

Mass Spectrum (CI/NH3) M+H=633.

EXAMPLE 29

1'-(3-(S)-(3,4-Dichlorophenyl)-4-(N-(3,5-dimethylbenzoyl)(ethylamino))butyl)-1-methanesulfonyl-spiro(indoline-3,4'-piperidine)

Step A: 4-Bromo-2-(S)-(3,4-dichlorophenyl)-1-(N-(3,5-dimethylbenzoyl)methylamino)butane The title compound was prepared as in Example 20, Steps A and B, from 3-(S)-(3,4-dichlorophenyl)-4-(N-(3,5-dimethylbenzoyl)ethylamino)butanal (prepared from 3,4-dichlorophenylacetic acid as described by J. Hale et. al., (*Bioorganic & Medicinal Chemistry Letters* 1993, 3, 319–322) using ethylamine rather than methylamine to form the intermediate amide).

Mass Spectrum (CI/NH3) M=454, 456 ($^{79,81}$Br isotope).

Step B: 1'-(3-(S)-(3,4-Dichlorophenyl)-4-(N-(3,5-dimethylbenzoyl)-(ethylamino))butyl)-1-methanesulfonyl-spiro(indoline-3,4'-piperidine)

The title compound was prepared from the bromide prepared in Step A and 1-acetyl-spiro(indoline-3,4'-piperidine) as described in Example 21.

Mass Spectrum (CI/NH3) M+H=641, 643 ($^{35,37}$Cl-isotope).

EXAMPLE 30

5-Fluoro-spiro(2,3-dihydrobenzofuran-3,4'-piperidine)hydrochloride salt

Step 1) 4-(2,5-Difluorophenyl)-4-methoxycarbonyl-1-methylpiperidine

Methyl 2,5-difluorophenylacetate (4.8 g, 26 mmol) and mechlorethamine hydrochloride (5.0 g, 26 mmol) in DMSO (15 mL) and THF (50 mL) at 0° C. was carefully treated with NaH (2.5 g, 104 mmol). The reaction was gradually warmed to reflux over 1 h and refluxed further for 1 h. The reaction was cooled to 0° C., and 6N HCl (25 mL) was slowly added. The reaction was diluted with 1N HCl (200 mL) and washed with hexane (200 mL). The aqueous layer was cooled to 0° C. and adjusted to pH 12 with solid $K_2CO_3$. The product was extracted with ethyl acetate (200 mL), washed with brine (100 mL), dried ($MgSO_4$), and concentrated to 4.1 g (59%) of the title compound as an oil.

$^1$H NMR (400 MHz, $CDCl_3$) δ 7.34 (dq, 1H), 6.88 (m, 1H) 6.78 (ddd, 1H) 6.69 (minor NMe invertomer, dm), 6.59 (minor NMe invertomer, dd), 3.69 (s, 3H), 3.80 (minor invertomer, s), 2.71 (d, 2H), 2.48 (d, 2H), 2.38 (t, 2H), 2.25 (s, 3H), 2.10 (t, 2H) ppm.

Step 2) 4-(2,5-Difluorophenyl)-4-hydroxymethyl-1-methylpiperidine

EtOH (5.1 mL, 86 mmol) was added to 0.5 M LiAlH$_4$ in glyme (82 mL, 41 mmol) at 0° C. 4-(2,5-difluorophenyl)-4-methoxycarbonyl-1-methylpiperidine (3.45 g, 12.8 mmol) in glyme (4 mL) was added. Saturated aqueous sodium potassium tartrate (50 mL) was added along with Celite (10 g), and the mixture was mechanically stirred 1 h at room temp. The slurry was filtered, and the organic layer was extracted with 1N HCl. The HCl was washed with EtOAc and then basified with 3N NaOH. The product was extracted with $CH_2Cl_2$, washed with 20% brine, dried ($MgSO_4$), and concentrated to a crude solid, which was recrystallized (EtOAc) to yield 1.46 g (52%) of the title compound as colorless crystals.

$^1H$ NMR (400 MHz, $CDCl_3$) δ 7.28 (dt, 1H, J=7,9 Hz), 6.88 (ddd, 1H, J=3,9,9 Hz), 6.81 (ddd, J=3,9,13 Hz), 3.76 (s, 2H), 2.59 (m, 2H), 2.32–2.20 (m, 4H), 2.23 (s, 3H), 1.96 (t, 2H, J=5 Hz) ppm.

Step 3) 5-Fluoro-1'-methyl-spiro(2,3-dihydrobenzofuran-3,4'-piperidine)

NaH (158 mg, 6.56 mmol) was added to 4-(2,5-difluorophenyl)-4-hydroxymethyl-1-methylpiperidine (1.45 g, 6.56 mmol) in DMF (20 mL). The slurry was heated to 90° C. for 6 h. The reaction was diluted with hexane (200 mL), washed with water (200 mL), brine (50 mL), dried ($MgSO_4$), and concentrated to yield 1.21 g (92%) of the title compound as a white crystalline solid;

$^1H$ NMR (400 MHz, $CDCl_3$) δ 6.98 (dd, 1H), 6.54 (dt, 1H), 6.48 (dd, 1H), 4.37 (s, 2H), 2.84 (m, 2H), 2.31 (s, 3H), 1.97 (4H, pentuplet), 1.71 (m, 2H) ppm.

Step 4) 5-Fluoro-spiro(2,3-dihydrobenzofuran-3,4'-piperidine)hydrochloride salt 5-fluoro-1'-methyl-spiro(2,3-dihydrobenzofuran-3,4'-piperidine) (1.21 g, 5.48 mmol) in 1,2-dichloroethane (12 mL) at room temp was treated with 2-chloroethyl chloroformate (1 mL, 9 mmol). A white precipitate formed, and the reaction was refluxed 2 h. MeOH (12 mL) was added and refluxing was continued for 2 h. The reaction was concentrated to a crude solid, which was triturated with EtOAc (5 mL) and filtered to yield 1.27 g (95%) of the title compound as a white crystalline solid.

$^1H$ NMR (400 MHz, $d_6$-DMSO) δ 9.12 (s, 1H), 9.04 (s, 1H), 7.11 (dd, 1H), 7.74–7.66 (m, 2H), 4.53 (s, 2H), 3.26 (d, 2H), 2.95 (t, 2H), 2.08 (t, 2H), 1. 79 (d, 2H) ppm.

Reaction of 5-fluoro-spiro(2,3-dihydrobenzofuran-3,4'-piperidine)hydrochloride with 3-((S)-(3,4-dichlorophenyl))-4-(N-(t-butoxycarbonyl)-(methylamino))butanal according to the procedure given in Example 8, Method B gave 1'-(3-((S)-(3,4-dichlorophenyl))-4-(N-(t-butoxycarbonyl)-(methylamino))butyl)-5-fluoro-spiro(2,3-dihydrobenzofuran-3,4'-piperidine). Removal of the BOC group and benzamide formation according to the procedure given in Example 3, Steps A and B afforded the compounds listed in Examples 31–36:

EXAMPLE 31

1'-(3-((S)-(3,4-Dichlorophenyl))-4-(N-(3,5-dichlorobenzoyl)(methylamino))butyl)-5-fluoro-spiro(2,3-dihydrobenzofuran-3,4'-piperidine)

Mass spectrum (CI): m/z=611.2 ($^{35}Cl+^{35}Cl$ isotope+$H^+$), 613.2 ($^{37}Cl+^{35}Cl$ isotope+$H^+$).

EXAMPLE 32

1'-(3-((S)-(3,4-Dichlorophenyl))-4-(N-(4-fluoro-1-napthoyl)(methylamino))butyl)-5-fluoro-spiro(2,3-dihydrobenzofuran-3,4'-piperidine)

Mass spectrum (CI): m/z=609.3 ($^{35}Cl+^{35}Cl$ isotope+$H^+$), 611.3 ($^{37}Cl+^{35}Cl$ isotope+$H^+$).

EXAMPLE 33

1'-(3-((S)-(3,4-Dichlorophenyl))-4-(N-(3-chlorobenzoyl)(methylamino))butyl)-5-fluoro-spiro(2,3-dihydrobenzofuran-3,4'-piperidine)

Mass spectrum (CI): m/z=575.2 ($^{35}Cl+^{35}Cl$ isotope+$H^+$), 577.2 ($^{37}Cl+^{35}Cl$ isotope+$H^+$), 579.2 ($^{37}Cl+^{37}Cl$ isotope+$H^+$).

EXAMPLE 34

1'-(3-((S)-(3,4-Dichlorophenyl))-4-(N-(3,5-dimethylbenzoyl)(methylamino))butyl)-5-fluoro-spiro(2,3-dihydrobenzofuran-3,4'-piperidine)

Mass spectrum (CI): m/z=569.3 ($^{35}Cl+^{35}Cl$ isotope+$H^+$), 571.3 ($^{37}Cl+^{35}Cl$ isotope+$H^+$).

EXAMPLE 35

1'-(3-((S)-(3,4-Dichlorophenyl))-4-(N-(3-methylbenzoyl)(methylamino))butyl)-5-fluoro-spiro(2,3-dihydrobenzofuran-3,4'-piperidine)

Mass spectrum (CI): m/z=555.3 ($^{35}Cl+^{35}Cl$ isotope+$H^+$), 557.3 ($^{37}Cl+^{35}Cl$ isotope+$H^+$).

EXAMPLE 36

1'-(3-((S)-(3,4-Dichlorophenyl))-4-(N-(benzoyl)-(methylamino))butyl)-5-fluoro-spiro(2,3-dihydrobenzofuran-3,4'-piperidine)

Mass spectrum (CI): m/z=541.3 ($^{35}Cl+^{35}Cl$ isotope+$H^+$), 543.3 ($^{37}Cl+^{35}Cl$ isotope+$H^+$).

Preparation of spiro(2,3-dihydrobenzofuran-3,4'-piperidine)hydrochloride was carried out by analogy to the procedure given in Example 30, starting with methyl 2-fluorophenylacetate. Reaction of spiro(2,3-dihydrobenzofuran-3,4'-piperidine) hydrochloride with 3-(S)-(3,4-dichlorophenyl)-4-(t-butoxycarbonyl-methylamino)butanal according to the procedure given in Example 8, Step B gave 1'-(3-((S)-(3,4-dichlorophenyl))-4-(N-(t-butoxycarbonyl)-(methylamino))butyl)-spiro(2,3-dihydrobenzofuran-3,4'-piperidine). Removal of the BOC group and benzamide formation according to the procedure given in Example 3, Steps A and B afforded the compounds listed in Examples 37–43:

EXAMPLE 37

1'-(3-((S)-(3,4-Dichlorophenyl))-4-(N-(benzoyl)-(methylamino))butyl)spiro(2,3-dihydrobenzofuran-3,4'-piperidine)

Mass spectrum (CI): m/z=523.1 ($^{35}Cl+^{35}Cl$ isotope+$H^+$).

EXAMPLE 38

1'-(3-((S)-(3,4-Dichlorophenyl))-4-(N-(3-methylbenzoyl)(methylamino))butyl)-spiro(2,3-dihydrobenzofuran-3,4'-piperidine)

Mass spectrum (CI): m/z=537.2 ($^{35}Cl+^{35}Cl$ isotope+$H^+$), 539.2 ($^{37}Cl+^{35}Cl$ isotope+$H^+$).

EXAMPLE 39

1'-(3-((S)-(3,4-Dichlorophenyl))-4-(N-(3,5-dimethylbenzoyl)(methylamino))butyl)-spiro(2,3-dihydrobenzofuran-3,4'-piperidine)

Mass spectrum (CI): m/z=551.2 ($^{35}Cl+^{35}Cl$ isotope+$H^+$), 553.2 ($^{37}Cl+^{35}Cl$ isotope+$H^+$).

EXAMPLE 40

1'-(3-((S)-(3,4-Dichlorophenyl))-4-(N-(3-chlorobenzoyl)(methylamino))butyl)-spiro(2,3-dihydrobenzofuran-3,4'-piperidine)

Mass spectrum (CI): m/z=557.0 ($^{35}Cl+^{35}Cl$ isotope+$H^+$).

EXAMPLE 41

1'-(3-((S)-(3,4-Dichlorophenyl))-4-(N-(3,5-dichlorobenzoyl)(methylamino))butyl)-spiro(2,3-dihydrobenzofuran-3,4'-piperidine)

Mass spectrum (CI): m/z=591.0 ($^{35}Cl+^{35}Cl$ isotope+H$^+$), 593.1 ($^{37}Cl+^{35}Cl$ isotope+H$^+$).

EXAMPLE 42

1'-(3-((S)-(3,4-Dichlorophenyl))-4-(N-(4-fluoro-1-napthoyl)(methylamino))butyl)-spiro(2,3-dihydrobenzofuran-3,4'-piperidine)

Mass spectrum (CI): m/z=591.3 ($^{35}Cl+^{35}Cl$ isotope+H$^+$), 593.2 ($^{37}Cl+^{35}Cl$ isotope+H$^+$).

EXAMPLE 44

1'-(3-((S)-(3,4-Dichlorophenyl))-4-(N-(t-butoxycarbonyl)(methylamino))butyl)-spiro(2,3-dihydrobenzothiophene-3,4'-piperidine)

Step 1) 1-t-Butoxycarbonyl-3-hydroxy-4-methylenepiperidine n-Butyl lithium (9.57 mL, 2.45M in hexane, 23.7 mmol) was added to a −78° C. solution of diisopropylamine (3.32 mL, 23.7 mmol) in THF (15 mL). After 30 min at −78° C., methyl phenyl sulfoxide (3.32 g, 23.7 mmol) in THF (4 mL) was added. The solution was warmed to 0° C. and cooled back down to −78° C. 1-t-butoxycarbonyl-4-piperidinone (4.69 g, 23.7 mmol) in THF (20 mL) was added. The reaction was warmed to room temp, quenched by addition of solid NH$_4$Cl, concentrated in vacuo, and partitioned between H$_2$O (100 mL) and EtOAc (100 mL). The organic layer was washed with H$_2$O (50 mL) brine (50 mL), dried (MgSO$_4$), and concentrated in vacuo. The resultant oil was heated at 80° C. in t-butanol (50 mL) with potassium t-butoxide (3.4g, 30 mmol) for 2 h. Solid NH$_4$Cl was added, and the reaction was concentrated in vacuo and partitioned between H$_2$O (100 mL) and EtOAc (100 mL). The EtOAc was washed with brine (50 mL), dried (MgSO$_4$), concentrated in vacuo and purified by column chromatography (silica gel 60, 0–50% EtOAc/hexane) to yield 4.47 g (79%) of the title compound as a crystalline solid.

$^1$H NMR (400 MHz, DMSO-d$_6$) δ 5.21 (d, 1H), 4.96 (s, 1H), 4.77 (s, 1H), 3.82 (t, 2H), 3.67 (dt, 1H), 2.83 (dt, 1H), 2.77–2.50 (brd d, 1H), 2.26 (dt, 1H), 2.01 (ddd, 1H), 1.38 (s, 9H) ppm.

Step 2) 1-t-Butoxycarbonyl-3,4-didehydro-4-(chloromethyl)piperidine

To 1-t-butoxycarbonyl-3-hydroxy-4-methylenepiperidine (5.329 g, 25.1 mmol) in toluene (120 mL) and 2,6-lutidine (3.1 mL, 26 mmol) at 0° C. was added SOCl$_2$ (2.0 mL, 26 mmol). The reaction was heated at 40° C. for 30 min, cooled to 0° C., washed with 0° C. 1N HCl (100 mL), 0.1 N HCl (100 mL), H$_2$O (100 mL), brine (50 mL), dried (MgSO$_4$), and concentrated in vacuo to afford 5.18 g (89%) of allylic chloride as a yellow oil.

$^1$H NMR (400 MHz, CDCl$_3$) δ 5.78 (s, 1H), 4.04 (s, 2H), 3.95 (s, 2H), 3.55 (t, 2H, J=6 Hz), 2.24 (s, 2H), 1.45 (s, 9H) ppm.

Step 3) 1-t-Butoxycarbonyl-4-((2-bromophenyl)thio)methyl-1,2,5,6-tetrahydropyridine The allylic chloride (330 mg, 1.43 mmole) was dissolved in acetone (10 mL) and 2-bromothiophenol (172 ml, 1.43 mmole) and K$_2$CO$_3$ (390 mg, 2.86 mmoles) were added. The reaction mixture was heated to 60° C. for 1 h and then filtered though silica gel (ether). The organic layer was concentrated in vacuo and purified by column chromatography (silica gel 60, hexanes/ethyl acetate 10/1) to give the title compound in 84% yield (460 mg).

Step 4) 1'-t-Butoxycarbonyl-spiro(2,3-dihydrobenzothiophene-3,4'-piperidine)

The intermediate adduct from step 3 above (450 mg, 1.17 mmole) was dissolved in benzene (60 mL) and AIBN (10 mg) and tributyltin hydride (644 mL, 2.39 mmole) were added. This mixture was refluxed for 2 h and concentrated. The residue was dissolved in Et$_2$O and Br$_2$ was added until the reaction solution turned to a brownish color. To this brownish solution at room temp was added DBU (650 mL) dropwise. The resulting cloudy solution was filtered though silica gel and washed with Et$_2$O. The Et$_2$O solution was concentrated and the residue was purified by radial chromatography (silic gel 60, 10/1 hexanes/EtOAc) to give the title compound (157 mg) in 43% yield.

$^1$H NMR (400 MHz, CDCl$_3$) δ 7.18 (d, 7 Hz, 1H), 7.12 (t, 7 Hz, 1H), 7.06 (m, 2H), 4.11(m, 2H), 3.30 (s, 3H), 2.89 (m, 2H), 1.79 (m, 4H), 1.47 (s, 9H) ppm.

Removal of the BOC group according to the procedure given in Example 3, Step A followed by reaction with 3-((S)-(3,4-dichlorophenyl))-4-(N-(t-butoxycarbonyl)-(methylamino))butanal according to the procedure given in Example 8, Method B gave 1'-(3-((S)-(3,4-dichlorophenyl))-4-(N-(t-butoxycarbonyl)-(methylamino))butyl)-spiro(2,3-dihydrobenzothiophene-3,4'-piperidine). Removal of the BOC group and benzamide formation according to the procedures described in Example 3, Steps A and B gave the compounds listed in Examples 45–46:

EXAMPLE 45

1'-(3-((S)-(3,4-Dichlorophenyl))-4-(N-(3,5-dimethylbenzoyl)(methylamino))butyl)-spiro(2,3-dihydrobenzothiophene-3,4'-piperidine)

Mass spectrum (CI): m/z=567.2 ($^{35}Cl+^{35}Cl$ isotope+H$^+$), 569.2 ($^{37}Cl+^{35}Cl$ isotope+H$^+$).

EXAMPLE 46

1'-(3-((S)-(4-Chlorophenyl))-4-(N-(3,5-dimethylbenzoyl)(methylamino))butyl)-spiro(2,3-dihydrobenzothiophene-3,4'-piperidine)

Mass spectrum (CI): m/z=533 ($^{35}Cl+^{35}Cl$ isotope+H$^+$), 535 ($^{37}Cl+^{35}Cl$ isotope+H$^+$).

EXAMPLE 47

1'-(3-((S)-(3,4-Dichlorophenyl))-4-(N-(t-butoxycarbonyl)(methylamino))butyl)-spiro(2,3-dihydrobenzothiophene-3,4'-piperidine)-1-oxide 1'-(3-((S)-(3,4-Dichlorophenyl))-4-(N-(t-butoxycarbonyl)(methylamino))butyl)-spiro(2,3-dihydrobenzothiophene-3,4'-piperidine) (222 mg, 415 μmol) in CH$_2$Cl$_2$ (500 μL) at −78° C. was treated with a solution of m-chloroperbenzoic acid (86 mg, 498 μmol) in CH$_2$Cl$_2$ (1 mL). The reaction was poured into 0° C. saturated aqueous NaHSO$_3$. The organic layer was washed with saturated aqueous NaHCO$_3$ (1 mL), brine (1 mL), dried (MgSO$_4$), concentrated in vacuo and purified by column chromatography (silica gel 60, 0–100% acetone/CH$_2$Cl$_2$) to yield 54.3 mg (24%) of the title compound as a white foam.

$^1$H NMR (500 MHz, CDCl$_3$) δ 7.84 (d, 1H, J=7.5 Hz), 7.60 (t, 1H, J=7.5 Hz), 7.48 (t, 1H, J=7.5 Hz), 7.44 (m, 1H), 7.39 (dd, 1H, J=2.0, 8.5 Hz), 7.32 (m, 1H), 7.10–7.04

(rotamer multiplets, 1H), 3.6–3.2 (m, 2H), 3.34, 3.32 (two doublets of one diastereomer, 1H), 3.16, 3.14 (two doublets of other diastereomer, 1H), 3.1–2.8 (m, 3H), 2.75–2.65 (rotamer singlets, 3H), 2.3–1.7 (m, 10H), 1.42 (s, 9H) ppm.

EXAMPLE 48

1'-(3-((S)-(3,4-Dichlorophenyl))-4-(N-(4-fluoro-1-napthylmethyl)(methylamino))butyl)-spiro(2,3-dihydrobenzothiophene-3,4'-piperidine)-1-oxide The title compound was prepared by oxidizing 1'-(3-((S)-(3,4-dichlorophenyl))-4-(N-(t-butoxycarbonyl)-(methylamino))butyl)-spiro(2,3-dihydrobenzothiophene-3,4'-piperidine) as described in Example 47 above, and then removing the BOC group and N-benzoylating according to the procedures given in Example 3, Steps A and B.

Mass spectrum (CI): m/z=623.1 ($^{35}Cl+^{35}Cl$ isotope+H$^+$).

EXAMPLE 49

1'-(3-((S)-(3,4-Dichlorophenyl))-4-(N-(t-butoxycarbonyl)(methylamino))butyl)-spiro(2,3-dihydrobenzothiophene-3,4'-piperidine)-1,1-dioxide To 1'-(3-((S)-(3,4-dichlorophenyl))-4-(N-(t-butoxycarbonyl)(methylamino))butyl)-spiro(2,3-dihydrobenzothiophene-3,4'-piperidine) (102 mg, 191 µmol) in MeOH (0.8 mL) at 0° C. was added Oxone (176 mg, 287 µ) in water (0.4 mL). After 30 min at room temp, the reaction was filtered through a plug of silica gel and concentrated to yield 39.5 mg (36%) of the title compound as a white foam.

$^1$H NMR (500 MHz, CDCl$_3$) δ 7.72 (d, 1H, J=7.5 Hz), 7.66 (t, 1H, J=7.5 Hz), 7.51 (t, 1H, J=7.3 Hz), 7.39 (t, 1H, J=8.3 Hz), 3.65–3.25 (m, 2H), 3.38 (s, 2H), 3.15–2.85 (m, 3H), 2.76, 2.66 (rotamer singlets, 3H), 2.25 (m, 2H), 2.15–1.95 (m, 3H), 1.95–1.65 (m, 5H), 1.40 (s, 9H) ppm.

EXAMPLE 50

1'-(3-((S)-(3,4-Dichlorophenyl))-4-(N-(3,5-dimethylbenzoyl)(methylamino))butyl)-spiro(2,3-dihydrobenzothiophene-3,4'-piperidine)-1,1-dioxide The title compound was prepared by removing the BOC group and N-benzoylating (according to the procedures given in Example 3, Steps A and B) the product from Example 49.

Mass spectrum (CI): m/z=639.1 ($^{35}Cl+^{35}Cl$ isotope+H$^+$).

EXAMPLE 51

1'-(3-((S)-(3,4-Dichlorophenyl))-4-(N-(3,5-dimethylbenzoyl)(methylamino))butyl)-spiro(2,3-dihydrobenzothiophene-3,4'-piperidine)-1,1-dioxide To 1'-(3-((S)-(3,4-dichlorophenyl))-4-(N-(3,5-dimethylbenzoyl)(methylamino))butyl)-spiro(2,3-dihydrobenzothiophene-3,4'-piperidine) (10 mg, 20 µmol) in MeOH (0.1 mL) at 0° C. was added 0.4 M aqueous Oxone (75 µL, 30 µmol). The reaction was warmed to room temp and stirred overnight. The reaction was concentrated in vacuo, partitioned between 1N NaOH (1 mL) and CH$_2$Cl$_2$ (1 mL). The organic layer was concentrated and purified by column chromatography (silica gel 60, 0–100% acetone/CH$_2$Cl$_2$) to yield 9.0 mg (90%) of the title compound as a clear film.

Mass spectrum (CI): m/z=599.1 ($^{35}Cl+35Cl$ isotope+H$^+$), 601.1 ($^{37}Cl+^{35}Cl$ isotope+H$^+$).

EXAMPLE 52

1'-(3-((S)-(4-Chlorophenyl))-4-(N-(3,5-dimethylbenzoyl)(methylamino))butyl)-spiro(2,3-dihydrobenzothiophene-3,4'-piperidine)-1,1-dioxide This compound was prepared according to the procedure given in Example 51 above.

Mass spectrum (CI): m/z=567 ($^{35}Cl+^{35}Cl$ isotope+H$^+$), 565 ($^{37}Cl+^{35}Cl$ isotope+H$^+$).

EXAMPLE 53

1'-(3-((S)-(4-Chlorophenyl))-4-(N-(3,5-dimethylbenzoyl)(methylamino))butyl)-spiro(2,3-dihydrobenzothiophene-3,4'-piperidine)-1-oxide To 1'-(3-((S)-(4-chlorophenyl))-4-(N-(3,5-dimethylbenzoyl)(methylamino))butyl)-spiro(2,3-dihydrobenzothiophene-3,4'-piperidine) (25 mg, 47 µmol) in MeOH (1.0 mL) at 0° C. was added a solution of Oxone (38 mg, 61 µmol) in H$_2$O (1.0 mL). The reaction was stirred 2 min and quenched with 10% aqueous sodium bisulfite. The reaction mixture was diluted with H$_2$O (10 mL), neutralized with sat. aqueous NaHCO3 (15 mL), extracted with CH$_2$Cl$_2$ (3×25 mL), washed with brine (10 mL), dried (Na$_2$SO$_4$), concentrated in vacuo, and purified by column chromatography (silica gel 60, 5–8% MeOH/CH$_2$Cl$_2$) to yield 25 mg (99%) of a colorless solid; Mass spectrum (CI): m/z=549 ($^{35}Cl+^{35}Cl$ isotope+H$^+$), 551 ($^{37}Cl+^{35}Cl$ isotope+H$^+$).

EXAMPLE 54

1'-(3-(S)-(4-Chlorophenyl)-4-(N-(3,5-bistrifluoromethylbenzoyl)(methylamino))butyl)-spiro(2,3-dihydrobenzothiophene-3,4'-piperidine), 1-oxide The title compound was prepared by the oxone oxidation method described in Example 53.

Mass Spectrum (CI/NH3) M+H=657, 659 ($^{35,37}Cl$-isotope).

EXAMPLE 55

1'-(3-(S)-(4-Chlorophenyl)-4-(N-(3,5-bistrifluoromethylbenzoyl)(methylamino))butyl)-spiro(2,3-dihydrobenzothiophene-3,4'-piperidine), 1,1-dioxide The title compound was prepared by the oxone oxidation method described in Example 51.

Mass Spectrum (CI/NH3) M+H=673, 675 ($^{35,37}Cl$-isotope).

Substituted indoline spiropiperidine derivatives were obtained by employing substituted phenyl hydrazines and 1-benzyloxycarbonylpiperidine-4-carboxyaldehyde in the Fisher indole synthesis. When regioisomers were formed, they were separated as the 1'-benzyloxycarbonyl-1-methanesulfonyl-spiro(indoline-3,4'-piperidine) derivative by chromatography (silica gel 60, THF/hexane). Preparation of a representative substituted spiro(indoline-3,4'-piperidinium)hydrochloride is described below:

EXAMPLE 56

1'-Benzyloxycarbonyl-5-fluoro-spiro(indoline-3,4'-piperidine)

A slurry of 4-fluorophenylhydrazine hydrochloride (6.504 g, 40 mmol), pyridine (6.56 ml, 80 mmol), toluene (360 mL), acetonitrile (40 mL), and N-benzylcarboxy-4-piperidine carboxyaldehyde (9.88 g, 40 mmol) was maintained at 0° C. for 1 h. Trifluoroacetic acid (18.5 mL, 240 mmol) was added, and the reaction was heated 20 h at 60° C. The reaction was cooled to 0° C., and methanol (40 mL) was added followed by NaBH$_4$ (1.51 g, 40 mmol). The cooling bath was removed and 30% aqueous NH$_4$OH (100 mL) was added. The organic layer was separated, washed with 5% aqueous NH$_4$OH (100 mL) brine (50 mL), dried (MgSO$_4$), and concentrated to a crude oil which was purified by column chromatography (SG 60 silica, 0–5% acetone/CH$_2$Cl$_2$) to yield 6.48 g (48%) of the title compound as a clear oil.

$^1$H NMR (400 MHz, CDCl$_3$): δ 7.23–7.36 (m, 5H), 6.76–6.71 (m, 2H), 6.58 (dd, 1H, J=4.4, 8.0 Hz), 5.14 (s, 2H), 4.12 (br s, 2H), 3.49 (s, 2H), 2.95 (br s, 2H) 1.73 (br s, 4H) ppm.

EXAMPLE 57

Step 1) 1'-Benzyloxycarbonyl-5-fluoro-1-methanesulfonyl-spiro(indoline-3,4'-piperidine)

To a solution of 1'-benzyloxycarbonyl-5-fluoro-spiro (indoline-3,4'-piperidine) (6.48 g, 19.0 mmol) in CH$_2$Cl$_2$ (19 mL) and pyridine (38 mmol, 3.1 mL) at 0° C. was added methanesulfonyl chloride (19 mmol, 1.52 mL). The reaction was warmed to room temp., diluted with ethyl acetate (200 mL), washed with 1N aqueous HCl (100 mL) saturated aqueous NaHCO$_3$ (100 mL) brine (50 mL), dried (MgSO$_4$), and concentrated to 7.81 g (98%) of the title compound as a red foam.

$^1$H NMR (400 MHz, CDCl$_3$) δ 7.35 (m, 5H), 7.32 (dd, 1H, J=4.2, 9.0 Hz), 6.90 (dt, 1H, J=2.7, 8.8 Hz), 6.81 (1H, dd, J=2.6, 8.2 Hz), 5.14 (s, 2H), 4.22 (br s, 2H), 3.84 (s, 2H), 2.92 (br s, 2H), 2.88 (s, 3H), 1.79 (br s, 2H), 1.69 (d, 2H, 13 Hz) ppm.

Step 2) 5-Fluoro-1-methanesulfonyl-spiro(indoline-3,4'-piperidine)hydrochloride salt To 1'-benzyloxycarbonyl-5-fluoro-1-methanesulfonyl-spiro(indoline-3,4'-piperidine) (7.81 g, 18.7 mmol) in CHCl$_3$ (18 mL) at room temp. was added trimethylsilyl iodide (20.5 mmol, 2.93 ml). After 5 min, the rxn was cooled to 0° C., and a 5M solution of HCl in methanol/methyl acetate is added with vigorous stirring. The HCl solution was prepared by adding acetyl chloride (190 mmol, 14 ml) to methanol (20 mL) at 0° C. 40 ml of EtOAc was added, and the slurry was vigorously stirred at 0° C. for 4 h. The solid was filtered off under dry nitrogen, washed with 0° C. ethyl acetate (10 mL) and then with hexane (10 mL), and dried under vacuum to yield 4.77 g (80%) of the title compound as a light pink solid.

$^1$H NMR (400 MHz, DMSO-d$_6$) δ 8.85 (br s, 1H), 8.77 (br s, 1H), 7.26 (dd, 1H, J=4.4, 8.8 Hz), 7.11 (dt, 1H, J=2.8, 8.8 Hz), 7.02 (dd, 1H, J=2.8, 8.4 Hz), 3.97 (s, 3H), 3.30 (m, 2H), 3.06 (m, 2H), 3.06 (s, 3H), 2.04 (m, 2H), 1.83 (d 2H, J=14 Hz) ppm.

The substituted 1-methanesulfonyl-spiro(indoline-3,4'-piperidinium) hydrochlorides could be reductively aminated with 3-(S)-(3,4-dichlorophenyl)-4-(t-butoxycarbonyl-methylamino)butanal according to the procedure described in Example 8, Method B. Removal of the BOC group by the procedure given in Example 3, Step A provided intermediate secondary amine compounds described below which could then be benzoylated under conditions given in Example 3, Step B to give the indicated benzamide derivatives.

EXAMPLE 58

1'-(3-((S)-(3,4-Dichlorophenyl))-4-(methylamino) butyl)-1-methanesulfonyl-5-methoxy-spiro(indoline-3,4'-piperidine)

$^1$H NMR (CDCl$_3$, 400 MHz) δ 7.37 (d, 1H, J=8.2 Hz), 7.29 (d, 1H), 7.25 (d, 1H), 7.04 (dd, 1H, J=2.1, 8.3 Hz), 6.72 (m, 2H), 3.76 (s, 3H), 3.73 (s, 2H), 2.87 (m, 2H), 2.82 (s, 3H), 2.78 (d, 2H, J=7.1 Hz), 2.41 (s, 3H), 2.32–2.18 (m, 2H), 2.05–1.85 (m, 5H), 1.7 (m, 3H) ppm.

EXAMPLE 59

1'-(3-((S)-(3,4-Dichlorophenyl))-4-(methylamino) butyl)-1-methanesulfonyl-5-methyl-spiro(indoline-3, 4'-piperidine)

$^1$H NMR (CDCl$_3$, 400 MHz) δ 7.37 (d, 1H, J=6.2 Hz), 7.30 (d, 1H, J=2.0 Hz), 7.24 (d, 1H, J=10 Hz), 7.05 (dd, 1H, J=2.0, 8.2 Hz), 7.00 (d, 1H, J=8.8 Hz), 6.95 (s, 1H), 3.71 (dd, 2H, J=16, 5.4 Hz), 2.9 (m, 3H), 2.84 (s, 3H), 2.79 (d, 2H, J=7.4 Hz), 2.43 (s, 3H), 2.30 (s, 3H), 2.24 (m, 1H), 2.05–1.85 (m, 5H), 1.75–1.60 (m, 3H) ppm.

EXAMPLE 60

5-Chloro-1'-(3-((S)-(3,4-dichlorophenyl))-4-(methylamino)butyl)-1-methanesulfonyl-spiro (indoline-3,4'-piperidine)

$^1$H NMR (CDCl$_3$, 400 MHz) δ 7.39 (d, 1H, J=8.2 Hz), 7.29 (d, 1H, J=2.1), 7.24 (s, 1H), 7.17 (dd, 1H, J=2.2, 8.5 Hz), 7.11 (d, 1H, J=2.1 Hz), 7.05 (dd, 1H, J=2.0, 8.3 Hz), 3.76 (dd, 2H, J=4.5, 25 Hz), 3.18 (p, 1H), 2.10–2.85 (m, 4H), 2.87 (s, 3H), 2.61 (s, 3H), 2.47 (m, 1H), 2.34 (m, 1H), 2.15 (t, 1H), 2.04 (m, 2H), 1.95–1.70 (m, 5H) ppm.

EXAMPLE 61

1'-(3-((S)-(3,4-Dichlorophenyl))-4-(methylamino) butyl)-5-fluoro-1-methanesulfonyl-spiro(indoline-3, 4'-piperidine)

$^1$H NMR (CDCl$_3$, 400 MHz) δ 7.38 (d, 1H), 7.3 (m, 2H), 7.05 (dd, 1H), 7.91–7.85 (m, 2H), 3.75 (dd, 2H), 3.0–2.8 (m, 3H), 2.81 (d, 2H), 2.43 (s, 3H), 2.42 (m, 1H), 2.34 (m, 1H), 2.1–1.8 (m, 5H), 1.7 (m, 3H) ppm.

EXAMPLE 62

1'-(3-((S)-(3,4-Dichlorophenyl))-4-(methylamino) butyl)-7-fluoro-1-methanesulfonyl-spiro(indoline-3, 4'-piperidine)

$^1$H NMR (CDCl$_3$, 400 MHz) δ 7.38 (d, 1H), 7.29 (d, 1H), 7.05 (m, 2H), 6.95 (m, 2H), 3.99 (dd, 2H), 3.25 (s, 3H), 2.9 (m, 2H), 2.81 (t, 1H), 2.45 (s, 3H), 2.38 (m, 1H), 2.28 (m, 1H), 2.1–1.8 (m, 5H), 1.75 (m, 3H) ppm.

EXAMPLE 63

1'-(3-((S)-(3,4-Dichlorophenyl))-4-(N-(3,5-dimethylbenzoyl)(methylamino))butyl)-1-methanesulfonyl-5-methyl-spiro(indoline-3,4'-piperidine)

Mass spectrum (FAB): m/z=642.0 ($^{35}$Cl+$^{35}$Cl isotope+H$^+$).

EXAMPLE 64

5-Chloro-1'-(3-((S )-(3,4-dichlorophenyl))-4-(N-(3-methylbenzoyl)(methylamino))butyl)-1-methanesulfonyl-spiro(indoline-3,4'-piperidine)

Mass spectrum (FAB): m/z=648.1 ($^{35}$Cl+$^{35}$Cl isotope+H$^+$).

EXAMPLE 65

1'-(3-((S)-(3,4-Dichlorophenyl))-4-(N-(3,5-dimethylbenzoyl)(methylamino))butyl)-1-methanesulfonyl-5-methoxy-spiro(indoline-3,4'-piperidine)

Mass spectrum (FAB): m/z=658 ($^{35}$Cl+$^{35}$Cl isotope+H$^+$).

EXAMPLE 66

1'-(3-((S)-(3,4-Dichlorophenyl))-4-(N-(3-methylbenzoyl)(methylamino))butyl)-5-fluoro-1-methanesulfonyl-spiro(indoline-3,4'-piperidine)

Mass spectrum (CI): m/z=632.2 ($^{35}$Cl+$^{35}$Cl isotope+H$^+$), 634.2 ($^{37}$Cl+$^{35}$Cl isotope+H$^+$).

EXAMPLE 67

1'-(3-((S)-(3,4-Dichlorophenyl))-4-(N-(3,5-dichlorobenzoyl)(methylamino))butyl)-5-fluoro-1-methanesulfonyl-spiro(indoline-3,4'-piperidine)

Mass spectrum (FAB): m/z=688.0 ($^{37}$Cl+$^{35}$Cl isotope+$^{35}$Cl+$^{35}$Cl isotope+H$^+$).

EXAMPLE 68

1'-(3-((S)-(3,4-Dichlorophenyl))-4-(N-(3,5-dimethylbenzoyl)(methylamino))butyl)-5-fluoro-1-methanesulfonyl-spiro(indoline-3,4'-piperidine)

Mass spectrum (CI): m/z=646.1 ($^{35}$Cl+$^{35}$Cl isotope+H$^+$), 648.1 ($^{37}$Cl+$^{35}$Cl isotope+H$^+$).

EXAMPLE 69

1'-(3-((S)-(3,4-Dichlorophenyl))-4-(N-(3-chlorobenzoyl)(methylamino))butyl)-5-fluoro-1-methanesulfonyl-spiro(indoline-3,4'-piperidine)

Mass spectrum (CI): m/z=652.2 ($^{35}$Cl+$^{35}$Cl isotope+$^{35}$Cl+$^{35}$Cl isotope+H$^+$), 656.2 ($^{37}$Cl+$^{35}$Cl isotope+$^{37}$Cl+$^{35}$Cl isotope+H$^+$), 657.2 ($^{37}$Cl+$^{37}$Cl isotope+$^{37}$Cl+$^{35}$Cl isotope+H$^+$), 658.2 ($^{37}$Cl+$^{37}$Cl isotope+$^{37}$Cl+$^{37}$Cl isotope+H$^+$).

EXAMPLE 70

1'-(3-((S)-(3,4-Dichlorophenyl))-4-(N-(3,5-bis(trifluoromethyl)benzoyl)-(methylamino))butyl)-5-fluoro-1-methanesulfonyl-spiro(indoline-3,4'-piperidine)

Mass spectrum (CI): m/z=754.1 ($^{35}$Cl+$^{35}$Cl isotope+H$^+$), 756.1 ($^{37}$Cl+$^{35}$Cl isotope+H$^+$).

EXAMPLE 71

1'-(3-((S)-(3,4-Dichlorophenyl))-4-(N-(3,5-dimethylbenzoyl)(methylamino))butyl)-7-fluoro-1-methane sulfonyl-spiro (indoline-3,4'-piperidine)

Mass spectrum (CI): m/z=646.1 ($^{35}$Cl+$^{35}$Cl isotope+H$^+$), 648.1 ($^{37}$Cl+$^{35}$Cl isotope+H$^+$).

EXAMPLE 72

1-Acetyl-1'-(3-((S)-(3,4-dichlorophenyl))-4-(N-t-butoxycarbonyl)(methylamino))butyl)-5-fluoro-spiro(indoline-3,4'-piperidine)

To 1'-(3-((S)-(3,4-dichlorophenyl))-4-(N-t-butoxycarbonyl)(methylamino))butyl)-5-fluoro-1-methanesulfonyl-spiro(indoline-3,4'-piperidine) (1.32 g 2.15 mmol) in toluene (5 mL) at 0° C. was added 3.4M Red-Al/toluene (5.1 mL, 17.2 mmol). After 4 h at room temp, the reaction was cooled to 0° C. and quenched by cautious addition of 1N aqueous NaOH (2 mL). Cold saturated aqueous sodium potassium tartrate (30 mL) was added, and the biphasic mixture was mechanically stirred at 0° C. for 1 h. The product was extracted with toluene (3×10 mL), washed with 50% saturated aqueous sodium potassium tartrate (10 mL), H$_2$O (10 mL), brine (10 mL), dried (MgSO$_4$), and concentrated to roughly 5 mL volume, and cooled to 0° C. Pyridine (705 μL, 8.6 mmol) and acetic anhydride (410 μL, 4.3 mmol) were added. After 16 hours at room temp, the reaction was concentrated and purified by column chromatography (silica gel 60, 0–50% acetone/CH$_2$Cl$_2$) to yield 830 mg (72%) of the title compound as a white foam.

$^1$H NMR (400 MHz, CDCl$_3$) δ 8.14 (dd, 1H), 7.37 (d, 1H), 7.28 (m, 1H), 7.1–7.0 (m, 1H), 6.87 (m, 2H), 3.95, 3.81 (rotamer singlets, 2H), 3.53 (m, 1H), 3.36 (m, 2H), 3.22 (m, 1H), 3.01 (m, 1H), 2.90 (m, 1H), 2.82 (m, 1H), 2.74, 2.63 (rotamer singlets, 3H), 2.39, 2.20 (rotamer singlets, 3H), 1.89 (m, 4H), 1.65 (m, 4H) ppm.

The corresponding 1-acetyl-spiro(indoline-3,4'-piperidine) compounds were obtained by selectively removing the methanesulfonyl group with Red-Al and then treating with acetic anhydride/pyridine at the stage where the methylamino group is protected with BOC; a representative procedure is given in Example 72 above. The BOC group could be removed using the procedure given in Example 3, step A to give intermediate methylamino compounds which were benzoylated according to Example 3, step B to give the compounds in Examples 73–90:

EXAMPLE 73

1-Acetyl-5-chloro-1'-(3-((S)-(3,4-dichlorophenyl))-4-(methylamino)butyl)-spiro(indoline-3,4'-piperidine)

$^1$H NMR (CDCl$_3$, 400 MHz) δ 7.83 (d, 1H, J=6.6 Hz), 7.12 (d, 1H, J=5.2 Hz), 7.09 (d, 1H, J=2.0 Hz), 6.87 (dd, 2H, J=2.0, 10.0 Hz), 6.84 (s, 1H), 2.81 (p, 1H0, 2.75–2.55 (m, 4H), 2.27 (s, 3H), 2.12 (m, 1H), 2.04 (m, 1H), 1.95 (s, 3H), 1.9–1.7 (m, 3H), 1.6 (t, 2H), 1.5–1.4 (m, 3H) ppm.

EXAMPLE 74

1-Acetyl-1'-(3-((S)-(3,4-dichlorophenyl))-4-(methylamino)butyl)-5-methyl-spiro(indoline-3,4'-piperidine)

$^1$H NMR (CDCl$_3$, 400 MHz) δ 8.05 (d, 1H), 7.38 (d, 1H), 7.30 (d, 1H), 7.05 (dd, 1H), 7.00 (d, 1H), 6.92 (s, 1H), 3.79 (s, 2H), 3.01 (p, 2H), 2.9 (m, 3H), 2.52 (s, 3H), 2.5–2.1 (m, 2H), 2.29 (s, 3H), 2.20 (s, 3H), 2.1–1.7 (m, 6H), 1.65 (m, 2H) ppm.

EXAMPLE 75

1-Acetyl-1'-(3-((S)-(3,4-dichlorophenyl))-4-(methylamino)butyl)-5-fluoro-spiro(indoline-3,4'-piperidine)

$^1$H NMR (CDCl$_3$, 400 MHz) δ 8.14 (dd, 1H), 7.38 (d, 1H), 7.24 (s, 1H), 7.05 (dd, 1H), 6.88 (dt, 1H), 6.82 (dd, 1H). 3.96, 3.83 (rotamer singlets, 2H), 3.13 (p, 1H), 3.04 (dd, 2H), 2.92 (dd, 2H), 2.69, 2.66 (rotamer singlets, 3H), 2.50 (p, 1H), 2.33 (p, 1H), 2.38, 2.20 (rotamer singlets, 3H), 2.13 (t, 1H), 2.05 (m, 1H), 1.7 (m, 4H), 1.73 (dd, 2H) ppm.

EXAMPLE 76

1-Acetyl-1'-(3-((S)-(3,4-dichlorophenyl))-4-(methylamino)butyl)-6-fluoro-spiro(indoline-3,4'-piperidine)

$^1$H NMR (DMSO-d$_6$, 500 MHz) δ 7.76 (dd, 1H), 7.58–7.53 (m, 2H), 7.26 (dd, 1H), 7.21 (dd, 1H), 6.80 (dt,

1H), 3.93 (s, 2H), 2.98–2.86 (m, 3H), 2.82 (d, 1H), 2.65 (d, 1H), 2.38 (s, 3H), 2.19 (m, 1H), 2.16 (s, 3H), 2.09 (m, 1H), 2.05 (t, 1H), 1.90 (t, 2H), 1.78–1.6 (m, 3H), 1.6–1.5 (m, 2H) ppm.

EXAMPLE 77

1-Acetyl-1'-(3-((S)-(3,4-dichlorophenyl))-4-(methylamino)butyl)-4-fluoro-spiro(indoline-3,4'-piperidine)

$^1$H NMR (DMSO-d$_6$, 500 MHz) δ 7.88 (d, 1H), 7.63–7.58 (m, 2H), 7.29 (dd, 1H), 7.19 (q, 1H), 6.79 (t, 1H), 3.86 (s, 2H), 3.23–3.13 (m, 3H), 2.97 (m, 1H), 2.72 (m, 1H), 2.52 (s, 3H), 2.26 (m, 1H), 2.16 (s, 3H), 2.09 (t, 4H), 1.97 (p, 2H), 1.76–1.62 (m, 3H) ppm.

EXAMPLE 78

1-Acetyl-1'-(3-((S)-(3,4-dichlorophenyl))-4-(N-(benzoyl)(methylamino))butyl)-4-fluoro-spiro(indoline-3,4'-piperidine)

Mass spectrum (CI): m/z=588.2 ($^{35}$Cl+$^{35}$Cl isotope+H$^+$).

EXAMPLE 79

1-Acetyl-1'-(3-((S)-(3,4-dichlorophenyl))-4-(N-(3,5,-dimethylbenzoyl)(methylamino))butyl)-6-fluoro-spiro(indoline-3,4'-piperidine)

Mass spectrum (CI): m/z=610.2 ($^{35}$Cl+$^{35}$Cl isotope+H$^+$), 612.2 ($^{37}$Cl+$^{35}$Cl isotope+H$^+$).

EXAMPLE 80

1-Acetyl-1'-(3-((S)-(3,4-dichlorophenyl))-4-(N-(benzoyl)(methylamino))butyl)-6-fluoro-spiro(indoline-3,4'-piperidine)

Mass spectrum (CI): m/z=582.3 ($^{35}$Cl+$^{35}$Cl isotope+H$^+$).

EXAMPLE 81

1-Acetyl-1'-(3-((S)-(3,4-dichlorophenyl))-4-(N-(3,5,-dimethylbenzoyl)(methylamino))butyl)-4-fluoro-spiro(indoline-3,4'-piperidine)

Mass spectrum (CI): m/z=610.3 ($^{35}$Cl+$^{35}$Cl isotope+H$^+$)

EXAMPLE 82

1-Acetyl-1'-(3-((S)-(3,4-dichlorophenyl))-4-(N-(benzoyl)(methylamino))butyl)-5-fluoro-spiro(indoline-3,4'-piperidine)

Mass spectrum (CI): m/z=582.2 ($^{35}$Cl+$^{35}$Cl isotope+H$^+$).

EXAMPLE 83

1-Acetyl-1'-5-chloro-(3-((S)-(3,4-dichlorophenyl))-4-(N-(3,5-dimethylbenzoyl)-(methylamino))butyl)-spiro(indoline-3,4'-piperidine)

Mass spectrum (FAB): m/z=626.0 ($^{35}$Cl+$^{35}$Cl isotope+H$^+$), 628.1 ($^{37}$Cl+$^{35}$Cl isotope+H$^+$).

EXAMPLE 84

1-Acetyl-1'-(3-((S)-(3,4-dichlorophenyl))-4-(N-(3-chlorobenzoyl)(methylamino))butyl)-5-fluoro-spiro(indoline-3,4'-piperidine)

Mass spectrum (CI): m/z 616.2 ($^{35}$Cl+$^{35}$Cl isotope+H$^+$).

EXAMPLE 85

1-Acetyl-1'-(3-((S)-(3,4-dichlorophenyl))-4-(N-(3,5-dichlorobenzoyl)(methylamino))butyl)-5-fluoro-spiro(indoline-3,4'-piperidine)

Mass spectrum (CI): m/z=650.1 ($^{35}$Cl+$^{35}$Cl isotope+H$^+$).

EXAMPLE 86

1-Acetyl-1'-(3-((S)-(3,4-dichlorophenyl))-4-(N-(3-methylbenzoyl)(methylamino))butyl)-5-fluoro-spiro(indoline-3,4'-piperidine)

Mass spectrum (CI): m/z=596.2 ($^{35}$Cl+$^{35}$Cl isotope+H$^+$), 598.3 ($^{37}$Cl+$^{35}$Cl isotope+H$^+$).

EXAMPLE 87

1-Acetyl-1'-(3-((S)-(3,4-dichlorophenyl))-4-(N-(3,5-dimethylbenzoyl)(methylamino))butyl)-5-fluoro-spiro(indoline-3,4'-piperidine)

Mass spectrum (CI): m/z=610.2 ($^{35}$Cl+$^{35}$Cl isotope+H$^+$).

EXAMPLE 88

1-Acetyl-1'-(3-((S)-(3,4-dichlorophenyl))-4-(N-(3-isopropoxybenzoyl)(methylamino))butyl)-5-fluoro-spiro(indoline-3,4'-piperidine)

Mass spectrum (CI): m/z=640.3 ($^{35}$Cl+$^{35}$Cl isotope+H$^+$), 642.3 ($^{37}$Cl+$^{35}$Cl isotope+H$^+$).

EXAMPLE 89

1-Acetyl-1'-(3-((S)-(3,4-dichlorophenyl))-4-(N-(3,5-bis(trifluoromethyl)-(methylamino))butyl)-5-fluoro-spiro(indoline-3,4'-piperidine)

Mass spectrum (CI): m/z=718.2 ($^{35}$Cl+$^{35}$Cl isotope+H$^+$), 720.2 ($^{37}$Cl+$^{35}$Cl isotope+H$^+$).

EXAMPLE 90

1-Acetyl-1'-(3-((S)-(3,4-dichlorophenyl))-4-(N-(3,5-dimethylbenzoyl)(methylamino))butyl)-5-methyl-spiro(indoline-3,4'-piperidine)

Mass spectrum (FAB): m/z=606.1 ($^{35}$Cl+$^{35}$Cl isotope+H$^+$), 608.2 ($^{37}$Cl+$^{35}$Cl isotope+H$^+$).

N-Napthoyl-methylamino derivatives (Examples 91–101) were prepared by analogy to the benzoyl derivatives, employing commercially available 1-napthoyl chlorides in place of benzoyl chlorides:

EXAMPLE 91

1-Acetyl-1'-(3-((S)-(3,4-dichlorophenyl))-4-(N-(4-fluoro-1-napthoyl)(methylamino))butyl)-5-fluoro-spiro(indoline -3,4'-piperidine)

Mass spectrum (CI): m/z=650.3 ($^{35}$Cl+$^{35}$Cl isotope+H$^+$).

EXAMPLE 92

1-Acetyl-1'-(3-((S )-(3,4-dichlorophenyl))-4-(N-(1-napthoyl)(methylamino))butyl)-5-fluoro-spiro(indoline-3,4'-piperidine)

Mass spectrum (CI): m/z=632.2 ($^{35}$Cl+$^{35}$Cl isotope+H$^+$), 634.2 ($^{37}$Cl+$^{35}$Cl isotope+H$^+$).

EXAMPLE 93

1'-(3-((S)-(3,4-Dichlorophenyl))-4-(N-(1-napthoyl)(methylamino))butyl)-5-fluoro-1-methanesulfonyl-spiro(indoline-3,4'-piperidine)

Mass spectrum (CI): m/z=668.2 ($^{35}$Cl+$^{35}$Cl isotope+H$^+$).

EXAMPLE 94

1'-(3-((S)-(3,4-Dichlorophenyl))-4-(N-(4-fluoro-1-napthoyl)(methylamino))butyl)-5-fluoro-1-methanesulfonyl-spiro(indoline-3,4'-piperidine)

Mass spectrum (CI): m/z=668.2 ($^{35}$Cl+$^{35}$Cl isotope+H$^+$).

EXAMPLE 95

1'-(3-((S)-(3,4-Dichlorophenyl))-4-(N-(4-fluoro-1-napthoyl)(methylamino))butyl)-spiro(2,3-dihydrobenzothiophene-3,4'-piperidine)

Mass spectrum (CI): m/z=607.2 ($^{35}$Cl+$^{35}$Cl isotope+H$^+$).

EXAMPLE 96

1'-(3-((S)-(3,4-Dichlorophenyl))-4-(N-(4-fluoro-1-napthoyl)(methylamino))butyl)-spiro(2,3-dihydrobenzothiophene-3,4'-piperidine) sulfone Mass spectrum (CI): m/z=639.1 ($^{35}$Cl+$^{35}$Cl isotope+H$^+$).

EXAMPLE 97

1'-(3-((S)-(3,4-Dichlorophenyl))-4-(N-(4-fluoro-1-napthoyl)(methylamino))butyl)-spiro(2,3-dihydrobenzothiophene-3,4'-piperidine)

Mass spectrum (CI): m/z=623.1 ($^{35}$Cl+$^{35}$Cl isotope+H$^+$).

EXAMPLE 98

1'-(3-((S)-(3,4-Dichlorophenyl))-4-(N-(4-fluoro-1-napthoyl)(methylamino))butyl)-5-fluoro-spiro(2,3-dihydrobenzofuran-3,4'-piperidine)

Mass spectrum (CI): m/z=609.3 ($^{35}$Cl+$^{35}$Cl isotope+H$^+$), 611.3 ($^{37}$Cl+$^{35}$Cl isotope+H$^+$).

EXAMPLE 99

1'-(3-((S)-(3,4-Dichlorophenyl))-4-(N-(4-fluoro-1-napthoyl)(methylamino))butyl)-spiro(2,3-dihydrobenzofuran-3,4'-piperidine)

Mass spectrum (CI): m/z=591.3 ($^{35}$Cl+$^{35}$Cl isotope+H$^+$), 593.3 ($^{37}$Cl+$^{35}$Cl isotope+H$^+$).

EXAMPLE 100

1-Acetyl-1'-(3-((S)-(3,4-dichlorophenyl))-4-(N-(4-fluoro-1-napthoyl)(methylamino))butyl)-6-fluoro-spiro(indoline-3,4'-piperidine)

Mass spectrum (CI): m/z=650.3 ($^{35}$Cl+$^{35}$Cl isotope+H$^+$).

EXAMPLE 101

1-Acetyl-1'-(3-((S)-(3,4-dichlorophenyl))-4-(N-(4-fluoro-1-napthoyl)(methylamino))butyl)-4-fluoro-spiro(indoline-3,4'-piperidine)

Mass spectrum (CI): m/z=650.3 ($^{35}$Cl+$^{35}$Cl isotope+H$^+$).

Benzylamine derivatives could be synthesized by reducing the benzamide of the 1-methanesulfonyl-spiro(indoline-3,4'-piperidine) derivatives described in some of the Examples. The methanesulfonyl group could be removed by heating with HBr/acetic acid/phenol and then be replaced with an acetyl group by treating with acetic anhydride/pyridine. Representative procedures and compounds are given in Examples 102 and 103 below:

EXAMPLE 102

1'-(3-((S)-(3,4-Dichlorophenyl))-4-(N-(4-fluoro-1-napthylmethyl)(methylamino))butyl)-5-fluoro-1-methanesulfonyl-spiro(indoline-3,4'-piperidine)

1'-(3-((S)-(3,4-Dichlorophenyl))-4-(N-(4-fluoro-1-napthoyl)(methylamino))butyl)-5-fluoro-1-methanesulfonyl-spiro(indoline-3,4'-piperidine) (96 mg) was dissolved in 1M Dibal-H in toluene (160 uL). After ½ h, saturated aqueous sodium potassium tartrate (5 mL) and EtOAc (5 mL) were added and stirred vigorously for 2 h. The organic layer was washed with H$_2$O (5 mL), brine (5 mL), dried (MgSO$_4$), and concentrated to a crude oil, which was purified by column chromatography (silica gel 60, 0–10% acetone/CH$_2$Cl$_2$) to yield 55 mg (59%) of the title compound as a white foam; $^1$H NMR (400 MHz, CDCl$_3$) δ 8.09 (d, 1H, J=8.5 Hz), 7.91 (d, 1H, J=8.5 Hz), 7.53 (t, 1H, J=7.5 Hz), 7.38 (t, 1H, J=7.5 Hz), 7.33 (dd, 1H, J=4.3, 8,8 Hz), 7.22 (dd, 1H, J=5.8, 7.8 Hz), 7.18 (d, 1H, J=8.5 Hz), 7.09 (d, J=2.0 Hz), 7.04 (dd, J=7.5, 10. 0 Hz), 6.92 (dt, 1H, J=2.5, 8.5 Hz), 6.88 (d, 1H), 6.77 (dd, 1H, J=1.8, 8.3 Hz), 3.85 (dd, 1H, J=8.0 Hz), 3.76 (s, 2H), 3.75 (dd, 1H, J=8.0 Hz), 2.88 (s, 3H), 2.80–2.66 (m, 3H), 2.62 (dd, 1H, J=8.8, 12.3 Hz), 2.51 (dd, 1H, J=6.5, 12.5 Hz), 2.28 (s, 3H), 2.18–2.06 (m, 2H), 1.88–1.80 (m, 4H), 1.65 (d, 2H, J=10.5 Hz) ppm;

Mass spectrum (CI): m/z=672.4 ($^{35}$Cl+$^{35}$Cl isotope+H$^+$).

EXAMPLE 103

1'-(3-((S)-(3,4-Dichlorophenyl))-4-(N-(4-fluoro-1-napthylmethyl)(methylamino))butyl)-5-fluoro-spiro(indoline-3,4'-piperidine)

1'-(3-((S)-(3,4-dichlorophenyl))-4-(N-(4-fluoro-1-napthylmethyl)(methylamino))butyl)-5-fluoro-1-methanesulfonyl-spiro(indoline-3,4'-piperidine) (45.6 mg) and phenol (19 mg) in 30% HBr/HOAc (270 μL) were heated to 70° C. for 6 h in a sealed vessel. The reaction was concentrated and partitioned between CH$_2$Cl$_2$ (1 ml) and 1N NaOH (2 mL). The organic layer was eluted through a 3×3 cm silica gel plug with 0–100% acetone/CH$_2$Cl$_2$ to yield 30 mg (74%) of the title compound as a yellow oil.

$^1$H NMR (400 MHz, CDCl$_3$) δ 8.09 (d, 1H, J=8.0 Hz), 7.93 (d, 1H, J=8.5 Hz), 7.52 (t, 1H, J=7.5 Hz), 7.43 (t, 1H, J=7.3 Hz), 7.22 (dd, 1H, J=5.5, 7.5 Hz), 7.17 (d, 1H, J=8.5 Hz), 7.06 (dd, 1H, J=8.8, 10.3 Hz), 7.02 (d, 1H, J=1.5 Hz), 6.87 (d, 1H, J=3.5 Hz) 6.78 (dd, 1H, J=2.3, 8.3 Hz), 6.75 (dd, 1H, J=2.3, 7.8 Hz), 6.56 (dd, 1H, J=4.0, 8.5 Hz) ppm;

Mass spectrum (CI): m/z=594.3 ($^{35}$Cl+$^{35}$Cl isotope+H$^+$), 596.3 ($^{37}$Cl+$^{35}$Cl isotope+H$^+$).

EXAMPLE 104

1-Acetyl-1'-(3-((S)-(3,4-dichlorophenyl))-4-(N-(4-fluoro-1-napthylmethyl)-(methylamino))butyl)-5-fluoro-spiro(indoline-3,4'-piperidine)

1'-(3-((S)-(3,4-Dichlorophenyl))-4-(N-(4-fluoro-1-napthylmethyl)(methylamino))butyl)-5-fluoro-spiro (indoline-3,4'-piperidine) (10 mg) in $CH_2Cl_2$ (100 µL) was treated with one drop acetic anhydride and 1 drop pyridine. After 30 min, the reaction was eluted through a 1×2 cm silica gel column using 0–100% acetone/$CH_2Cl_2$ plus 1% $NH_4OH$ to yield 10 mg (93%) of the title compound as a clear film.

$^1$H NMR (CDCl$_3$) δ 8.17 (dd, 1H, J=4.3, 8.8 Hz), 8.09 (d, 1H, J=8.5 Hz), 7.91 (d, 1H, J=8.0 Hz), 7.52 (t, 1H, 7.3 Hz), 7.38 (t, 1H, J=7.3 Hz), 7.22 (dd 1H, 6.8, 7.0 Hz), 7.18 (d, 1H, J=8.8 Hz), 7.07 (d, 1H, J=2.0 Hz), 7.04 (dd, 1H, J=8.0, 10.5 Hz), 6.91 (dt, 1H, J=2.0, 9.0 Hz), 6.86 (dd, 1H, J=2.0, 7.5 Hz), 6.76 (dd, 1H, J=2.0, 8.5 Hz), 3.96, 3.81 (rotamer singlets, 3H), 3.85 (d, 1H, J=13 Hz), 3.75 (d, 1H, J=13 Hz), 2.84 (m, 2H), 2.74 (m, 1H), 2.61 (dd, 1H, J=8.5, 13 Hz), 2.51 (dd, 1H, J=7.0, 13 Hz), 2.43, 2.35 (rotamer singlets, 3H), 2.24 (s, 3H), 2.3–2.2 (m, 3H), 2.0–1.85 (m, 4H), 1.65 (m, 2H), 1.50 (m, 1H) ppm;

Mass spectrum (CI): m/z=636.4 ($^{35}$Cl+$^{35}$Cl isotope+H$^+$), 638.4 ($^{37}$Cl+$^{35}$Cl isotope+H$^+$).

EXAMPLE 105

1'-(5-Fluoroindolyl-3-(2-ethanoyl))-1-methanesulfonyl-spiro(indoline-3,4'-piperidine)

To a solution of 1-methanesulfonyl-spiro(indoline-3,4'-piperidine) hydrochloride (373 mg, 1.23 mmol), 5-fluoroindole-3-acetic acid (500 mg, 2.59 mmol), in DMF (15 mL) at room temp. was added N-methyl morpholine (261 mg, 2.59 mmol), hyroxybenzotriazole (381 mg, 2.82 mmol) and 1-(3-dimethylaminopropyl)-3-ethylcarbodiimide (473 mg, 2.47 mmol). The reaction was stirred 48 h, diluted with $H_2O$ (250 mL), extracted with EtOAc (3×100 mL), washed with $H_2O$ (2×150 mL), brine (150 mL), dried ($Na_2SO_4$), concentrated in vacuo and purified by column chromatography (SG 60 silica, 5% MeOH/$CH_2C_{12}$) to afford 486 mg (89%) of the title compound as a colorless oil.

$^1$H NMR (500 MHz, CDCl$_3$) δ 8.39 (br s, 1H), 7.37 (d, 1H, J=8.2 Hz), 7.34 (dd, 1H, J=9.6, 2.3 Hz), 7.29 (dd, 1H, J=8.9, 4.4 Hz), 7.23 (dt, 1H, J=7.8, 1.2 Hz), 7.14 (d, 1H, J=2.3 Hz), 7.03 (t, 1H, J=7.3 Hz), 6.98 (dt, 1H, J=8.9, 2.5 Hz), 6.87 (d, 1H, J=7.5 Hz), 4.73 (d, 1H, J=13.7 Hz), 3.96 (d, 1H, J=14.0 Hz), 3.82–3.92 (m, 2H), 3.72–3.78 (m, 1H), 3.13 (t, 1H, J=13.4 Hz), 2.91 (s, 3H), 2.73 (t, 1H, J=13.5 Hz), 1.83 (dt, 1H, J=13.5, 4.4 Hz), 1.65–1.75 (m, 2H), 1.52–1.58 (m, 1H), 1.40 (dt, 1H, J=13.0, 4.3 Hz) ppm; Mass spec (CI) m/z 441 (M+H).

EXAMPLE 106

1'-(2-(3-(5-Fluoroindolyl))ethyl))-1-methanesulfonyl-spiro(indoline-3,4'-piperidine)

To a solution of 1'-(5-fluoroindolyl-3-(2-ethanoyl))-1-methanesulfonyl-spiro(indoline-3,4'-piperidine) (100 mg, 0.226 mmol) in $CH_2Cl_2$ (8 mL) at −70° C. was added Dibal-H (1M in THF, 0.91 mL, 0.906 mmol). After 2.5 h the mixture was quenched by addition of 1M NaOH (20 mL), diluted with $CH_2Cl_2$ and stirred vigorously for 15 min. The mixture was extracted with $CH_2Cl_2$ (3×50 mL), washed with brine (50 mL), dried ($Na_2SO_4$), concentrated in vacuo and purified by column chromatography (SG60 silica, 5% MeOH/$CH_2Cl_2$) to afford 66 mg (68%) of the title compound as a colorless solid.

$^1$H NMR (500 MHz, CDCl$_3$) δ 8.20 (br s, 1H), 7.42 (d, 1H, J=8.0 Hz), 7.20–7.30 (m, 4H), 7.06–7.14 (m, 2H), 6.93–6.97 (m, 1H), 3.84 (s, 2H), 3.08 (d, 2H, J=11.7 Hz), 2.94–3.00 (m, 2H), 2.93 (s, 3H), 2.71–2.77 (m, 2H), 2.19 (t, 2H, J=12.3 Hz), 2.07 (dt, 2H, J=13.2, 3.9 Hz), 1.75 (d, 2H, J=13.0 Hz) ppm; Mass spec (CI) m/z 428 (M+H).

EXAMPLE 107

4-Fluoro-3,5-dimethylbenzoic acid

Step 1) 1-Bromo-4-fluoro-3,5-dimethylbenzene

To a mixture of 4-Bromo-2,6-dimethylaniline (8.3 g, 42 mmol) at 5° C. and $H_2O$ (50 mL) was added conc $H_2SO_4$ (6.25 mL). $NaNO_2$ (4.1 g) was added in portions until an excess was indicated by starch iodide paper. Water (30 mL) was added to make the mixture homogeneous. After transferring to a plastic container, HBF$_4$ (50%, 13.7 g) was added dropwise with stirring. The resultant white precipitate was collected by vacuum filtration, washed with $H_2O$ (30 mL), MeOH (30 mL), and Et$_2$O (60 mL), and dried over $P_2O_5$ under vacuum for 16 h. The solid was then heated in a glass flask with an open flame until all the solid had decomposed. The remaining liquid was diluted with Et$_2$O (50 mL) and 0.5 M NaOH (30 mL). The organic layer was separated, washed with 0.5 M NaOH (25 mL), $H_2O$ (25 mL), brine (25 mL), dried (MgSO$_4$), and concentrated in vacuo yielding 6.06 g (72%) of 1-bromo-4-fluoro-3,5-dimethylbenzene as a pale yellow liquid.

$^1$H NMR (500 MHZ, CDCl$_3$) δ 7.17 (d, 2H, J=6.2 Hz), 2.21 (s, 6H) ppm.

Step B) 4-Fluoro-3,5-dimethylbenzoic acid

To a mixture of magnesium shavings (120 mg, 4.92 mmol) in THF (2 mL) was added a crystal of iodine followed by slow addition of a solution of the bromide (1.0 g, 4.92 mmol) in THF (3 mL). The reaction mixture was heated to reflux for 1 h followed by cooling to room temp. and addition of $CO_2$(s) (excess), stirred 1 h and quenched by addition of 1M HCl (10 mL). The mixture was extracted with Et$_2$O (3×25 mL), washed with brine (25 mL), dried (MgSO$_4$), and concentrated in vacuo to afford 0.82 g (99%) of the title compound as a pale yellow solid.

$^1$H NMR (500 MHz, CDCl$_3$) δ 7.81 (d, 2H, J=6.7 Hz), 2.36 (s, 6H) ppm.

Mass spec (CI) m/z 168 (M—H).

The compounds of Examples 108–120 were prepared as per Example 3 Step B utilizing the previously prepared amines and the appropriate benzoic or naphthoic acids:

EXAMPLE 108

1'-(3-((S)-(3,4-Dichlorophenyl))-4-(N-(3-chloro-4-fluorobenzoyl)(methylamino))butyl)-1-methanesulfonyl-spiro(indoline-3,4'-piperidine)

Mass spec (CI) 656 ($^{37}$Cl+$^{35}$Cl isotope+H$^+$), 654 ($^{35}$Cl+$^{35}$Cl isotope+H$^+$).

EXAMPLE 109

1'-(3-((S)-(3,4-Dichlorophenyl))-4-(N-(3-chloro-4-fluorobenzoyl)(methylamino))butyl)-5-fluoro-1-methanesulfonyl-spiro(indoline-3,4'-piperidine)

Mass spec (CI) 674 ($^{37}$Cl+$^{35}$Cl isotope+H$^+$), 672 ($^{35}$Cl+$^{35}$Cl isotope+H$^+$).

EXAMPLE 110

1'-(3-((S)-(3,4-Dichlorophenyl))-4-(N-(4-fluorobenzoyl)(methylamino))butyl)-1-methanesulfonyl-spiro(indoline-3,4'-piperidine)

Mass spec (CI) 620 ($^{37}$Cl+$^{35}$Cl isotope+H$^+$), 618 ($^{35}$Cl+$^{35}$Cl isotope+H$^+$).

EXAMPLE 111

1'-(3-((S)-(3,4-Dichlorophenyl))-4-(N-(4-fluorobenzoyl)(methylamino))butyl)-5-fluoro-1-acetyl-spiro(indoline-3,4'-piperidine)

Mass spec (CI) 618 ($^{37}$Cl+$^{35}$Cl isotope+H$^+$), 616 ($^{35}$Cl+$^{35}$Cl isotope+H$^+$).

EXAMPLE 112

1'-(3-((S)-(3,4-Dichlorophenyl))-4-(N-(3-chloro-4-fluorobenzoyl)(methylamino))butyl)-5-fluoro-1-acetyl-spiro(indoline-3,4'-piperidine)

Mass spec (CI) 636 ($^{37}Cl+^{35}Cl$ isotope+H$^+$), 634 ($^{35}Cl+^{35}Cl$ isotope+H$^+$).

EXAMPLE 113

1'-(3-((S)-(3,4-Dichlorophenyl))-4-(N-(4-fluoro-3,5-dimethylbenzoyl)(methylamino))butyl)-5-fluoro-1-acetyl-spiro(indoline-3,4'-piperidine)

Mass spec (CI) 630 ($^{37}Cl+^{35}Cl$ isotope+H$^+$), 628 ($^{35}Cl+^{35}Cl$ isotope+H$^+$).

EXAMPLE 114

1'-(3-((S)-(3,4-Dichlorophenyl))-4-(N-(4-fluoro-3,5-dimethylbenzoyl)(methylamino))butyl)-1-methanesulfonyl-spiro(indoline-3,4'-piperidine)

Mass spec (CI) 648 ($^{37}Cl+^{35}Cl$ isotope+H$^+$), 646 ($^{35}Cl+^{35}Cl$ isotope+H$^+$).

EXAMPLE 115

1'-(3-((S)-(3,4-Dichlorophenyl))-4-(N-(4-fluoro-3-trifluoromethylbenzoyl)-(methylamino))butyl)-1-methanesulfonyl-spiro(indoline-3,4'-piperidine)

Mass spec (CI) 688 ($^{37}Cl+^{35}Cl$ isotope+H$^+$), 686 ($^{35}Cl+^{35}Cl$ isotope+H$^+$).

EXAMPLE 116

1'-(3-((S)-(3,4-Dichlorophenyl))-4-(N-(4-fluoro-3,5-dimethylbenzoyl)(methylamino))butyl)-1-acetyl-spiro(indoline-3,4'-piperidine)

Mass spec (CI) 612 ($^{37}Cl+^{35}Cl$ isotope+H$^+$), 610 ($^{35}Cl+^{35}Cl$ isotope+H$^+$).

EXAMPLE 117

1'-($^3$-((S)-(3,4-Dichlorophenyl))-4-(N-(4-fluoro-3-trifluoromethylbenzoyl)-(methylamino))butyl)-1-acetyl-spiro(indoline-3,4'-piperidine)

Mass spec (CI) 652 ($^{37}Cl+^{35}Cl$ isotope+H$^+$), 650 ($^{35}Cl+^{35}Cl$ isotope+H$^+$).

EXAMPLE 118

1'-(3-((S)-(3,4-Dichlorophenyl))-4-(N-(4-fluoro-1-naphthoyl)(methylamino))butyl)-1-acetyl-spiro(indoline-3,4'-piperidine)

Mass spec (CI) 634 ($^{37}Cl+^{35}Cl$ isotope+H$^+$), 632 ($^{35}Cl+^{35}Cl$ isotope+H$^+$).

EXAMPLE 119

1'-(3-((S)-(3,4-Dichlorophenyl))-4-(N-(4-fluoro-1-naphthoyl)(methylamino))butyl)-1-methanesulfonyl-spiro(indoline-3,4'-piperidine)

Mass spec (CI) 670 ($^{37}Cl+^{35}Cl$ isotope+H$^+$), 668 ($^{35}Cl+^{35}Cl$ isotope+H$^+$).

EXAMPLE 120

1'-(3-((S)-(3,4-Dichlorophenyl))-4-(N-(1-naphthoyl)(methylamino))butyl)-1-acetyl-spiro(indoline-3,4'-piperidine)

Mass spec (CI) 616 ($^{37}Cl+^{35}Cl$ isotope+H$^+$), 614 ($^{35}Cl+^{35}Cl$ isotope+H$^+$).

EXAMPLE 121

1'-(3-((S)-(3,4-Dichlorophenyl))-4-(N-(3,5-dimethylbenzoyl)(methylamino))-4-phenyl-butyl)-1-methanesulfonyl-spiro(indoline-3,4'-piperidine)

The title compound was prepared in 6 steps from 2-(S)-(3,4-dichlorophenyl)-4-pentenoic acid using procedures identical to those in Example 10, substituting phenyllithium for methyllithium in Example 10, Step 2.

Mass Spectrum (FAB): m/z 704 (M+H, $^{37}Cl+^{35}Cl$ isotope, 100%), 706 (M+H, $^{37}Cl+^{37}Cl$ isotope, 80%).

EXAMPLE 122

1'-(4-(N-(3,5-Dimethylbenzoyl)-(methylamino))-4-(phenyl)butyl)-1-acetyl-spiro(indoline-3,4'-piperidine)

The title compound was prepared in 6 steps from 4-pentenoic acid using procedures identical to those in Example 10, substituting phenyllithium for methyllithium in Example 10, Step 2.

Mass Spectrum (FAB): m/z 524 (M+H, $^{37}Cl+^{35}Cl$ isotope, 100%), 526 (M+H, $^{37}Cl+^{37}Cl$ isotope, 50%).

EXAMPLE 123

1'-(3-((S)-(3,4-Dichlorophenyl))-4-(1-(2-phenylimidazolo))butyl)-1-methanesulfonyl-spiro(indoline-3,4'-piperidine)

Step 1) 1-(2-Phenylimidazolo)-2-((S)-(3,4-dichlorophenyl))-4-pentene

To a solution of 0.178 g (0.77 mmole) of 2-((S)-(3,4-dichlorophenyl))-4-penten-1-ol (prepared in Example 136, Step A) and 0.099 mL (0.85 mmole) of 2,6-lutidine in 1.5 mL of methylene chloride at −53 deg C. under nitrogen was added 0.136 mL (0.81 mmole) of trifluoromethanesulfonic anhydride. The solution was stirred between −30 deg C. and −40 deg C. for 15 min at which point 0.333 g (2.31 mmole) of 2-phenylimidazole was added. The temperature was allowed to warm to −20 deg C. briefly, and the mixture was then cooled to −60 deg C., stirred at that temperature for 1 hr, stirred at −20 deg C. for 2 hr, and then held at 4 deg C. for 16 hr. After stirring at room temperature for 8 hr, the mixture was treated with 10 mL of saturated sodium carbonate solution and 10 mL of ethyl acetate and the layers were separated. The aqueous phase was extracted with 2×15 mL of ethyl acetate and the combined aqueous layers were dried over sodium sulfate, filtered and concentrated in vacuo. The residue was partly purified by flash chromatography on 36 g of silica eluting with 500 mL of 3:100 methanol:methylene chloride then 300 mL of 5:100:0.1 methanol:methylene chloride:ammonia water. The partly purified product fractions were flash chromatographed on 66 g of silica eluting with 1.2 L of 83:17 methylene chloride::ethyl acetate to give 85 mg (31%) of an oil.

$^1$H-NMR (400 MHz, CDCl$_3$) δ 2.26 (app. t, 2H), 2.85 (pentet, 1H), 4.08 (dd, 1H), 4.27 (dd, 1H), 4.9–5.0 (m, 2H), 5.45–5.55 (m, 1H), 6.59 (dd, 1H), 6.79 (s, 1H), 6.85 (d, 1H), 7.18 (d, 1H), 7.23–7.30 (m, 2H), 7.35–7.4 (m, 3H).

Mass Spectrum (FAB): m/z 359 (M+H, 65%), 357 (M+H, 100%), 145 (7%).

Step 2) 1'-(2-((S)-(3,4-Dichlorophenyl))-1-(1-(2-phenylimidazolo))-4-butyl)-1-methanesulfonyl-spiro (indoline-3,4'-piperidine)

The title compound was prepared by employing the chemistry outlined in Examples 1 and 2, using 1-(2- phenylimidazolo)-2-((S)-(3,4-dichlorophenyl))-3-butene in place of 3-(S)-(3,4-dichlorophenyl)-4-methylamino-1-pentene, and beginning with the osmium tetroxide step.

$^1$H-NMR (400 MHz, CDCl$_3$) δ 1.55–2 (m, 8H), 2.08 (t, J=7.3, 2H), 2.63 (br d, J=11, 1H), 2.70 (br d, J=8.3, 1H), 2.86 (s, 3H), 2.9–3.0 (m, 1H), 3.71 (s, 2H), 4.13 (dd, J=14, 8.8, 1H), 4.25 (dd, J=14, 6.2, 1H), 6.66 (dd, J=6.2, 2.1, 1H), 6.79 (d, J=1.3, 1H), 6.94 (d, J=2.1, 1H), 7.03 (d, J=1.3, 1H), 7.05 (d, J=6.4, 1H), 7.15 (d, J=6.5, 1H), 7.15–7.25 (m, 2H), 7.35–7.45 (m, 6H)

Mass Spectrum (FAB): m/z 609 (M+H, 25%), 279 (100%), 267 (50%), 212 (30%), 187 (35%).

EXAMPLE 124

1'-(3-((S)-(3,4-Dichlorophenyl))-4-((N-(R or S)-(3,5-dimethylbenzoyl)(methylamino))pentyl)-1-acetyl-spiro(indoline-3,4'-piperidine)

The title compound was prepared in 6 steps from (2S)-(3,4-dichlorophenyl)-4-pentenoic acid using procedures identical to those in Example 10, substituting 1-acetyl-spiro (indoline-3,4'-piperidine) for 1-methanesulfonyl-spiro (indoline-3,4'-piperidine) in Example 10, Step 6.

Mass Spectrum (FAB): m/z 606 (M+H, $^{37}$Cl+$^{35}$Cl isotope, 100%), 608 (M+H, $^{37}$Cl+$^{37}$Cl isotope, 80%).

EXAMPLE 125

1'-(3-((S)-(3,4-Dichlorophenyl))-4-((N-(R or S)-(4-fluoro-1-napthyl)(methylamino))pentyl)-1-acetyl-spiro(indoline-3,4'-piperidine)

The title compound was prepared in 6 steps from (2S)-(3,4-dichlorophenyl)-4-pentenoic acid using procedures identical to those in Example 10, substituting 1-acetyl-spiro (indoline-3,4'-piperidine) for 1-methanesulfonyl-spiro (indoline-3,4'-piperidine) in Example 10, Step 6, and substituting 4-fluoro-1-napthoyl chloride for benzoyl chloride.

Mass Spectrum (FAB): m/z 646 (M+H, $^{37}$Cl+$^{35}$Cl isotope, 30%), 204 (100%).

The following compounds described in Examples 126–129 were prepared by the method described in Scheme II and in Example 10, except that in step 2 ethylmagnesium chloride or propylmagnesium chloride was used at room temperature instead of methyllithium at −78° C.

EXAMPLE 126

1'-(3-((S)-(3,4-Dichlorophenyl))-4-(R or S)-(N-(3,5-dimethylbenzoyl)-(methylamino))hexyl)-1-acetyl-spiro(indoline-3,4'-piperidine)

$^1$H-NMR (400 MHz, CDCl$_3$) δ 0.97 (t, 3H), 2.20 (s, 6H), 2.21 (s, 3H), 2.42–2.46 (s+m, 4H), 6.23 (s, 2H), 6.89 (s, 1H), 7.04 (t, 1H), 7.15–7.21 (m, 3H), 7.39 (t, 2H), 8.18 (d, 1H).

Mass Spectrum (FAB) m/z 620 (m$^+$).

EXAMPLE 127

1'-(3-((S)-(3,4-Dichlorophenyl))-4-(R or S)-(N-(3,5-dimethylbenzoyl)-(methylamino))hexyl)-1-acetyl-5-fluoro-spiro(indoline-3,4'-piperidine)

$^1$H-NMR (400 MHz, CDCl$_3$) δ 0.96 (t, 3H), 2.20 (s, 9H), 2.45 (s, 3H), 3.81 (s, 2H), 6.24 (s, 2H), 6.84–6.89 (m, 3H), 7.19 (dd, 1H), 7.39 (t, 2H), 8.13 (dd, 1H).

Mass Spectrum (FAB) m/z 638 (m$^+$).

EXAMPLE 128

1'-(3-(S)-(3,4-Dichlorophenyl)-4-(R or S)-(N-(3,5-dimethylbenzoyl)-(methylamino))heptyl)-1-acetyl-spiro(indoline-3,4'-piperidine)

$^1$H-NMR (400 MHz, CDCl$_3$) δ 0.96 (t, 3H), 2.20 (s, 6H), 2.21 (s, 3H), 2.41–2.45 (s+m, 4H), 3.78 (s, 2H), 6.22 (s, 2H). 6.89 (s, 1H), 7.03 (t, 1H), 7.15–7.21 (m, 3H), 7.39 (t, 2H), 8.18 (d, 1H).

Mass Spectrum (FAB): m/z 634 (m$^+$).

EXAMPLE 129

1'-(3-(S)-(3,4-Dichlorophenyl)-4-(R or S)-(N-(3,5-dimethylbenzoyl)-(methylamino))heptyl)-1-acetyl-5-fluoro-spiro(indoline-3,4'-piperidine)

$^1$H-NMR (400 MHz, CDCl$_3$) δ 0.97 (t, 3H), 2.20 (s, 9H), 2.44 (s, 3H), 3.81 (s, 2H), 6.22 (s, 2H), 6.83–6.88 (m, 3H), 7.18 (dd, 1H), 7.38 (t, 2H), 8.13 (dd, 1H).

Mass Spectrum (FAB) m/z 652 (m$^+$).

EXAMPLE 130

1'-(3-((S)-(3,4-Dichlorophenyl))-4-(R or S)-hydroxy-5-(3,5-dimethylphenyl)pentyl)-1-methanesulfonyl-spiro(indoline-3,4'-piperidine)

To a THF (3 mL) solution of 3,5-dimethylbenzylmagnesium chloride (generated from 290 mg (1.9 mmol) of 3,5-dimethylbenzyl chloride and 53 mg (2.2 mmol) of magnesium in THF) was added slowly 1'-(3-((S)-(3,4-dichlorophenyl))-3-(N-methoxy-N-methylaminocarbonyl)propyl)-1-methanesulfonyl-spiro (indoline-3,4'-piperidine) (100 mg, 0.19 mmol, prepared by reacting the product obtained in Example 10, Step 1 under the oxidative cleavage conditions given in Example 1 followed by the coupling procedure given in Example 2) in 1 mL of THF. The reaction mixture was stirred at 60° C. for 40 min and poured into 20 mL of 1N HCl. The solution was extracted with 3×10 mL of EtOAc. The organic extracts were combined, dried, and concentrated. The product was purified by preparative TLC (30% EtOAc in CH$_2$Cl$_2$) to afford 20 mg of ketone.

To a MeOH (3 mL) solution of ketone (19.4 mg) was added sodium borohydride (7 mg). The mixture was stirred at 55° C. for 1 h and concentrated. The residue was purified by preparative TLC (4% MeOH in CH$_2$Cl$_2$) to give 15 mg of the higher R$_f$ isomer (Isomer A) and 4 mg of a lower R$_f$ isomer (Isomer B).

$^1$H-NMR (400 MHz, CDCl$_3$), Isomer A: d 1.71 (d, 2H), 1.92–2.12 (m, 6H), 2.23–2.29 (s+m, 9H), 2.50–2.60 (m, 2H), 2.72–2.76 (m, 1H), 2.88 (s, 3H). 2.95 (d, 2H), 3.76 (s, 2H), 4.00–4.06 (m, 2H), 6.69 (s, 2H), 6.83 (s, 1H), 7.05 (d, 1H), 7.19–7.24 (m, 3H), 7.37 (t, 2H), 7.44 (s, 1H).

Mass spectrum (FAB) Isomer A, m/z 601 (m$^+$), 603 (m$^+$+2).

$^1$H-NMR (400 MHz, CDCl$_3$), Isomer B: d 1.69 (d, 2H), 1.74–1.79 (m, 1H), 1.83–1.90 (m, 1H), 1.93–2.05 (m, 2H), 2.07–2.20 (m, 2H), 2.24–2.36 (s+m, 8H), 2.42–2.47 (m, 1H), 2.55–2.58 (dd, 1H), 2.66–2.72 (d+dd, 2H), 2.87 (s, 3H), 2.86–3.00 (m, 2H), 3.76 (s, 2H), 3.91–3.95 (m, 1H), 6.72 (s, 2H), 6.82 (s, 2H), 7.13–7.19 (m, 2H), 7.18–7.21 (m, 2H), 7.36 (t, 2H).

Mass spectrum (FAB) Isomer B, m/z 601 (m$^+$) 603 (m$^+$+2).

EXAMPLE 131

1'-(3-(R)-(3,4-Dichlorophenyl)-5-(N-3,5-dimethylphenylmethylamino)-5-oxo-pentyl)-1-methanesulfonyl-spiro(indoline-3,4'-piperidine)

Step 1) Diazomethyl-(2-(S)-(3,4-dichlorophenyl)-pent-4-en-yl)-ketone

To a solution of 2-(S)-(3,4-dichlorophenyl)-pent-4-enoic acid (5.04 g, 20.6 mmol) in 60 mL of dichloromethane was added oxalyl chloride 2.15 mL (24.6 mmol) and dimethylformamide (0.1 mL) upon cooling in an ice-water bath. The cooling bath was then removed and the reaction mixture was stirred at rt overnight. The solvent was removed under reduced pressure. The resulting material was ethyl acetate and concentrated in vacuo in order to remove residual HCl. The residual crude acid chloride was dissolved in 70 mL of ether and was slowly added to a 100 mL ether solution of diazomethane (77 mmol). After stirring for 2 hr at rt, the solvent was removed under vacuum.

The resulting yellow oil was chromatographed on silica gel column eluting with a gradient of hexane:ethyl acetate= 20:1 to 3:1 to give 4.66 g (84%) of diazomethyl-(2-(S)-(3, 4-dichlorophenyl)-pent-4-en-yl)-ketone.

$^1$H-NMR (CDCl$_3$ 400 MHz): δ 2.44(app. quint. 1H), 2.82(app. qunit. 1H), 3.43(br s. 1H), 4.98 & 5.02 (d of AB quart., 2H), 5.16 (br s, 1H), 5.63(m, 1H), 7.09 (dd, J=2.2 Hz, 8.3 Hz, 1H), 7.34(d, J=2.2 Hz, 1H), 7.38 (d J=8.3 Hz).

Step 2) 3-(R)-(3,4-Dichlorophenyl)-hex-4-en-oic acid

To a solution of the above diazoketone 4.56 g (17.0 mmol) in 340 mL of tetrahydrofuran was added 170 mL aqueous solution of silver nitrate 3.02 g (17.8 mmol). After stirring at rt overnight, tetrahydrofuran was removed under reduced pressure. The remaining aqueous layer was extracted with two 100 mL portions of dichloromethane. The combined organic phases were washed with brine, dried over anhydrous magnesium sulfate, filtered, and concentrated. The resulting material was purified by silica gel column chromatography. Elution with dichloromethane:methanol=10:1 gave 3.94 g (90%) of 3-(R)-(3,4-dichlorophenyl)-hex-4-en-oic acid.

Step 3) (N-(3,5-Dimethylphenyl)-N-methyl)-((3-(R)-(3,4-dichlorophenyl)-hex-5-en-yl)-amide The carboxylic acid from Step 2 (300 mg, 1.16 mmol) was dissolved in 5 mL of dichloromethane. To it was added 0.131 mL (1.50 mmol) of oxalyl chloride followed by the addition of a drop of dimethylformamide upon cooling in an ice-water bath. The cooling bath was then removed and the reaction mixture was stirred at rt for 2 hr. The solvent and residual HCl was removed as described above. The resulting crude acid chloride was then dissolved in 5 mL of dichloromethane. To it was added N-methyl-3,5-dimethylaniline 313 mg (3.32 mmol) (Prepared from 3,5-Dimethylaniline following the procedure of Barluenga J., Bayon A. M., and Asensio G. J. Chem. Soc. Chem. Comm. 1984 1334.) followed by the addition of triethylamine 0.5 mL (3.6 mmol) upon cooling in an ice-water bath. Then the cooling bath was removed and the reaction mixture was stirred at rt overnight. The solvent was removed under reduced pressure. The residual solid material was dissolved in 15 mL of ethyl acetate and 5 mL of water. The organic phase was separated and aqueous phase was extracted with two 7 mL portions of ethyl acetate. The combined organic phases were washed with brine, dried over anhydrous magnesium sulfate, filtered, and concentrated. This crude material was chromatographed on silica gel eluting with a gradient of 10:1 to 3:1 hexane-ethyl acetate to give 386 mg of (N-(3,5-dimethylphenyl)-N-methyl)-((3-(R)-(3,4-dichlorophenyl)-hex-5-en-yl)-amide (88%).

$^1$H-NMR(CDCl$_3$ 400 MHz): δ 2.15–2.35 (m., 4H), 2.29 (s, 6H), 3.09 (s, 3H), 3.26 (quint, J=7.2 Hz, 1H), 4.88 (d, J=7.6 Hz, 1H), 4.92 (s, 1H), 5.5 (m, 1H), 6.45 (s, 2H), 6.91 (dd, J=2 Hz, 7 Hz, 1H), 6.93 (s, 1H), 7.30 (d, J=8.3 Hz, 1H).

Step 4) 3-(R)-(3,4-Dichlorophenyl)-5-(N-(3,5-dimethylphenyl)methylamino)-5-oxo-pentanal To 386 mg (1.03 mmol) of the product from the previous step was oxidized by osmium tetroxide to corresponding diol as described in Example 1 to give 413 mg of crude diol.

381 mg of this material was then dissolved in 10 mL of benzene. To it was added lead tetraacetate 452 mg (1.02 mmol). After stirring for 1 hr at rt, 5 mL of water was added to quench the reaction. The reaction mixture was extracted with two 10 mL portions of ethyl acetate. The combined organic phases were dried over anhydrous magnesium sulfate, filtered, and concentrated. The crude material was chromatographed on silica gel eluting with hexane:ethyl acetate=2:1 to give 329 mg of 3-(R)-(3,4-dichlorophenyl)-5-(N-(3,5-dimethylphenyl)-methylamino)-5-oxo-pentanal (94% over two steps).

Step 5) 1'-(3-(R)-(3,4-Dichlorophenyl)-5-(N-3,5-dimethylphenylmethylamino)-5-oxo-pentyl)-1-methanesulfonyl-spiro(indoline-3,4'-piperidine)

Following the procedure described in Example 2, 107 mg (0.287 mmol) of this aldehyde was treated with 1-methanesulfonyl-spiro(indoline-3,4'-piperidine) hydrochloride to give 103 mg (58% yield) of the title compound.

$^1$H-NMR (CDCl$_3$ 400 MHz): δ 2.23 (s, 6H), 2.86 (s, 3H), 3.09 (s, 3H), 3.72 (s, 2H), 6.49 (s, 2H), 6.9–7.2 (s, 8H).

MS(CI): 628 (M$^+$+1: $^{35}$Cl×2), 630 (M$^+$+1: $^{35}$Cl & $^{37}$Cl)

EXAMPLE 132

1'-(3-(R)- (3,4-Dichlorophenyl))-5-(3,5-dimethylphenyl)-5-oxo-pentyl)-1-methanesulfonyl-spiro(indoline-3,4'-piperidine)

Step 1) (N-Methoxy-N-methyl)-(3-(R)-(3,4-dichlorophenyl)-4-hexenyl)-amide

To a solution of 3-(R)-(3,4-dichlorophenyl)-5-hexenoic acid (Example 132, Step 1) 744 mg (2.87 mmol) was added 1-hydroxybenzotriazole hydrate 465 mg (3.44 mmol), and 1-(3-dimethylaminopropyl)-3-ethylcarbodiimide hydrochloride 660 mg (3.44 mmol) with cooling in an ice-water bath. The cooling bath was then removed. After stirring at rt for 1 hr, to it was added 5 mL dichloromethane suspension of N,O-dimethylhydroxyl amine hydrochloride 840 mg (8.61 mmol) and triethylamine 1.2 mL (8.6 mmol). After stirring overnight, the solvent was removed under vacuum, diluted with ethyl acetate and water. The organic phase was separated. Aqueous phase was extracted twice with ethyl acetate. Combined organic phases were washed with brine, dried over anhydrous magnesium sulfate, filtered, concentrated, chromatographed on silica gel eluting on a gradient of hexane:ethyl acetate=5:1 to 2:1 to give 762 mg (88%) of (N-methoxy-N-methyl)-(3-(R)-(3,4,-dichlorophenyl)-4-hexenyl)-amide.

$^1$H-NMR (CDCl$_3$ 400 MHz): δ 2.34(m, 1H), 2.69 (App. d, 2H), 3.09 (s, 3H), 3.23 (quint. J=7.3 Hz, 1H), 3.56 (s, 3H), 4.95 (s, 1H), 4.98 (app. d, 1H), 5.6 (m, 1H), 7.0 (dd, J=2.1 Hz, 8.4 Hz, 1H), 7.28 (d, J=2.1 Hz, 1H), 7.32 (d, J=8.3 Hz, 1H).

Step 2) 3-(R)-(3,4-Dichlorophenyl)-(N-methoxymethylamino)-5-oxo-pentanal

This above material was subjected to the osmium tetroxide oxidation to the corresponding diol as described in Example 1. The crude product was then treated with 1.23 g (2.77 mmol) of lead tetraacetate as described in example 131, Step 4. Chromatographic purification on silica gel (eluant; dichloromethane:ethyl acetate=5:1) afforded 618 mg (81% two steps) of 3-(R)-(3,4-dichlorophenyl)-(N-methoxy-methylamino)-5-oxo-pentanal.

Step 3) 1'-(3-(R)-(3,4-Dichlorophenyl)-5-(N-methoxymethylamino)-5-oxo-pentyl)-1-methanesulfonyl-spiro (indoline-3,4'-piperidine)

A sample of 332 mg (1.09 mmol) of the aldehyde from Step 2 above was subjected to reductive amination with 1-methanesulfonyl-spiro(indoline-3,4'-piperidine) hydrochloride as described in Example 2 to give 369 mg (61%) of 1'-(3-(R)-(3,4-dichlorophenyl)-5-(N-methoxy)-N-(methyl)amino)-5-oxo-pentyl)-1-methanesulfonyl-spiro(indoline-3,4'-piperidine).

$^1$H-NMR (CDCl$_3$ 400 MHz): δ 2.87 (s 3H), 3.10 (s, 3H), 3.60 (s, 3H), 7.0–7.4 (m, 7H).

Step 4) 1'-(3-(R)-(3,4-Dichlorophenyl))-5-(3,5-dimethylphenyl)-5-oxo-pentyl)-1-methanesulfonyl-spiro(indoline-3,4'-piperidine)

To a 1.2 mL THF solution of the amide from Step 3 above (73 mg, 0.13 mmol) was added 1.1 mL of 0.7M 3,5-dimethylphenylmagnesium bromide solution in THF (prepared from 5-bromo-m-xylene and magnesium turnings in THF). Then the reaction mixture was heated to 50° C. After stirring for 1.5 hr, the reaction mixture was allowed to cool down to rt and the reaction was quenched by sat NH$_4$Cl aq solution. THF was removed under reduced pressure, diluted with ethyl acetate. The organic phase was separated and the aqueous phase was extracted twice with ethyl acetate. Combined organic phases were dried over anhydrous magnesium sulfate, filtered, concentrated, chromatographed on silica gel eluting with a gradient of dichloromethane:ethyl acetate=10:1 to 1:1 to give 55 mg (70%) of the title compound.

$^1$H-NMR (CDCl$_3$ 400 MHz): δ 2.34 (s, 6H), 2.86 (s, 3H), 3.23 (m, 2H), 3.74 (s, 2H), 7.0–7.5 (m, 10H).

MS (CI): 599 (M$^+$+1: $^{35}$Cl×2), 601 (M$^+$+1: $^{35}$Cl & $^{37}$Cl).

EXAMPLE 133

1'-(3-(R)-(3,4-Dichlorophenyl)-6-(3,5-dimethylphenyl)-5-oxo-hexyl)-1-methanesulfonyl-spiro(indoline-3,4'-piperidine)

70 mg (0.126 mmol) of 1'-(3-(R)-(3,4-dichlorophenyl)-5-(N-methoxy)-N-(methyl)amino)-5-oxo-pentyl)-1-methanesulfonyl-spiro(indoline-3,4'-piperidine) (Example 132, Step 3) was treated with 0.8M THF solution of 3,5-dimethyl benzylmagnesium chloride as in the case of Example 132. The crude material was chromatographed on silica gel in the same solvent system to afford 33 mg of the title compound (43%).

$^1$H-NMR (CDCl$_3$ 400 MHz): δ 2.24 (s, 6H), 2.86 (s, 3H), 3.47 (s, 2H), 3.72 (s, 2H), 6.64 (s, 2H), 6.8–7.4 (m, 8H).

MS (CI): 613 (M$^+$+1: $^{35}$Cl×2), 615 (M$^+$+1: $^{35}$Cl & $^{37}$Cl).

EXAMPLE 134

1'-(3-(S)-(3,4-Dichlorophenyl)-6-(3,5-dimethylphenyl)-6-oxo-hexyl)-1-methanesulfonyl-spiro(indoline-3,4'-piperidine)

3-(R)-(3,4-Dichlorophenyl)-4-hexenoic acid (Example 131, Step 2) was converted into 4-(S)-(3,4-Dichlorophenyl)-5-heptenoic acid as in Example 131, Steps 1 and 2. 4-(S)-(3,4-dichlorophenyl)-4-heptenoic acid was converted to (N-methoxyl-N-methyl)-(4-(S)-(3,4-dichlorophenyl)-6-heptenyl)-amide followed by treatment with 3,5-dimethylphenylmagnesium bromide as described in Example 132, Step 4 to give the title compound.

1H-NMR (CDCl$_3$ 400 MHz): δ 2.32 (s, 6H), 2.80 (s, 3H), 3.74 (s, 3H), 7.0–7.4 (m, 10H).

MS (CI): 613 (M$^+$+1: $^{35}$Cl×2), 615 (M$^+$+1: $^{35}$Cl & $^{37}$Cl).

EXAMPLE 135

1'-(3-(S)-(3,4-Dichlorophenyl)-6-(3,5-dimethylphenyl)-5-(RS)-methyl-6-oxo-hexyl)-1-methanesulfonyl-spiro(indoline-3,4'-piperidine)

Step 1) 4-(S)-(3,4-Dichlorophenyl)-1-(3,5-dimethylphenyl)-hept-6-ene-1-one 1.42 g (4.50 mmol) of (N-Methoxy-N-methyl)-(4-(S)-(3,4-dichlorophenyl)-6-heptenyl)-amide (prepared in Example 134) was dissolved in 20 mL of dry THF. To it added 10 mL THF solution of 3,5-dimethylphenylmagnesium bromide prepared from 1.8 g (9.6 mmol) of 5-bromo-m-xylene and 463 mg of magnesium turnings. After stirring for 2 hr at rt, the reaction was quenched with saturated aqueous ammonium chloride solution. THF was removed under reduced pressure. The residual material was diluted with ethyl acetate. The organic phase was separated, aqueous phase was extracted twice with ethyl acetate. Combined organic phases were washed with brine, dried over anhydrous magnesium sulfate, filtered, concentrated, chromatographed on silica gel eluting with a gradient of hexane ethyl acetate= 10:1 to 5:1 to give 1.57 g of 4-(S)-(3,4-dichlorophenyl)-1-(3,5-dimethylphenyl)-hept-6-ene-1-one (97%).

Step 2) 4-(R)-(3,4-Dichlorophenyl)-1-(3,5-dimethylphenyl)-2-(RS)-methyl-hept-6-ene-1-one Hexamethyldisilazane (0.108 mL, 0.512 mmol), and 0.089 mL of hexamethylphosphoramide were dissolved in 2 mL of dry THF. To it was added 0.306 mL (0.49 mmol) of n-butyllithium (1.6M hexane solution) after cooling in an ice-water bath. After stirring for 20 min, the ice-water bath was replaced by a dry ice-acetone bath and 2 mL of a dry THF solution of 4-(S)-(3,4-dichlorophenyl)-1-(3,5-dimethylphenyl)-hept-6-ene-1-one (154 mg, 0.426 mmol) was added via syringe. After stirring for 1 hr, 0.066 mL (1.06 mmol) of iodomethane was added. The cooling bath was removed and the mixture stirred at rt overnight. The solvent was then removed under reduced pressure and the residual material was diluted in ethyl acetate and water. The organic phase was separated. The aqueous phase was extracted twice with ethyl acetate. The combined organic phases were washed with brine, dried over anhydrous magnesium sulfate, filtered, concentrated, and chromatographed on silica gel eluting with a gradient of hexane:ethyl acetate=10:1 to 7:1 to give 150 mg of 4-(R)-(3,4-dichlorophenyl)-1-(3,5-dimethylphenyl)-2-(R & S)-methyl-hept-6-ene-1-one (94%). This was a 1 to 1 mixture of two diastereomers as revealed by proton NMR.

$^1$H-NMR (CDCl$_3$ 400 MHz): δ 1.06 (d, J=7 Hz, 1.5H), 1.14 (d, J=6.7 Hz, 1.5H), 2.30, 2.31 (s, 6H), 2.5 (m, 0.5H), 2.6 (m, 0.5H), 3.1–3.2 (m, 1H), 4.9 (m, 2H), 5.5 (m, 1H), 6.8–7.4 (m, 6H).

Step 3) 3-(S)-(3,4-Dichlorophenyl)-5-(RS)-methyl-6-(3,5-dimethylphenyl)-6-oxo-hexanal The product from Step 2 above was subjected to osmium tetroxide oxidation followed by the treatment with sodium periodate as described in Example 1 to give 3-(S)-(3,4-dichlorophenyl)-5-(RS)-methyl-6-(3,5-dimethylphenyl)-6-oxo-hexanal.

Step 4) 1'-(3-(S)-(3,4-Dichlorophenyl)-6-(3,5-dimethylphenyl)-5-(RS)-methyl-6-oxo-hexyl)-1-methanesulfonyl-spiro(indoline-3,4'-piperidine)

This product from Step 3 above was subjected to reductive amination with 1-methanesulonyl-spiro(indoline-3,4'-piperidine) as described in Example 2 to give the title compound.

$^1$H-NMR (CDCl$_3$ 400 MHz): δ 1.05 (d, J=7 Hz), 1.08 (d, J=6.7 Hz), 2.30 & 2.32 (s, 6H), 2.89 (s, 3H), 3.72 (S, 2H), 6.8–7.0 (m, 10H).

MS (CI): 627 (M$^+$+1: $^{35}$Cl×2), 629 (M$^+$+1: $^{35}$Cl & $^{37}$Cl).

EXAMPLE 136

1'-(3-(S)-(3,4-Dichlorophenyl)-4-(3,5-(bistrifluoromethyl)benzyloxy)-1-acetyl-spiro(indoline-3,4'-piperidine)

Step A: 2-(S)-(3,4-Dichlorophenyl)-4-penten-1-ol

To a solution of 2-(S)-(3,4-dichlorophenyl)-4-pentenoic acid (7.0 gm) (prepared as described by J. Hale et. al., *Bioorganic & Medicinal Chemistry Letters* 1993, 3, 319–322.) in ether (5 mL) at r.t. was added portionwise over 5 min solid lithium aluminum hydride (700 mg). The reaction was heated to 40° C. for 3 hr and then stirred at r.t. for 16 hr.

The reaction was poured into water containing 25 mL of 2N NaOH and extracted twice with ether. The ether layers were washed with brine, combined and dried over $Na_2SO_4$. Flash chromatography afforded the title compound (4.5 gm) as an oil. [α]D=+14 (EtOH, c=1.5).

Step B: 2-(S)-(3,4-Dichlorophenyl)-1-(3,5-(bistrifluoromethyl)benzyloxy)-4-pentene To a solution of 2-(S)-(3,4-dichlorophenyl)-4-penten-1-ol (1.0 gm) in DMF (25 mL) was added sodium hydride (175 mg) while cooled in an ice bath. After 1 min, 3,5-(bistrifluoromethyl)benzyl bromide (2.0 gm) was added followed by a second portion of sodium hydride (175 mg). After 1 hr, the reaction was poured into water and extracted twice with ether. The ether layers were washed with brine, combined and dried over $Na_2SO_4$. Flash chromatography (hexanes, then 2 and 5% ethyl acetate/hexanes) afforded the title compound (2.0 gm) as an oil.

NMR ($CDCl_3$): δ 2.30–2.40 and 2.50–2.60 (2 m, 2H), 2.90–3.00 (m, 1H), 3.55–3.65 (d of AB q, 2H, J=6 and 9 Hz), 4.54 (AB q, 2H, J=13 Hz), 4.90–5.00 (m, 2H), 5.55–5.70 (m, 1H), 7.04 (dd, 1H, J=2 and 8 Hz), 7.30 (d, 1 h, J=2 Hz), 7.36 (d, 1 h, J=8 Hz), 7.64 (s, 2 h), 7.76 (s, 1H).

Step C: 3-(S)-(3,4-Dichlorophenyl)-4-(3,5-(bistrifluoromethyl)benzyloxy)butan-1-ol A solution of 2-(S)-(3,4-dichlorophenyl)-1-(3,5-(bistrifluoromethyl)benzyloxy)-4-pentene (1.5 gm) in methanol (50 mL) was cooled to –70° C. in a dry ice/acetone bath and ozone bubbled thru for 15 min until a blue coloration was seen. The solution was purged with $N_2$ for 10 min and sodium borohydride was added. The reaction was allowed to warm to r.t. and was stirred for 2 hr. The volatiles were removed in vacuo and the residue was flash chromatographed (30 then 50% ethyl acetate/hexanes) to give the title compound as a clear oil.

NMR ($CDCl_3$): δ 1.78–1.88 and 2.00–2.10 (2 m, 2H), 3.05–3.15 (m, 1H), 3.45–3.55 (m, 1H), 3.55–3.68 (2 m, 3H), 4.55 (AB q, 2H, J=13 Hz), 7.04(dd, 1H, J=2 and 8 Hz), 7.32 (d, 1 h, J=2 Hz), 7.36(d, 1 h, J=8 Hz), 7.65 (s, 2 h), 7.76 (s, 1H).

Step D: 4-Bromo-2-(S)-(3,4-dichlorophenyl)-1-(3,5-(bistrifluoromethyl)benzyloxy)butane 3-(S)-(3,4-Dichlorophenyl)-4-(3,5-(bistrifluoromethyl)benzyloxy)butan-1-ol from Step C (500 mg) was converted to the title compound (530 mg) with $Ph_3P-Br_2$ as described in Example 20, Step B.

Step E: 1'-(3-(S)-(3,4-Dichlorophenyl)-4-(3,5-(bistrifluoromethyl)benzyloxy)-1-acetyl-spiro(indoline-3,4'-piperidine)

4-Bromo-2-(S)-(3,4-dichlorophenyl)-1-(3,5-(bistrifluoromethyl)benzyloxy)butane (30 mg) from Step D was converted to the title compound (42 mg) as described in Example 20, Step C.

NMR ($CDCl_3$): δ 1.48–2.05 (m, 10H), 2.14 and 2.34 (2 s, 3H), 2.10–2.25 (m, 2H), 2.70–2.85 (m, 2H), 2.90 (m, 1H), 3.48–3.58 (m, 2H), 3.70 and 3.84 (2 s, 2H), 4.55 (AB q, 2H, J=13 Hz), 6.90–7.15 (m, 4 h), 7.33 (d, 1 h, J=2 Hz), 7.37 (d, 1 h, J=8 Hz), 7.66 (s, 2 h), 7.76 (s, 1H), 8.18 (d, 1 h, 8 Hz).

What is claimed is:

1. A compound selected from the group consisting of:
(a) 1'-(3-((S)-(3,4-dichlorophenyl))-4-(N-t-(butoxycarbonyl)(methylamino))butyl)-1-methanesulfonyl-spiro(indoline-3,4'-piperidine);
(b) 1'-(3-((S)-(3,4-dichlorophenyl))-4-(N-(3,5-dimethylbenzoyl)(methylamino))butyl)-1-methanesulfonyl-spiro(indoline-3,4'-piperidine);
(c) 1'-(3-((S)-(3,4-dichlorophenyl))-4-(N-(benzoyl)(methylamino))butyl)-1-methanesulfonyl-spiro(indoline-3,4'-piperidine);
(d) 1'-(3-((S)-(3,4-dichlorophenyl))-4-(N-(3,5-bistrifluoromethylbenzoyl)(methylamino))butyl)-1-methanesulfonyl-spiro(indoline-3,4'-piperidine);
(e) 1'-(3-((S)-(3,4-dichlorophenyl))-4-(N-(3-methylbenzoyl)(methylamino))butyl)-1-methanesulfonyl-spiro(indoline-3,4'-piperidine);
(f) 1'-(3-((S)-(3,4-dichlorophenyl))-4-(N-(3-chlorobenzoyl)(methylamino))butyl)-1-methanesulfonyl-spiro(indoline-3,4'-piperidine);
(g) 1'-(3-((S)-(3,4-dichlorophenyl))-4-(N-(3-trifluoromethylbenzoyl)(methylamino))butyl)-1-methanesulfonyl-spiro(indoline-3,4'-piperidine);
(h) 1'-(3-((S)-(3,4-dichlorophenyl))-4-(N-(3,5-dichlorobenzoyl)(methylamino))butyl)-1-methanesulfonyl-spiro(indoline-3,4'-piperidine);
(i) 1'-(3-((S)-(3,4-dichlorophenyl))-4-(N-(3-trifluoromethylphenylacetyl)(methylamino))butyl)-1-methanesulfonyl-spiro(indoline-3,4'-piperidine);
(j) 1'-(3-((S)-(3,4-dichlorophenyl))-4-(N-(3-isopropyloxyphenylacetyl)(methylamino))butyl)-1-methanesulfonyl-spiro(indoline-3,4'-piperidine);
(k) 1'-(3-((S)-(3,4-dichlorophenyl))-4-(N-(benzenesulfonyl)(methylamino))butyl)-1-methanesulfonyl-spiro(indoline-3,4'-piperidine);
(l) 1'-(3-((S)-(3,4-dichlorophenyl))-4-(N-(3,5-dimethylbenzoyl)(methylamino))butyl)-1-benzyoxycarbonyl-spiro(indoline-3,4'-piperidine);
(m) 1'-(3-((S)-(3,4-dichlorophenyl))-4-(N-(3,5-dimethylbenzoyl)(methylamino))butyl)-spiro(indoline-3,4'-piperidine);
(n) 1'-(3-((S)-(3,4-dichlorophenyl))-4-(N-(3,5-dimethylbenzoyl)(methylamino))butyl)-1-propionyl-spiro(indoline-3,4'-piperidine);
(o) 1'-(3-((S)-(3,4-dichlorophenyl))-4-(N-(3,5-dimethylbenzoyl)(methylamino))butyl)-1-formyl-spiro(indoline-3,4'-piperidine);
(p) 1'-(3-((S)-(3,4-dichlorophenyl))-4-(N-(3,5-dimethylbenzoyl)(methylamino))butyl)-1-t-butylcarbonyl-spiro(indoline-3,4'-piperidine);
(q) 1'-(3-((S)-(3,4-dichlorophenyl))-4-(N-(3,5-dimethylbenzoyl)(methylamino))butyl)-1-methylaminocarbonyl-spiro(indoline-3,4'-piperidine);
(r) 1'(3-((S)-(3,4-dichlorophenyl))-4-(N-(3,5-dimethylbenzoyl)(methylamino))butyl)-1-ethoxycarbonyl-spiro(indoline-3,4'-piperidine);
(s) 1'(3-((S)-(3,4-dichlorophenyl))-4-(N-(3,5-dimethylbenzoyl)(methylamino))butyl)-1-ethanesulfonyl-spiro(indoline-3,4'-piperidine);
(t) 1'(3-((S)-(3,4-dichlorophenyl))-4-(N-(3,5-dimethylbenzoyl)(methylamino))butyl)-1-1-propanesulfonyl-spiro(indoline-3,4'-piperidine);
(u) 1'(3-((S)-(3,4-dichlorophenyl))-4-(N-(3,5-dimethylbenzoyl)(methylamino))butyl)-1'-methyl-1-methanesulfonyl-spiro-indoline-3,4'-piperidinium iodide;
(v) 1'-(3-(S)-(3,4-dichlorophenyl)-4-(N-(R or S)-(3-methylbenzoyl)(methylamino))pentyl)-1-methanesulfonyl-spiro(indoline-3,4'-piperidine);
(w) 1'-(3-(S)-(3,4-dichlorophenyl)-4-(N-(R or S)-(3,5-bis(trifluoromethyl)benzoyl)(methylamino))pentyl)-1-methanesulfonyl-spiro(indoline-3,4'-piperidine);
(x) 1'-(3-(S)-(3,4-dichlorophenyl)-4-(N-(R or S)-(3,5-dimethylbenzoyl)(methylamino))pentyl)-1-methanesulfonyl-spiro-(indoline-3,4'-piperidine);

(y) 1'-(3-(S)-(3,4-dichlorophenyl)-4-(N-(R or S)-(3,5-dichlorobenzoyl)(methylamino))pentyl)-1-methanesulfonyl-spiro-(indoline-3,4'-piperidine);

(z) 1'-(3-((S)-(3,4-dichlorophenyl))-4-(N-(3,5-difluorobenzoyl)(methylamino))butyl)-1-methanesulfonyl-spiro(indoline-3,4'-piperidine);

(aa) 1'-(3-((S)-(3,4-dichlorophenyl))-4-(N-(3-fluoro-5-(trifluoromethyl)benzoyl)(methylamino))butyl)-1-methanesulfonyl-spiro(indoline-3,4'-piperidine);

(ab) 1'-(3-((S)-(3,4-dichlorophenyl))-4-(N-(1-naphthoyl)(methylamino))butyl)-1-methanesulfonyl-spiro(indoline-3,4'-piperidine);

(ac) 1'-(3-((S)-(3,4-dichlorophenyl))-4-(N-(2-chlorophenylsulfonyl)-(methylamino))butyl)-1-methylsulfonyl-spiro(indoline-3,4'-piperidine);

(ad) 1'-(3-((S)-(3,4-dichlorophenyl))-4-(N-(3-chlorophenylsulfonyl)-(methylamino))butyl)-1-methylsulfonyl-spiro(indoline-3,4'-piperidine);

(ae) 1'-(3-((S)-(3,4-dichlorophenyl))-4-(N-(4-chlorophenylsulfonyl)-(methylamino))butyl)-1-methylsulfonyl-spiro(indoline-3,4'-piperidine);

(af) 1'-(3-((S)-(3,4-dichlorophenyl))-4-(N-(3,5-dichlorophenylsulfonyl)-(methylamino))butyl)-1-methylsulfonyl-spiro(indoline-3,4'-piperidine);

(ag) 1'-(3-((S)-(3,4-dichlorophenyl))-4-(N-(3-fluoro-5-(trifluoromethyl)benzoyl)(methylamino))butyl)-1-acetyl-spiro(indoline-3,4'-piperidine);

(ah) 1'-(3-((S)-(3,4-dichlorophenyl))-4-(N-(3,5-dimethylbenzoyl)(methylamino))butyl)-1-acetyl-spiro(indoline-3,4'-piperidine);

(ai) 1'-(3-((S)-(3,4-dichlorophenyl))-4-(N-(3-bromo-5-methylbenzoyl)(methylamino))butyl)-1-methanesulfonyl-spiro(indoline-3,4'-piperidine);

(aj) 1'-(3-((S)-(3,4-Dichlorophenyl))-4-(N-(3,5-dimethylbenzoyl)(methylamino))butyl)-1-(2-aminoacetyl)-spiro(indoline-3,4'-piperidine); and (ak) 1'-(3-((S)-(3,4-dichlorophenyl))-4-(N-(3,5-dimethylbenzoyl)(methylamino))butyl)-1-methyl-spiro(indol-2-one-3,4'-piperidine).

2. A compound according to claim 1 selected from the group consisting of:

(a) 1'-(3-(S)-(3,4-dichlorophenyl)-4-(N-t-butoxycarbonyl)(methylamino))butyl)-1-methanesulfonyl-spiro(indoline-3,4'-piperidine);

(b) 1'-(3-((S)-(3,4-dichlorophenyl))-4-(N-(3,5-dimethylbenzoyl)(methylamino))butyl)-1-methanesulfonyl-spiro(indoline-3,4'-piperidine);

(c) 1'-(3-((S)-(3,4-dichlorophenyl))-4-(N-(benzoyl)(methylamino))butyl)-1-methanesulfonyl-spiro(indoline-3,4'-piperidine);

(d) 1'-(3-((S)-(3,4-dichlorophenyl))-4-(N-(3,5-bistrifluoromethylbenzoyl)(methylamino))butyl)-1-methanesulfonyl-spiro(indoline-3,4'-piperidine);

(e) 1'-(3-((S)-(3,4-dichlorophenyl))-4-(N-(3-methylbenzoyl)(methylamino))butyl)-1-methanesulfonyl-spiro(indoline-3,4'-piperidine);

(f) 1'-(3-((S)-(3,4-dichlorophenyl))-4-(N-(3-chlorobenzoyl)(methylamino))butyl)-1-methanesulfonyl-spiro(indoline-3,4'-piperidine);

(g) 1'-(3-((S)-(3,4-dichlorophenyl))-4-(N-(3-trifluoromethylbenzoyl)(methylamino))butyl)-1-methanesulfonyl-spiro(indoline-3,4'-piperidine);

(h) 1'-(3-((S)-(3,4-dichlorophenyl))-4-(N-(3,5-dichlorobenzoyl)(methylamino))butyl)-1-methanesulfonyl-spiro(indoline-3,4'-piperidine);

(i) 1'-(3-((S)-(3,4-dichlorophenyl))-4-(N-(3-trifluoromethylphenylacetyl)(methylamino))butyl)-1-methanesulfonyl-spiro(indoline-3,4'-piperidine);

(j) 1'-(3-((S)-(3,4-dichlorophenyl))-4-(N-(3-isopropyloxyphenylacetyl)(methylamino))butyl)-1-methanesulfonyl-spiro(indoline-3,4'-piperidine);

(k) 1'-(3-((S)-(3,4-dichlorophenyl))-4-(N-(benzenesulfonyl)(methylamino))butyl)-1-methanesulfonyl-spiro(indoline-3,4'-piperidine);

(l) 1'-(3-((S)-(3,4-dichlorophenyl))-4-(N-(3,5-dimethylbenzoyl)(methylamino))butyl)-1-benzyoxycarbonyl-spiro(indoline-3,4'-piperidine);

(m) 1'-(3-((S)-(3,4-dichlorophenyl))-4-(N-(3,5-dimethylbenzoyl)(methylamino))butyl)-spiro(indoline-3,4'-piperidine);

(n) 1'-(3-((S)-(3,4-dichlorophenyl))-4-(N-(3,5-dimethylbenzoyl)(methylamino))butyl)-1-acetyl-spiro(indoline-3,4'-piperidine);

(o) 1'-(3-((S)-(3,4-dichlorophenyl))-4-(N-(3,5-dimethylbenzoyl)(methylamino))butyl)-1-propionyl-spiro(indoline-3,4'-piperidine);

(p) 1'-(3-((S)-(3,4-dichlorophenyl))-4-(N-(3,5-dimethylbenzoyl)(methylamino))butyl)-1-formyl-spiro(indoline-3,4'-piperidine);

(q) 1'-(3-((S)-(3,4-dichlorophenyl))-4-(N-(3,5-dimethylbenzoyl)(methylamino))butyl)-1-t-butylcarbonyl-spiro(indoline-3,4'-piperidine);

(r) 1'-(3-((S)-(3,4-dichlorophenyl))-4-(N-(3,5-dimethylbenzoyl)(methylamino))butyl)-1-methylaminocarbonyl-spiro(indoline-3,4'-piperidine);

(s) 1'(3-((S)-(3,4-dichlorophenyl))-4-(N-(3,5-dimethylbenzoyl)(methylamino))butyl)-1-ethoxycarbonyl-spiro(indoline-3,4'-piperidine);

(t) 1'(3-((S)-(3,4-dichlorophenyl))-4-(N-(3,5-dimethylbenzoyl)(methylamino))butyl)-1-ethanesulfonyl-spiro(indoline-3,4'-piperidine);

(u) 1'(3-((S)-(3,4-dichlorophenyl))-4-(N-(3,5-dimethylbenzoyl)(methylamino))butyl)-1-1-propanesulfonyl-spiro(indoline-3,4'-piperidine);

(v) 1'(3-((S)-(3,4-dichlorophenyl))-4-(N-(3,5-dimethylbenzoyl)(methylamino))butyl)-1'-methyl-1-methanesulfonyl-spiro-indoline-3,4'-piperidinium iodide;

(w) 1'-(3-(S)-(3,4-dichlorophenyl)-4-(N-(R or S)-(3-methylbenzoyl)(methylamino))pentyl)-1-methanesulfonyl-spiro(indoline-3,4'-piperidine);

(x) 1'-(3-(S)-(3,4-dichlorophenyl)-4-(N-(R or S)-(3,5-bis(trifluoromethyl)benzoyl)(methylamino))pentyl)-1-methanesulfonyl-spiro(indoline-3,4'-piperidine);

(y) 1'-(3-(S)-(3,4-dichlorophenyl)-4-(N-(R or S)-(3,5-dimethylbenzoyl)(methylamino))pentyl)-1-methanesulfonyl-spiro-(indoline-3,4'-piperidine); and (z) 1'-(3-(S)-(3,4-dichlorophenyl)-4-(N-(R or S)-(3,5-dichlorobenzoyl)(methylamino))pentyl)-1-methanesulfonyl-spiro-(indoline-3,4'-piperidine).

* * * * *

UNITED STATES PATENT AND TRADEMARK OFFICE
CERTIFICATE OF CORRECTION

PATENT NO. : 6,013,652
DATED : January 11, 2000
INVENTOR(S) : Malcolm MacCoss, Sander G. Mills, Shrenik K. Shah, Yuan-Ching P. Chiang, Patrick T. Dunn, Hiroo Koyama It is certified that error appears in the above-identified patent and that said Letters Patent is hereby corrected as shown below:

Title page,
The names of the inventors are amended to add:
Albert J. Robichaud

Signed and Sealed this

Twenty-first Day of August, 2001

*Attest:*

*Nicholas P. Godici*

NICHOLAS P. GODICI
*Attesting Officer*    *Acting Director of the United States Patent and Trademark Office*